United States Patent
Shin et al.

(10) Patent No.: US 11,569,451 B2
(45) Date of Patent: Jan. 31, 2023

(54) COMPOUND AND PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Jisoo Shin, Seoul (KR); Yeong Suk Choi, Suwon-si (KR); Katsunori Shibata, Hwaseong-si (KR); Taejin Choi, Suwon-si (KR); Sungyoung Yun, Suwon-si (KR); Ohkyu Kwon, Seoul (KR); Sangmo Kim, Hwaseong-si (KR); Hiromasa Shibuya, Seongnam-si (KR); Gae Hwang Lee, Seongnam-si (KR); Yong Wan Jin, Seoul (KR); Hyesung Choi, Seoul (KR); Chul Baik, Suwon-si (KR); Hyerim Hong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/475,688

(22) Filed: Sep. 15, 2021

(65) Prior Publication Data

US 2022/0006025 A1    Jan. 6, 2022

Related U.S. Application Data

(62) Division of application No. 16/165,005, filed on Oct. 19, 2018, now Pat. No. 11,145,822.

(30) Foreign Application Priority Data

Oct. 20, 2017 (KR) .................. 10-2017-0136882
Oct. 19, 2018 (KR) .................. 10-2018-0125469

(51) Int. Cl.
*H01L 51/00* (2006.01)
*H01L 51/42* (2006.01)
(Continued)

(52) U.S. Cl.
CPC ........ *H01L 51/0071* (2013.01); *C07D 409/06* (2013.01); *C07D 421/04* (2013.01);
(Continued)

(58) Field of Classification Search
CPC ............ H01L 51/4253; H01L 51/0052; H01L 51/0061; H01L 51/0062; H01L 51/0068;
(Continued)

(56) References Cited

U.S. PATENT DOCUMENTS 6,078,258 A   6/2000 Auerbach et al.
6,087,258 A   7/2000 Simpson et al.
(Continued)

FOREIGN PATENT DOCUMENTS

CN   1774823 A    5/2006
CN   102034933 A  4/2011
(Continued)

OTHER PUBLICATIONS

STIC structure search results Chemical Formula 1 of claim 1 (Year: 2022).*

(Continued)

*Primary Examiner* — Andrew J Golden
(74) *Attorney, Agent, or Firm* — Harness, Dickey & Pierce, P.L.C.

(57) ABSTRACT

A compound of Chemical Formula 1, and a photoelectric device, an image sensor, and an electronic device including the same are disclosed:

(Continued)

US 11,569,451 B2

Page 2

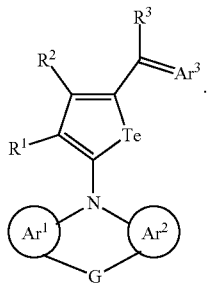

[Chemical Formula 1]

In Chemical Formula 1, each substituent is the same as defined in the detailed description.

17 Claims, 8 Drawing Sheets

(51) Int. Cl.
    *C07D 421/04*     (2006.01)
    *C07D 421/14*     (2006.01)
    *C07D 409/06*     (2006.01)
    *C07D 421/06*     (2006.01)
    *H01L 27/30*     (2006.01)
    *C07F 7/08*     (2006.01)
    *C07F 7/30*     (2006.01)
    *C07F 11/00*     (2006.01)

(52) U.S. Cl.
    CPC ......... *C07D 421/06* (2013.01); *C07D 421/14* (2013.01); *C07F 7/0816* (2013.01); *C07F 7/30* (2013.01); *C07F 11/00* (2013.01); *H01L 27/307* (2013.01); *H01L 51/0052* (2013.01); *H01L 51/0061* (2013.01); *H01L 51/0062* (2013.01); *H01L 51/0077* (2013.01); *H01L 51/0094* (2013.01); *H01L 51/4253* (2013.01); *H01L 51/0067* (2013.01); *H01L 51/0068* (2013.01)

(58) Field of Classification Search
CPC ............. H01L 51/0067; H01L 51/0071; H01L 51/0077; H01L 51/0094; H01L 27/307; C07D 409/06; C07D 421/04; C07D 421/06; C07D 421/14; C07F 7/30; C07F 7/0816
See application file for complete search history.

(56) References Cited

U.S. PATENT DOCUMENTS

| | | |
|---|---|---|
| 6,239,355 B1 | 5/2001 | Salafsky |
| 6,300,612 B1 | 10/2001 | Yu |
| 6,657,378 B2 | 12/2003 | Forrest et al. |
| 6,670,213 B2 | 12/2003 | Halls et al. |
| 6,824,952 B1 | 11/2004 | Minsek et al. |
| 6,972,431 B2 | 12/2005 | Forrest et al. |
| 7,129,466 B2 | 10/2006 | Iwasaki |
| 7,141,863 B1 | 11/2006 | Compaan et al. |
| 7,196,366 B2 | 3/2007 | Forrest et al. |
| 7,326,955 B2 | 2/2008 | Forrest et al. |
| 7,375,370 B2 | 5/2008 | Forrest et al. |
| 7,675,057 B2 | 3/2010 | Drechsel et al. |
| 7,768,194 B2 | 8/2010 | Forrest et al. |
| 7,893,352 B2 | 2/2011 | Thompson et al. |
| 7,915,701 B2 | 3/2011 | Forrest et al. |
| 7,947,897 B2 | 5/2011 | Rand et al. |
| 7,973,307 B2 | 7/2011 | Rand et al. |
| 7,982,130 B2 | 7/2011 | Forrest et al. |
| 8,017,863 B2 | 9/2011 | Forrest et al. |
| 8,035,708 B2 | 10/2011 | Takizawa et al. |
| 8,378,339 B2 | 2/2013 | Nomura et al. |
| 8,426,727 B2 | 4/2013 | Pfeiffer et al. |
| 8,466,452 B2 | 6/2013 | Kim et al. |
| 8,471,246 B2 | 6/2013 | Suzuki et al. |
| 8,525,577 B2 | 9/2013 | Yofu et al. |
| 8,592,680 B2 | 11/2013 | Rand et al. |
| 8,633,475 B2 | 1/2014 | Endo et al. |
| 8,637,860 B2 | 1/2014 | Nomura et al. |
| 8,704,213 B2 | 4/2014 | Suzuki |
| 8,704,281 B2 | 4/2014 | Maehara et al. |
| 8,766,291 B2 | 7/2014 | Forrest et al. |
| 8,847,066 B2 | 9/2014 | Holmes et al. |
| 8,847,141 B2 | 9/2014 | Fukuzaki et al. |
| 8,847,208 B2 | 9/2014 | Mitsui et al. |
| 8,860,016 B2 | 10/2014 | Suzuki |
| 8,933,438 B2 | 1/2015 | Leem et al. |
| 8,987,589 B2 | 3/2015 | Rand et al. |
| 8,994,132 B2 | 3/2015 | Mitsui et al. |
| 9,024,181 B2 | 5/2015 | Pfeiffer et al. |
| 9,029,837 B2 | 5/2015 | Forrest et al. |
| 9,054,329 B2 | 6/2015 | Coe-Sullivan et al. |
| 9,070,887 B2 | 6/2015 | Yofu et al. |
| 9,070,888 B2 | 6/2015 | Leem et al. |
| 9,490,442 B2 | 11/2016 | Leem et al. |
| 9,505,770 B2 | 11/2016 | McGrath et al. |
| 9,508,945 B2 | 11/2016 | Holmes et al. |
| 9,543,361 B2 | 1/2017 | Leem et al. |
| 9,548,463 B2 | 1/2017 | Yagi et al. |
| 9,577,221 B2 | 2/2017 | Weaver et al. |
| 9,608,212 B2 | 3/2017 | Ishibe et al. |
| 9,680,103 B2 | 6/2017 | Sugiura et al. |
| 9,941,477 B2 | 4/2018 | Choi et al. |
| 9,960,362 B2 | 5/2018 | Bulliard et al. |
| 10,043,992 B2 | 8/2018 | Park et al. |
| 10,069,095 B2 | 9/2018 | Forrest et al. |
| 10,074,810 B2 | 9/2018 | Lui et al. |
| 10,326,083 B2 | 6/2019 | Yagi et al. |
| 10,461,256 B2 | 10/2019 | Choi et al. |
| 10,505,146 B2 | 12/2019 | Heo et al. |
| 10,978,654 B2 | 4/2021 | Forrest et al. |
| 11,094,902 B2 | 8/2021 | Forrest et al. |
| 11,114,634 B2 | 9/2021 | Park et al. |
| 11,121,336 B2 | 9/2021 | Forrest et al. |
| 2004/0192942 A1 | 9/2004 | Huang |
| 2005/0217722 A1 | 10/2005 | Komatsu et al. |
| 2006/0076050 A1 | 4/2006 | Williams et al. |
| 2007/0012955 A1 | 1/2007 | Ihama |
| 2007/0063156 A1 | 3/2007 | Hayashi |
| 2007/0090371 A1 | 4/2007 | Drechsel et al. |
| 2010/0084011 A1 | 4/2010 | Forrest et al. |
| 2010/0207112 A1 | 8/2010 | Furst et al. |
| 2011/0012091 A1 | 1/2011 | Forrest et al. |
| 2011/0074491 A1 | 3/2011 | Yofu et al. |
| 2012/0126204 A1 | 5/2012 | So et al. |
| 2012/0217448 A1 | 8/2012 | Yoshimura et al. |
| 2012/0266958 A1 | 10/2012 | Aksu et al. |
| 2012/0313088 A1 | 12/2012 | Yofu et al. |
| 2013/0062595 A1 | 3/2013 | Park et al. |
| 2013/0087682 A1 | 4/2013 | Nomura |
| 2013/0181202 A1 | 7/2013 | Yofu et al. |
| 2013/0206218 A1 | 8/2013 | Holmes et al. |
| 2013/0299799 A1 | 11/2013 | Yofu et al. |
| 2014/0008619 A1 | 1/2014 | Lee et al. |
| 2014/0054442 A1 | 2/2014 | Huang et al. |
| 2014/0083496 A1 | 3/2014 | Shibasaki et al. |
| 2014/0159752 A1 | 6/2014 | Tsai et al. |
| 2014/0209173 A1 | 7/2014 | Momose |
| 2014/0319509 A1 | 10/2014 | Hattori et al. |
| 2014/0360585 A1 | 12/2014 | Sugiura et al. |
| 2015/0053942 A1 | 2/2015 | Kho et al. |
| 2015/0060775 A1 | 3/2015 | Liang et al. |
| 2015/0162548 A1 | 6/2015 | Lim et al. |
| 2015/0200226 A1 | 7/2015 | Jin et al. |
| 2015/0228811 A1 | 8/2015 | Hiroi et al. |
| 2015/0287946 A1 | 10/2015 | Leem et al. |
| 2015/0349073 A1 | 12/2015 | Kang |

(56) References Cited

U.S. PATENT DOCUMENTS

| | | |
|---|---|---|
| 2015/0349283 A1 | 12/2015 | Forrest et al. |
| 2016/0013248 A1 | 1/2016 | Sawaki |
| 2016/0013424 A1 | 1/2016 | Yamamoto et al. |
| 2016/0020258 A1 | 1/2016 | Park et al. |
| 2016/0064672 A1 | 3/2016 | Lee et al. |
| 2016/0099417 A1 | 4/2016 | Sato et al. |
| 2016/0100153 A1 | 4/2016 | Jeon et al. |
| 2016/0111561 A1 | 4/2016 | Hsu et al. |
| 2016/0111651 A1 | 4/2016 | Yun et al. |
| 2016/0126470 A1 | 5/2016 | Ro et al. |
| 2016/0149132 A1 | 5/2016 | Lim et al. |
| 2016/0197281 A1 | 7/2016 | Momose et al. |
| 2016/0254101 A1 | 9/2016 | Forrest et al. |
| 2016/0268401 A1 | 9/2016 | Aleksov |
| 2017/0005142 A1 | 1/2017 | Lee et al. |
| 2017/0062726 A1 | 3/2017 | Choi et al. |
| 2017/0074652 A1 | 3/2017 | Send et al. |
| 2017/0117424 A1 | 4/2017 | Hiroi et al. |
| 2017/0148994 A1 | 5/2017 | Choi et al. |
| 2017/0213973 A1 | 7/2017 | Yun et al. |
| 2017/0294589 A1 | 10/2017 | Shibuya et al. |
| 2017/0331050 A1 | 11/2017 | Yagi et al. |
| 2017/0352811 A1 | 12/2017 | Choi et al. |
| 2018/0151624 A1 | 5/2018 | Hasegawa et al. |
| 2020/0127232 A1 | 4/2020 | Heo et al. |

FOREIGN PATENT DOCUMENTS

| | | |
|---|---|---|
| CN | 103000810 A | 3/2013 |
| CN | 104230953 A | 12/2014 |
| CN | 104979476 A | 10/2015 |
| CN | 105051929 A | 11/2015 |
| DE | 87576 A | 2/1972 |
| DE | 102004014046 A1 | 9/2004 |
| EP | 0193885 A1 | 9/1986 |
| EP | 0529162 A1 | 3/1993 |
| EP | 0637774 A1 | 2/1995 |
| EP | 2317582 A1 | 5/2011 |
| EP | 3018723 A1 | 5/2016 |
| EP | 3026722 A1 | 6/2016 |
| EP | 3173410 A1 | 5/2017 |
| EP | 3243822 A1 | 11/2017 |
| EP | 3252051 A1 | 12/2017 |
| JP | H06143839 A | 5/1994 |
| JP | H09-311232 A | 12/1997 |
| JP | H1091384 A | 4/1998 |
| JP | 2005-123033 A | 5/2005 |
| JP | 2005-132914 A | 5/2005 |
| JP | 2006-261172 A | 9/2006 |
| JP | 2007-234650 A | 9/2007 |
| JP | 2009-274966 A | 11/2009 |
| JP | 2011-225544 A | 11/2011 |
| JP | 2011-253861 A | 12/2011 |
| JP | 2012-123292 A | 6/2012 |
| JP | 2012-151761 A | 8/2012 |
| JP | 2013-040147 A | 2/2013 |
| JP | 5323025 B2 | 10/2013 |
| JP | 2014-049559 A | 3/2014 |
| JP | 5520560 B2 | 6/2014 |
| JP | 2014-210768 A | 11/2014 |
| JP | 2015-015415 A | 1/2015 |
| JP | 2015-043362 A | 3/2015 |
| JP | 2015-070060 A | 4/2015 |
| JP | 2015-092546 A | 5/2015 |
| KR | 2012-0122847 A | 11/2012 |
| KR | 2014-0106767 A | 9/2014 |
| KR | 2015-0066616 A | 6/2015 |
| KR | 2016-0009404 A | 1/2016 |
| KR | 2016-0024686 A | 3/2016 |
| KR | 2016-0041379 A | 4/2016 |
| KR | 10-2016-0052448 A | 5/2016 |
| KR | 10-2016-0062708 A | 6/2016 |
| KR | 2017-0027223 A | 3/2017 |
| KR | 2017-0060488 A | 6/2017 |
| KR | 10-2017-0114839 A | 10/2017 |
| KR | 10-2017-0126753 A | 11/2017 |
| KR | 2017-0135449 A | 12/2017 |
| KR | 2017-0137648 A | 12/2017 |
| WO | WO-2002-064600 A1 | 8/2002 |
| WO | WO-2008-091670 A2 | 7/2008 |
| WO | WO-2010-011658 A2 | 1/2010 |
| WO | WO-2010-038721 A1 | 4/2010 |
| WO | WO-2014-056886 A1 | 4/2014 |
| WO | WO-2014-157238 A1 | 10/2014 |
| WO | WO-2014/169270 A2 | 10/2014 |

OTHER PUBLICATIONS

Ex Parte Quayle Action dated May 4, 2022 issued in corresponding U.S. Appl. No. 15/471,289.
Yuan et al., "Intermediate Layers in Tandem Organic Solar Cells" Green 1 (2011), pp. 65-80.
Seo, Hokuto. "Color Sensors with Three Vertically Stacked Organic Photodetectors" Jap. J. Appl. Phys. 46(49), 2007, L1240-L1242.
Aihara, Satoshi. "Stacked Image SensorWith Green- and Red-Sensitive Organic Photoconductive Films Applying Zinc Oxide Thin-Film Transistors to a Signal Readout Circuit" IEEE Trans. Electron. Dev., 56(11), 2009, 2570.
Ihama, Mikio. "CMOS Image Sensor with a Thin Overlaid Panchromatic Organic Photoconductive Layer for Sensors with Reduced Pixel Size" IDW '09, INP 1-4.
Abstract for JP2012-38435 (issued Feb. 23, 2012), retrieved from STN Database, CAPLUS Accession No. 2012:265934, XP002771880.
Extended European Search Report dated Feb. 4, 2019, issued in corresponding European Patent Application No. 18201486.0.
Drechsel J. et al: "Efficient organic solar cells based on a double p-i-n architecture using doped wide-gap transport layers", Applied Physics Letters, AIP Publishing LLC, US, vol. 86, No. 24, Jun. 7, 2005 (Jun. 7, 2005). pp. 244102-244102, XP012065900, ISSN: 0003-6951, DOI: 10.1063/1.1935771.
European Extended Search Report for Application No. 171770027 dated Nov. 17, 2017.
U.S. Office Action dated Jul. 25, 2018 issued in co-pending U.S. Appl. No. 15/272,580.
U.S. Office Action dated Aug. 6, 2018 issued in co-pending U.S. Appl. No. 15/623,801.
Juha Alakarhu. "Image Sensors and Image Quality in Mobile Phones", International Image Sensor Workshop. 2007. pp. 104.
I.G. Hill et al., Organic Electronics, "Metal-dependent charge transfer and chemical interaction at interfaces between 3, 4, 9, 10-perylenetetracarboxylic bisimidazole and gold, silver, and magnesium", vol. 1, Issue 1, Dec. 2000, pp. 5-13.
Marzena Grucela-Zajac et al., "(Photo)physical Properties of New Molecular Glasses End-Capped with Thiphene Rings Composed of Diimide and Imine Units", The Journal of Phyusical Chemistry, May 21, 2014, pp. 13070-13086, ACS Author Choice.
Gorkem Memisoglu et al., "Highly Efficient Organic UV Photodetectors Base don Polyfluorene and Napthalenediimide Blends: Effect of Thermal Annealing", 2012, International Journal of Photoenergy vol. 2012, Article ID 936075, 11 pages, Hindawi Publishing Corporation.
Jiri Misek et al., "A Chiral and Colorful Redox Switch: Enhanced p Acidity in Action", 2010, Angew. Chem. Int. Ed. 2010, 49, 7680-7683, Wiley-VCH Verlag GmbH & Co., KGaA, Weinheim.
European Search Report dated Apr. 26, 2017 issued in corresponding European Application No. 16195944.0.
European Search Report issued in corresponding European Patent Application No. 17150423.6-1555 dated Aug. 4, 2017.
U.S. Notice of Allowance dated Dec. 20, 2017 issued in co-pending U.S. Appl. No. 15/609,125.
U.S. Office Action dated Feb. 14, 2018 issued in co-pending U.S. Appl. No. 15/272,580.
U.S. Office Action dated Jan. 5, 2018 issued in co-pending U.S. Appl. No. 15/362,964.
U.S. Office Action dated Jun. 1, 2018 issued in co-pending U.S. Appl. No. 15/362,964.
U.S. Office Action dated Jul. 3, 2017 ssued in co-pending U.S. Appl. No. 15/255,649.

(56) References Cited

OTHER PUBLICATIONS

U.S. Office Action dated Jan. 29, 2018 issued in co-pending U.S. Appl. No. 15/255,649.
U.S. Office Action dated Aug. 24, 2018 issued in co-pending U.S. Appl. No. 15/461,914.
Extended European Search Report dated May 22, 2017, for corresponding European Patent Application No. 17161078.5.
U.S. Office Action dated Jan. 10, 2020, issued in corresponding U.S. Appl. No. 15/471,289.
U.S. Office Action dated Mar. 15, 2021, issued in corresponding U.S. Appl. No. 15/471,289.
STIC STN Chemical structure search results for Formula 1 (Year: 2021).
U.S. Office Action dated Feb. 14, 2019 issued in corresponding U.S. Appl. No. 15/623,801.
U.S. Notice of Allowance dated Jul. 11, 2019, issued in corresponding U.S. Appl. No. 15/623,801.
Iwaoka, et al. "Possible roles of S O and S N interations in the functions and evolution of phospholipase A2," Biophysics, vol. 2, pp. 23-34 (2006).
Iwaoka, et al. Studies on the Nonbonded Interactions of Divalent Organic Selenium, Department of Chemistry, School of Science, Tokai University, vol. 63, No. 9, pp. 63-72 (2005).
Jen, et al. "Synthesis and Characterization of Highly Efficient and Thermally Stable Diphenylamino-Substituted Thiophene Stilbene Chromophores for Nonlinear Optical Applications," Advanced Materials, . vol. 9, No. 2, pp. 132-135 (1997).
Lim, et al. "Organic-on-silicon complementary metal-oxide-semiconductor colour image sensors," Scientific Reports, vol. 5, pp. 1-7 (2014).
Singh, et al. "Radical Cations of Aromatic Selenium Compounds: Role of Se X Nonbonding Interations," The Journal of Physical Chemistry, vol. 117, pp. 9259-9265 (2013).
U.S. Office Action dated Jan. 7, 2019 issued in corresponding U.S. Appl. No. 15/611,901.
U.S. Office Action dated Apr. 1, 2019 issued in corresponding U.S. Appl. No. 15/611,901.
U.S. Notice of Allowance dated Jun. 19, 2019, issued in corresponding U.S. Appl. No. 15/611,901.
Bulliard, et al. "Dipolar donor-acceptor molecules in the cyanine limit for high efficiency green-light-selective organic photodiodes," Journal of Materials Chemistry C., vol. 4, pp. 1117-1125 (2016).
Heichert, et al. "Synthesis and characterization of long wavelength-absorbing donor/acceptor-substituted methane dyes," Zeitschrift For Naturforschung—Section B, Journal of Chemical Sciences, vol. 71, No. 6, pp. 2-9 (2016).
Matsumoto, et al. "Utilization of Carboxylated 1, 3-Indandione as an Electron Acceptor in Dye-Sensitized Solar Cells," Bulletin of the Chemical Society of Japan, vol. 85, No. 12, pp. 1329-1331 (2012).
Extended European Search Report dated Nov. 2, 2017 issued in corresponding European Patent Application No. 17174434.5.
U.S. Office Action dated Aug. 1, 2018 issued in corresponding U.S. Appl. No. 15/591,259.
U.S. Notice of Allowance dated Jan. 25, 2019, issued in corresponding U.S. Appl. No. 15/591,259.
Jeux, et al. "Miniaturization of molecular conjugated systems for organic solar cells: towards pigmy donors," RCS Adv. vol. 3, pp. 5811-5814 (2013).
Chun, et al. "The effects of the molecular structure if the chromophore on the photo refractive properties of the polymer systems with low glass transition temperatures," J. Mater. Chem., vol. 12, pp. 858-862 (2002).
CAPLUS Abstract (XP-002771879) for Guo, et al. "Acceptors/linkers effects on dye sensitized solar cell: Theoretical investigations of structure-property relationship for design of efficient dye sensitizers," Journal of Theoretical and Computational Chemistry, vol. 13, No. 7, pp. 1-3 (2014).
Kim, et al. "Synthesis and Photovoltaic Performance of Long Wavelength Absorbing Organic Dyes for Dye-Sensitized Solar Cells," Molecular Crystals and Liquid Crystals, vol. 551, No. 1, pp. 283-294 (2011).
CAPLUS Abstract (XP-002771880) for Hamada, et al. "Dye-sensitized photoelectric converter, photoelectrochemical cell, and dye solution for photoelectric converter," Jpn. Kokail Tokkyo Koho, pp. 1-2 (2012).
Yang, et al. "Synthesis and Photovoltaic Properties of Organic Photosensitizers Based on Phenothiazine Chromophore for Application of Dye-Sensitized Solar Cells," Molecular Crystals and Liquid Crystals, vol. 538, No. 1, pp. 149-156 (2011).
Extended European Search Report dated Jul. 19, 2017 issued in corresponding European Application No. 17170200.4.
U.S. Office Action dated Aug. 13, 2020, issued in corresponding U.S. Appl. No. 15/471,289.
U.S. Office Action dated Aug. 20, 2021, issued in corresponding U.S. Appl. No. 15/471,289.
U.S. Notice of Allowance dated Jun. 30, 2022, issued in corresponding U.S. Appl. No. 15/471,289.
Advisory Action dated Nov. 2, 2021, issued in corresponding U.S. Appl. No. 15/471,289.
Office Action dated Oct. 17, 2022, issued in corresponding Chinese Patent Application No. 201710513122.4.

\* cited by examiner

COMPOUND AND PHOTOELECTRIC DEVICE, IMAGE SENSOR, AND ELECTRONIC DEVICE INCLUDING THE SAME

CROSS-REFERENCE TO RELATED APPLICATION

This application is a divisional of U.S. application Ser. No. 16/165,005, filed Oct. 19, 2018, which claims priority under 35 U.S.C. § 119 to Korean Patent Application Nos. 10-2017-0136882 and 10-2018-0125469 filed in the Korean Intellectual Property Office on Oct. 20, 2017 and Oct. 19, 2018 respectively, the entire contents of each of which are incorporated herein by reference.

BACKGROUND

1. Field

Example embodiments relate to a compound and a photoelectric device, an image sensor, and/or an electronic device including the same.

2. Description of Related Art

A photoelectric device converts light into an electrical signal using photoelectric effects, it may include a photodiode, a phototransistor, and the like, and it may be applied to an image sensor, a solar cell, a light emitting device, and the like.

An image sensor including a photodiode may have high resolution and thus a small pixel. At present, a silicon photodiode is widely used, but it has deteriorated sensitivity since it has a small absorption area due to small pixels. Accordingly, an organic material that is capable of replacing silicon has been researched.

An organic material has a high extinction coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in a green wavelength region and maintaining improved efficiency during a high-temperature process.

Example embodiments also provide an image sensor including the photoelectric device (e.g., organic photoelectric device).

Example embodiments also provide an electronic device including the image sensor.

According to example embodiments, a compound represented by Chemical Formula 1 is provided.

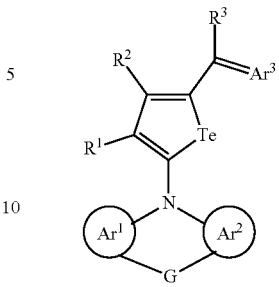

[Chemical Formula 1]

In Chemical Formula 1, $Ar^3$ may be one of a substituted or unsubstituted hydrocarbon cyclic group having two carbonyl groups, a substituted or unsubstituted heterocyclic group having two carbonyl groups, or a fused ring thereof, $R^1$ to $R^3$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $R^1$ and $R^2$ may independently be present or linked with each other to provide a ring, $Ar^1$ and $Ar^2$ may independently be one of a substituted or unsubstituted C6 to C30 arene group, a substituted or unsubstituted C3 to C30 heteroarene group, and a combination thereof in a condensed ring, and G may be one of —$(CR^dR^e)_n$—, —O—, —S—, —Se—, —N=, —$NR^f$—, —$SiR^gR^h$—, —$SiR^{gg}R^{hh}$—, —$GeR^iR^j$—, —$GeR^{ii}R^{jj}$—, —$(C(R^m)=C(R^n))$—, —$(C(R^{mm})=C(R^{nn}))$—, or a single bond (wherein $R^d$, $R^e$, $R^f$, $R^g$, $R^h$, $R^i$, $R^j$, $R^m$, and $R^n$ may independently be one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure), and n in —$(CR^dR^e)_n$— may be 1 or 2).

In some embodiments, in Chemical Formula 1, $Ar^3$ may be a cyclic group represented by one of Chemical Formula 2A to Chemical Formula 2D.

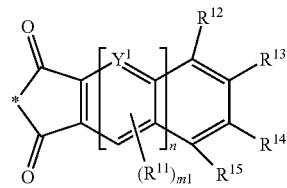

[Chemical Formula 2A]

In Chemical Formula 2A, $Y^1$ may be one of N or $CR^a$ (wherein $R^a$ is one of hydrogen, deuterium or a substituted or unsubstituted C1 to C10 alkyl group), $R^{11}$, $R^{12}$, $R^{13}$, $R^{14}$, and $R^{15}$ may be one of hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, or $R^{12}$ and $R^{13}$ and $R^{14}$ and $R^{15}$ may independently be linked with each other to provide an aromatic ring, m1 may be 0 or 1, n in Chemical Formula 2A may be 0 or 1, and

* may be a linking point.

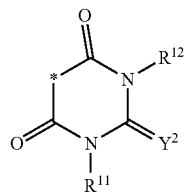

[Chemical Formula 2B]

In Chemical Formula 2B, $Y^2$ may be one of O, S, Se, Te, and $C(R^a)(CN)$ (wherein $R^a$ may be one of hydrogen, a cyano group (—CN), or a C1 to C10 alkyl group), $R^{11}$ and $R^{12}$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

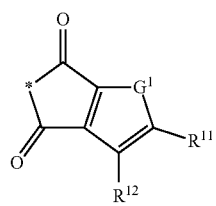

[Chemical Formula 2C]

In Chemical Formula 2C, $G^1$ may be one of —S—, —Se—, —GeR$^x$R$^y$—, or —Te—, wherein $R^x$ and $R^y$ may be the same or different and may be independently one of hydrogen, a halogen, a substituted or unsubstituted C1 to C10 alkyl group, or a substituted or unsubstituted C6 to C10 aryl group, $R^{11}$ and $R^{12}$ may be the same or different and may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking point.

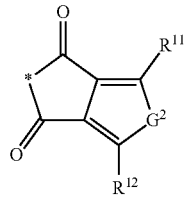

[Chemical Formula 2D]

In Chemical Formula 2D, $G^2$ is one of —S—, —Se—, —GeR$^x$R$^y$—, or —Te—, wherein $R^x$ and $R^y$ are the same or different and are independently one of hydrogen, a halogen, a substituted or unsubstituted C1 to C10 alkyl group, or a substituted or unsubstituted C6 to C10 aryl group, $R^{11}$ and $R^{12}$ may be the same or different and may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* is a linking point.

In Chemical Formula 1, at least one of $Ar^1$ and $Ar^2$ may include a heteroatom at No. 1 position, and the heteroatom may be one of nitrogen (N), sulfur (S), or selenium (Se).

In some embodiments, an electron donor moiety (e.g., 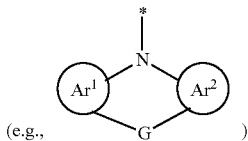 )

of N-containing hetero aromatic ring in Chemical Formula 1 may be represented by one of Chemical Formula 4A to Chemical Formula 4E.

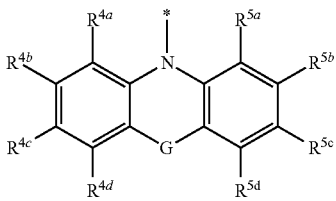

[Chemical Formula 4A]

In Chemical Formula 4A,

G may be the same as in Chemical Formula 1, and $R^{4a}$ to $R^{4d}$ and $R^{5a}$ to $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof. Two adjacent groups of $R^{4a}$ to $R^{4d}$ may be linked with each other to provide a 5-membered aromatic ring or a 6-membered aromatic ring, or two adjacent groups of $R^{5a}$ to $R^{5d}$ may be linked with each other to provide a 5-membered aromatic ring or a 6-membered aromatic ring.

[Chemical Formula 4B]

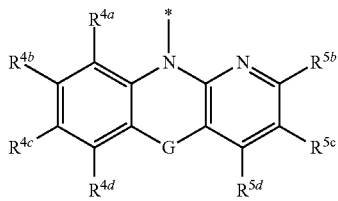

In Chemical Formula 4B,

G may be the same as in Chemical Formula 1, $R^{4a}$ to $R^{4d}$ and $R^{5b}$ to $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof. Two adjacent groups of $R^{4a}$ to $R^{4d}$ may be linked with each other to provide a 5-membered aromatic ring or a 6-membered aromatic ring, or two adjacent groups of $R^{5b}$ to $R^{5d}$ may be linked with each other to provide a 5-membered aromatic ring or a 6-membered aromatic ring.

[Chemical Formula 4C]

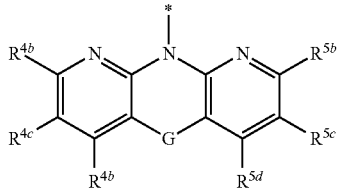

In Chemical Formula 4C,

G may be the same as in Chemical Formula 1, $R^{4b}$ to $R^{4d}$ and $R^{5b}$ to $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof. Two adjacent groups of $R^{4b}$ to $R^{4d}$ may be linked with each other to provide a 5-membered aromatic ring or a 6-membered aromatic ring, or two adjacent groups of $R^{5b}$ to $R^{5d}$ may be linked with each other to provide a 5-membered aromatic ring or a 6-membered aromatic ring.

[Chemical Formula 4D]

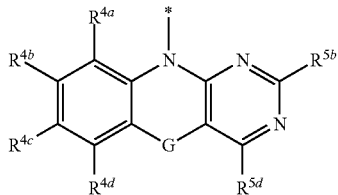

In Chemical Formula 4D,

G may be the same as in Chemical Formula 1, and $R^{4a}$ to $R^{4d}$ and $R^{5b}$ and $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof. Two adjacent groups of $R^{4a}$ to $R^{4d}$ may be linked with each other to provide a 5-membered aromatic ring or a 6-membered aromatic ring.

[Chemical Formula 4E]

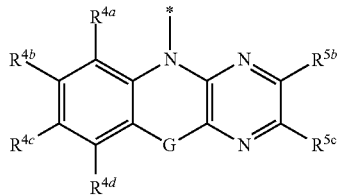

In Chemical Formula 4E,

G may be the same as in Chemical Formula 1, and $R^{4a}$ to $R^{4d}$ and $R^{5b}$ and $R^{5c}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof. Two adjacent groups of $R^{4a}$ to $R^{4d}$ may be linked with each other to provide a 5-membered aromatic ring or a 6-membered aromatic ring, or $R^{5b}$ and $R^{5c}$ may be linked with each other to provide a 5-membered aromatic ring or a 6-membered aromatic ring.

In some example embodiments, the compound may have a maximum absorption wavelength ($\lambda_{max}$) in a wavelength region of greater than or equal to about 500 nm and less than or equal to about 600 nm, in a thin film state.

In some example embodiments, the compound may exhibit a light absorption curve having a full width at half maximum (FWHM) of about 50 nm to about 120 nm, in a thin film state.

In some example embodiments, a difference between a melting point of the compound and a temperature (deposition temperature) at which 10 wt % of an initial weight of the compound may be lost may be greater than or equal to about 3° C.

According to some example embodiments, a photoelectric device may include a first electrode and a second electrode facing each other and an active layer between the first electrode and the second electrode, and the active layer may include the compound represented by Chemical Formula 1.

According to some example embodiments, an image sensor may include the photoelectric device (e.g., organic photoelectric device).

In some example embodiments, the image sensor may include a semiconductor substrate and a photoelectric device on the semiconductor substrate. The semiconductor substrate may be integrated with a plurality of first photo-sensing devices configured to sense light in a blue wavelength region and a plurality of second photo-sensing devices configured to sense light in a red wavelength region, and the photoelectric device on the semiconductor substrate may be configured to selectively sense light in a green wavelength region.

In some example embodiments, the first photo-sensing device and the second photo-sensing device may be stacked in a vertical direction in the semiconductor substrate.

In some example embodiments, the image sensor may further include a color filter layer, and the color filter layer may include a blue filter configured to selectively transmit light in a blue wavelength region and a red filter configured to selectively transmit light in a red wavelength region.

In some example embodiments, the image sensor may include a green photoelectric device, a blue photoelectric device configured to selectively absorb light in a blue wavelength region, and a red photoelectric device configured to selectively absorb light in a red wavelength region that may be stacked. The green photoelectric device may be the above-mentioned photoelectric device (e.g., the organic photoelectric device).

According to some example embodiments, an electronic device includes the image sensor.

The compound may selectively absorb light in a green wavelength region and has improved thermal stability. The photoelectric device (e.g., organic photoelectric device), the image sensor, and the electronic device including the compound may exhibit high efficiency due to improved wavelength selectivity and may not exhibit decrease of performance even through a high temperature process.

DETAILED DESCRIPTION

Figure 1:
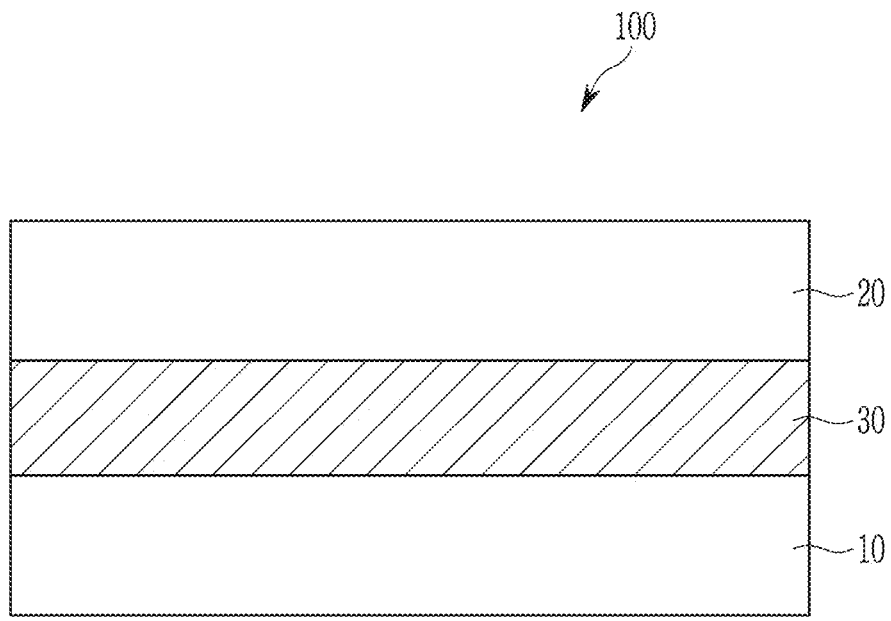
FIG. 1 is a cross-sectional view of a photoelectric device according to an example embodiment.

Example embodiments will hereinafter be described in detail, and may be easily performed by person skilled in the art in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C."

As used herein, when a definition is not otherwise provided, "substituted" refers to replacement of hydrogen of a compound or a group by at least one of a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, =S, and a combination thereof.

As used herein, when specific definition is not otherwise provided, "hetero" may refer to one including 1 to 3 heteroatoms selected from N, O, S, P, and Si.

As used herein, "an alkyl group" may refer to a straight or branched saturated monovalent hydrocarbon group, for example, a methyl group, an ethyl group, a propyl group, an isopropyl group, an n-butyl group, an isobutyl group, a t-butyl group, a pentyl group, a hexyl group, and the like.

As used herein, "a cycloalkyl group" may refer to a monovalent cyclic hydrocarbon group in which all ring-forming atoms are carbon, for example, a cyclopropyl group, a cyclobutyl group, a cyclopentyl group, a cyclohexyl group, and the like.

As used herein, "an aryl group" may refer to a group in which all elements of the cycle have p-orbitals which form conjugation, and may be a monocyclic, polycyclic or fused polycyclic (e.g., rings sharing adjacent pairs of carbon atoms) functional group.

As used herein, when a definition is not otherwise provided, "a cyano-containing group" may refer to a monovalent group such as a C1 to C30 alkyl group, a C2 to C30 alkenyl group, or a C2 to C30 alkynyl group where at least one hydrogen is replaced by a cyano group. The cyano-containing group may also refer to a divalent group such as a group represented by $=CR^{x'}-(CR^xR^y)_p-CR^{y'}(CN)_2$ wherein $R^x$, $R^y$, $R^{x'}$, and $R^{y'}$ are the same or different and are independently one of hydrogen and a C1 to C10 alkyl group and p is an integer of 0 to 10 (and/or 1 to 10). Specific examples of the cyano-containing group may be a dicyanomethyl group, a dicyanovinyl group, a cyanoethynyl group, and the like. The term "cyano-containing group" does not cover the cyano group (—CN) itself.

As used herein, when a definition is not otherwise provided, "a combination thereof" may refer to at least two groups bound to each other by a single bond or a C1 to C10 alkylene group, or at least two groups fused to each other.

As used herein, "hydrocarbon cyclic group" may refer to a fused ring of an arene ring (aromatic ring) and an alicyclic hydrocarbon ring (non-aromatic ring), and may be for example a fused ring where at least one arene ring such as a C6 to C30 aryl group, for example a C6 to C20 aryl group or a C6 to C10 aryl group and at least one alicyclic hydrocarbon ring such as a C3 to C30 cycloalkyl group, for example a C3 to C20 cycloalkyl group or a C3 to C10 cycloalkyl group are condensed with each other.

As used herein, "arene group" may refer to a hydrocarbon group having an aromatic ring, and includes monocyclic and polycyclic hydrocarbons, wherein the additional ring(s) of the polycyclic hydrocarbon may be aromatic or nonaromatic. "Heteroarene group" may refer to an arene group including one to three heteroatoms selected from N, O, S, P, and Si in a ring.

As used herein, "heterocyclic group" may refer to a group obtained by replacing one to three carbon atoms in a ring of arene group (e.g., a C6 to C30 aryl group, a C6 to C20 aryl group, or a C6 to C10 aryl group), alicyclic hydrocarbon group (e.g., a C3 to C30 cycloalkyl group, a C3 to C20 cycloalkyl group, or a C3 to C10 cycloalkyl group), or a fused ring thereof with heteroatoms selected from N, O, S, P, and Si. One or more carbon atoms in a ring of the heterocyclic group may be optionally substituted by =S, that is, a thiocarbonyl group (C=S) can be formed.

As used herein, "C6 to C30 aromatic hydrocarbon group" may include a C6 to C30 aryl group such as a phenyl group or a naphthyl group, a C6 to C30 arylene group, and the like, but is not limited thereto.

As used herein, "aliphatic hydrocarbon group" may be for example, a C1 to C15 alkyl group such as a methyl group, an ethyl group, or a propyl group, a C1 to C15 alkylene group, a C2 to C15 alkenyl group such as ethenyl group or propenyl group, a C2 to C15 alkenylene group, a C2 to C15 alkynyl group such as ethynyl group or propynyl group, and the like, but is not limited thereto.

As used herein, "5-membered aromatic ring" refers to a 5-membered cyclic group (e.g., C5 aryl group) having a conjugation structure or a 5-membered heterocyclic group (e.g., C2 to C4 heteroaryl group) having a conjugation structure. As used herein, "6-membered aromatic ring" refers to a 6-membered cyclic group (e.g., C6 aryl group) having a conjugation structure or a 6-membered heterocyclic group (e.g., C2 to C5 heteroaryl group) having a conjugation structure, but is not limited thereto. The aromatic ring may include the 5-membered aromatic ring or the 6-membered aromatic ring, but is not limited thereto.

As used herein, "maximum absorption wavelength" refers to a wavelength at which the absorbance is the maximum, and can also be referred to as "peak absorption wavelength".

Hereinafter, a compound according to an embodiment is described. The compound is represented by Chemical Formula 1.

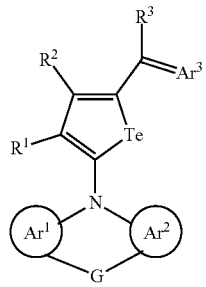

[Chemical Formula 1]

In Chemical Formula 1, $Ar^3$ may be one of a substituted or unsubstituted hydrocarbon cyclic group having two carbonyl groups, a substituted or unsubstituted heterocyclic group having two carbonyl groups, or a fused ring thereof, $R^1$ to $R^3$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $R^1$ and $R^2$ may independently be present or linked with each other to provide a ring, $Ar^1$ and $Ar^2$ may independently be one of a substituted or unsubstituted C6 to C30 arene group, a substituted or unsubstituted C3 to C30 heteroarene group, or a combination thereof in a condensed ring, and G may be one of —$(CR^dR^e)_n$—, —O—, —S—, —Se—, —N=, —$NR^f$—, —$SiR^gR^h$—, —$SiR^{gg}R^{hh}$—, —$GeR^iR^j$—, —$GeR^{ii}R^{jj}$—, —$(C(R^m)=C(R^n))$—, —$(C(R^{mm})=C(R^{nn}))$—, and a single bond (wherein $R^d$, $R^e$, $R^f$, $R^g$, $R^h$, $R^i$, $R^j$, $R^m$, and $R^n$ may independently be one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure), and n in —$(CR^dR^e)_n$— is 1 or 2).

The compound represented by Chemical Formula 1 includes an electron donor moiety of the N-containing hetero aromatic ring, a linker including a Te-containing 5-membered ring, and an electron acceptor moiety represented by $Ar^3$.

In Chemical Formula 1, the cyclic group represented by $Ar^3$ is an electron acceptor moiety and includes at least two carbonyl groups. $Ar^3$ may be one of a substituted or unsubstituted hydrocarbon cyclic group having two carbonyl groups, a substituted or unsubstituted heterocyclic group having two carbonyl groups, or a fused ring thereof.

In some embodiments, $Ar^3$ may be one of a substituted or unsubstituted 5-membered aromatic ring, a substituted or unsubstituted 6-membered aromatic ring, or a condensed ring of two or more of the foregoing rings.

In Chemical Formula 1, $Ar^3$ may be a cyclic group represented by one of Chemical Formula 2A to Chemical Formula 2D.

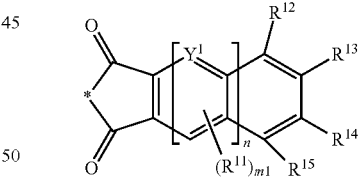

[Chemical Formula 2A]

In Chemical Formula 2A, $Y^1$ may be one of N or $CR^a$ (wherein $R^a$ is one of hydrogen, deuterium or a substituted or unsubstituted C1 to C10 alkyl group), $R^{11}$, $R^{12}$, $R^{13}$, $R^{14}$, and $R^{15}$ may be one of hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or $R^{12}$ and $R^{13}$ and $R^{14}$ and $R^{15}$ may independently be linked with each other to provide an aromatic ring, m1 may be 0 or 1, n in Chemical Formula 2A may be 0 or 1, and

* may be a linking point.

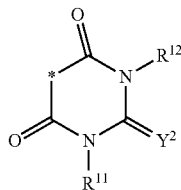

[Chemical Formula 2B]

In Chemical Formula 2B, $Y^2$ may be one of O, S, Se, Te, or $C(R^a)(CN)$ (wherein $R^a$ may be one of hydrogen, a cyano group (—CN), or a C1 to C10 alkyl group), $R^{11}$ and $R^{12}$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

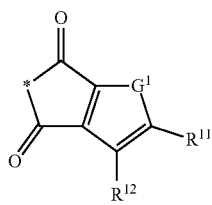

[Chemical Formula 2C]

In Chemical Formula 2C, $G^1$ may be one of —S—, —Se—, —GeR$^x$R$^y$—, or —Te—, wherein $R^x$ and $R^y$ may be the same or different and may be independently one of hydrogen, a halogen, a substituted or unsubstituted C1 to C10 alkyl group, or a substituted or unsubstituted C6 to C10 aryl group, $R^{11}$ and $R^{12}$ may be the same or different and may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* may be a linking point.

[Chemical Formula 2D]

In Chemical Formula 2D, $G^2$ may be one of —S—, —Se—, —GeR$^x$R$^y$—, or —Te—, wherein $R^x$ and $R^y$ are the same or different and are independently one of hydrogen, a halogen, a substituted or unsubstituted C1 to C10 alkyl group, or a substituted or unsubstituted C6 to C10 aryl group, $R^{11}$ and $R^{12}$ may be the same or different and may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, and

* may be a linking point.

The cyclic group represented by Chemical Formula 2A may be for example a cyclic group represented by Chemical Formula 2A-1 or 2A-2.

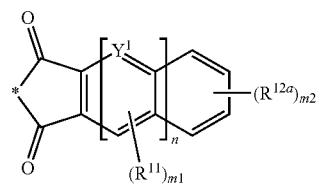

[Chemical Formula 2A-1]

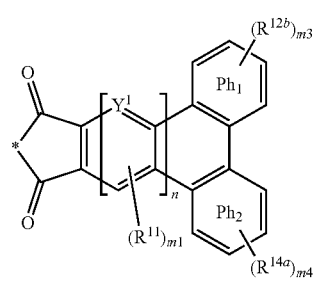

[Chemical Formula 2A-2]

In Chemical Formulae 2A-1 and 2A-2, $Y^1$, $R^{11}$, m1, and n are the same as in Chemical Formula 2A, $R^{12a}$, $R^{12b}$, and $R^{14a}$ may independently be one of hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m2, m3, and m4 may independently be an integer ranging from 0 to 4, and Ph1 and Ph2 denote a fused phenylene ring, provided that one of Ph1 and Ph2 may be optionally omitted.

The cyclic group represented by Chemical Formula 2B may be for example a cyclic group represented by Chemical Formula 2B-1, 2B-2, or 2B-3.

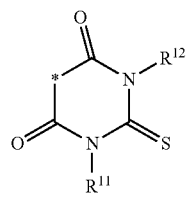

[Chemical Formula 2B-1]

[Chemical Formula 2B-2]

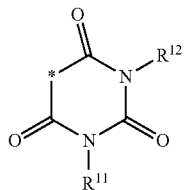

[Chemical Formula 2B-3]

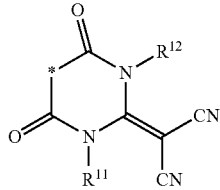

In Chemical Formulae 2B-1, 2B-2, and 2B-3, $R^{11}$ and $R^{12}$ are the same as in Chemical Formula 2B.

$Ar^1$ and $Ar^2$ of the N-containing hetero aromatic ring are linked by G and thereby provide one overall conjugation structure to improve thermal stability of the compound. Such a conjugation structure may be formed by fusing three to four 5-membered or 6-membered aromatic rings, but is not limited thereto.

$Ar^1$ and $Ar^2$ may independently be one of a substituted or unsubstituted C6 to C30 arene group, a substituted or unsubstituted C3 to C30 heteroarene group, or a combination thereof in a condensed ring that is formed by fusing aromatic rings. For example $Ar^1$ and $Ar^2$ may independently be one of a substituted or unsubstituted C6 to C20 arene group, a substituted or unsubstituted C3 to C20 heteroarene group, or a combination thereof in a condensed ring that is formed by fusing aromatic rings.

In some example embodiments, the arene group may be one of benzene, naphthalene, and anthracene and, the heteroarene group may be one of pyrrole, pyrazole, imidazole, oxazole, isoxazole, thiazole, isothiazole, pyridine, pyridazine, pyrimidine, pyrazine, indole, quinoline, isoquinoline, naphthyridine, cinnoline, quinazoline, phthalazine, benzotriazine, pyridopyrazine, pyridopyrimidine, pyridopyridazine, thiophene, benzothiiophene, selenophene or benzoselenophene.

In Chemical Formula 1, an intramolecular interaction between Te of the linker including the Te-containing 5-membered ring and oxygen (O) of a carbonyl group of the electron acceptor moiety may be increased and thereby an absorption intensity in a specific wavelength may be improved.

In the linker including the Te-containing 5-membered ring, $R^1$ and $R^2$ may independently be present or linked with each other to provide a ring. When they provides a ring, the linker may be represented by Chemical Formula 3A or Chemical Formula 3B.

[Chemical Formula 3A]

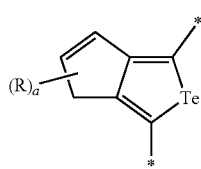

[Chemical Formula 3B]

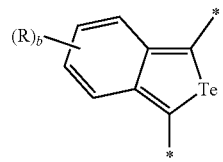

In Chemical Formula 3A and Chemical Formula 3B,

R may be one of hydrogen, a C1 to C10 alkyl group, a C6 to C10 aryl group, a C2 to C10 heteroaryl group, or a halogen, and a and b are independently an integer ranging from 1 to 4.

In Chemical Formula 1, at least one of $Ar^1$ and $Ar^2$ may include a heteroatom at No. 1 position, and the heteroatom may be one of nitrogen (N), sulfur (S), or selenium (Se). In this case, Te, oxygen (O) of a carbonyl group of the electron acceptor moiety, and the heteroatom at No. 1 position in at least one of $Ar^1$ and $Ar^2$ increase an intramolecular interaction and thereby improve an absorption intensity in a specific wavelength.

The electron donor moiety of the N-containing hetero aromatic ring in Chemical Formula 1 may be represented by Chemical Formula 4A.

[Chemical Formula 4A]

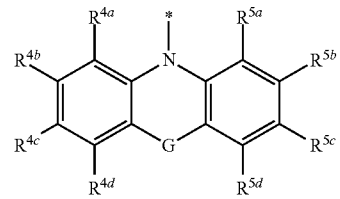

In Chemical Formula 4A, $R^{4a}$ to $R^{4d}$ and $R^{5a}$ to $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of $R^{4a}$ to $R^{4d}$ may be linked with each other to provide a 5-membered aromatic ring or a 6-membered aromatic ring, or two adjacent groups of $R^{5a}$ to $R^{5d}$ may be linked with each other to provide a 5-membered aromatic ring or a 6-membered aromatic ring, and G may be one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond (wherein R$^d$, R$^e$, R$^f$, R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure), and n in —(CR$^d$R$^e$)$_n$— is 1 or 2).

The ring structure formed by linking at least one pair of R$^{gg}$ and R$^{hh}$, R$^{ii}$ and R$^{jj}$, or R$^{mm}$ and R$^{nn}$ may be a spiro structure or a fused ring or for example a 5-membered or 6-membered ring structure. The ring structures may include at least one heteroatom of N, O, S, P, and Si therein.

In Chemical Formula 4A, when G is —SiR$^g$R$^h$—, —GeR$^i$R$^j$—, or —(C(R$^m$)=C(R$^n$))—, it may be represented by Chemical Formula 4A-1, Chemical Formula 4A-2, or Chemical Formula 4A-3.

[Chemical Formula 4A-1]

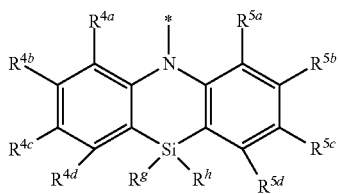

[Chemical Formula 4A-2]

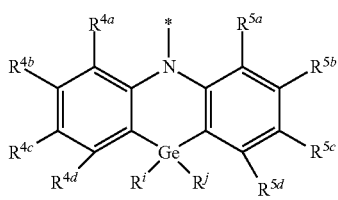

[Chemical Formula 4A-3]

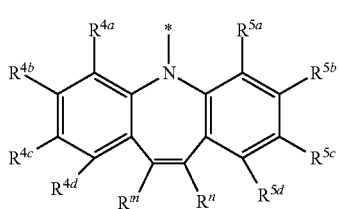

In Chemical Formula 4A-1, Chemical Formula 4A-2, or Chemical Formula 4A-3,

R$^{4a}$ to R$^{4d}$ and R$^{5a}$ to R$^{5d}$ are the same as in Chemical Formula 4A, and R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group.

In Chemical Formula 4A, when G is —SiR$^{gg}$R$^{hh}$—, —GeR$^{ii}$R$^{jj}$—, or —(C(R$^{mm}$)=C(R$^{nn}$))—, it may be represented by Chemical Formula 4AA-1, Chemical Formula 4AA-2, or Chemical Formula 4AA-3.

[Chemical Formula 4AA-1]

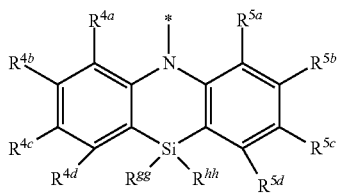

[Chemical Formula 4AA-2]

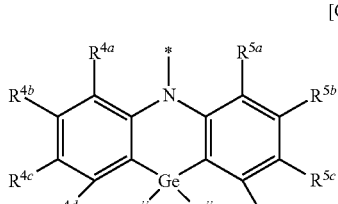

[Chemical Formula 4AA-3]

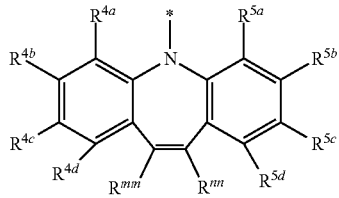

In Chemical Formula 4AA-1, Chemical Formula 4AA-2, or Chemical Formula 4AA-3,

R$^{4a}$ to R$^{4d}$ and R$^{5a}$ to R$^{5d}$ are the same as in Chemical Formula 4A, and R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure.

The ring structure formed by linking at least one pair of R$^{gg}$ and R$^{hh}$, R$^{ii}$ and R$^{jj}$, or R$^{mm}$ and R$^{nn}$ may be a spiro structure or a fused ring or for example a 5-membered or 6-membered ring structure. The ring structures may include at least one heteroatom of N, O, S, P, or Si therein.

The electron donor moiety of the N-containing hetero aromatic ring in Chemical Formula 1 may be represented by Chemical Formula 4B.

[Chemical Formula 4B]

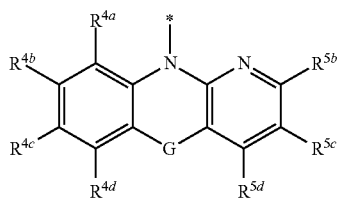

In Chemical Formula 4B,

R$^{4a}$ to R$^{4d}$ and R$^{5b}$ to R$^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{4a}$ to R$^{4d}$ may be linked with each other to provide a 5-membered aromatic ring or a 6-membered aromatic ring, or two adjacent groups of R$^{5b}$ to R$^{5d}$ may be linked with each other to provide a 5-membered aromatic ring or a 6-membered aromatic ring, and G may be one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nnn}$))—, or a single bond (wherein R$^d$, R$^e$, R$^f$, R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure, and n in —(CR$^d$R$^e$)$_n$— is 1 or 2).

The ring structure formed by linking at least one pair of R$^{gg}$ and R$^{hh}$, R$^{ii}$ and R$^{jj}$, or R$^{mm}$ and R$^{nn}$ may be a spiro structure or a fused ring or for example a 5-membered or 6-membered ring structure. The ring structures may include at least one heteroatom of N, O, S, P, or Si therein.

In Chemical Formula 4B, when G is —SiR$^g$R$^h$—, —GeR$^i$R$^j$—, or —(C(R$^m$)═C(R$^n$))—, it may be represented by Chemical Formula 4B-1, Chemical Formula 4B-2 or Chemical Formula 4B-3.

[Chemical Formula 4B-1]

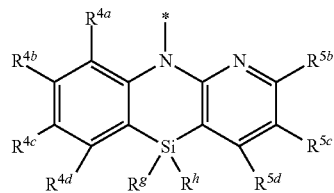

[Chemical Formula 4B-2]

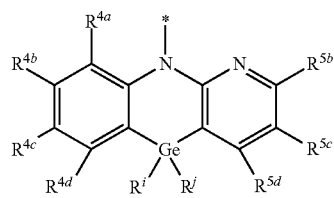

[Chemical Formula 4B-3]

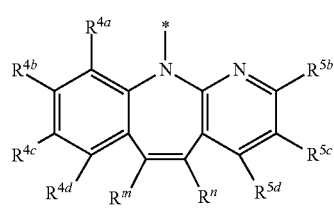

In Chemical Formula 4B-1, Chemical Formula 4B-2, or Chemical Formula 4B-3,

R$^{4a}$ to R$^{4d}$ and R$^{5b}$ to R$^{5d}$ are the same as in Chemical Formula 4B, and R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group.

In Chemical Formula 4B, when G is —SiR$^{gg}$R$^{hh}$—, —GeR$^{ii}$R$^{jj}$—, or —(C(R$^{mm}$)═C(R$^{nn}$))—, it may be represented by Chemical Formula 4BB-1, Chemical Formula 4BB-2, or Chemical Formula 4BB-3.

[Chemical Formula 4BB-1]

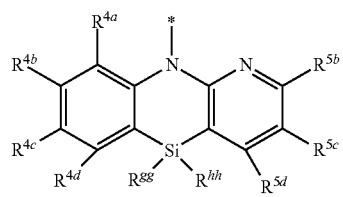

[Chemical Formula 4BB-2]

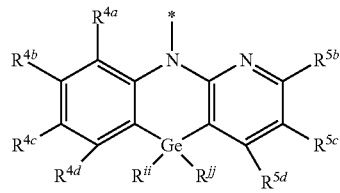

[Chemical Formula 4BB-3]

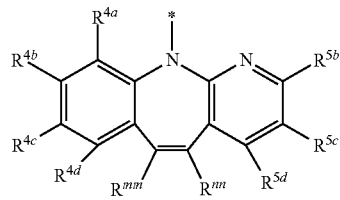

In Chemical Formula 4BB-2, Chemical Formula 4BB-2, or Chemical Formula 4BB-3,

R$^{4a}$ to R$^{4d}$ and R$^{5b}$ to R$^{5d}$ are the same as in Chemical Formula 4B, and R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure.

The ring structure formed by linking at least one pair of R$^{gg}$ and R$^{hh}$, R$^{ii}$ and R$^{jj}$, or R$^{mm}$ and R$^{nn}$ may be a spiro structure or a fused ring or for example a 5-membered or 6-membered ring structure. The ring structures may include at least one heteroatom of N, O, S, P, or Si therein. The electron donor moiety of the N-containing hetero aromatic ring in Chemical Formula 1 may be represented by Chemical Formula 4C.

[Chemical Formula 4C]

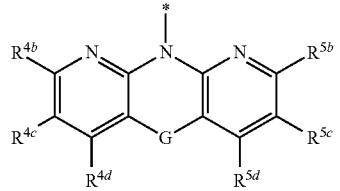

In Chemical Formula 4C,

R$^{4b}$ to R$^{4d}$ and R$^{5b}$ to R$^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{4b}$ to R$^{4d}$ may be linked with each other to provide a 5-membered aromatic ring or a 6-membered aromatic ring, or two adjacent groups of R$^{5b}$ to R$^{5d}$ may be linked with each other to provide a 5-membered aromatic ring or a 6-membered aromatic ring, and G may be one of —(CR$^d$R$^e$)$_n$—, —O—, —S—, —Se—, —N═, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)═C(R$^n$))—, —(C(R$^{mm}$)═C (R$^{nn}$))—, or a single bond (wherein R$^d$, R$^e$, R$^f$, R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure), and n in —$(CR^dR^e)_n$— is 1 or 2).

The ring structure formed by linking at least one pair of $R^{gg}$ and $R^{hh}$, $R^{ii}$ and $R^{jj}$, or $R^{mm}$ and $R^{nn}$ may be a spiro structure or a fused ring or for example a 5-membered or 6-membered ring structure. The ring structures may include at least one heteroatom of N, O, S, P, or Si therein.

In Chemical Formula 4C, when G is —$SiR^gR^h$—, —$GeR^iR^j$—, or —$(C(R^m)=C(R^n))$—, it may be represented by Chemical Formula 4C-1, Chemical Formula 4C-2, or Chemical Formula 4C-3.

[Chemical Formula 4C-1]

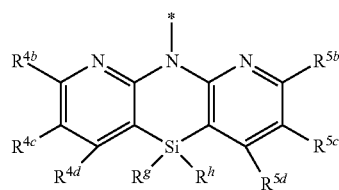

[Chemical Formula 4C-2]

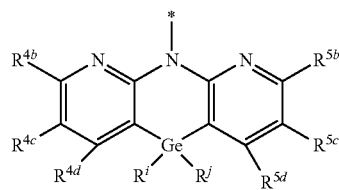

[Chemical Formula 4C-3]

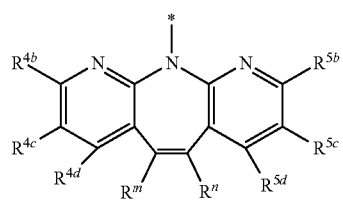

In Chemical Formula 4C-1, Chemical Formula 4C-2, or Chemical Formula 4C-3, $R^{4b}$ to $R^{4d}$ and $R^{5b}$ to $R^{5d}$ are the same as in Chemical Formula 4C, and $R^g$, $R^h$, $R^i$, $R^j$, $R^m$, and $R^n$ may independently be one of hydrogen, a halogen, a substituted or unsubstituted C1 to C10 alkyl group, or a substituted or unsubstituted C6 to C10 aryl group.

In Chemical Formula 4C, when G is —$SiR^{gg}R^{hh}$—, —$GeR^{ii}R^{jj}$—, or —$(C(R^{mm})=C(R^{nn}))$—, it may be represented by Chemical Formula 4CC-1, Chemical Formula 4CC-2, or Chemical Formula 4CC-3.

[Chemical Formula 4CC-1]

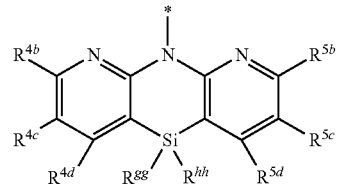

[Chemical Formula 4CC-2]

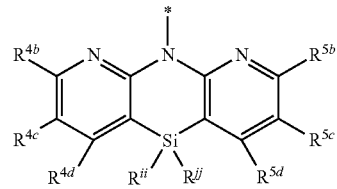

[Chemical Formula 4CC-3]

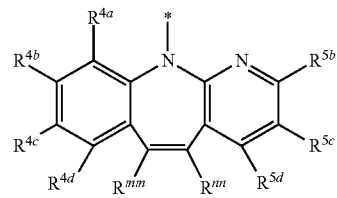

In Chemical Formula 4CC-1, Chemical Formula 4CC-2, or Chemical Formula 4CC-3, $R^{4b}$ to $R^{4d}$ and $R^{5b}$ to $R^{5d}$ are the same as in Chemical Formula 4C, and $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure.

The ring structure formed by linking at least one pair of $R^{gg}$ and $R^{hh}$, $R^{ii}$ and $R^{jj}$, or $R^{mm}$ and $R^{nn}$ may be a spiro structure or a fused ring or for example a 5-membered or 6-membered ring structure. The ring structures may include at least one heteroatom of N, O, S, P, or Si therein.

The electron donor moiety of the N-containing hetero aromatic ring in Chemical Formula 1 may be represented by Chemical Formula 4D.

[Chemical Formula 4D]

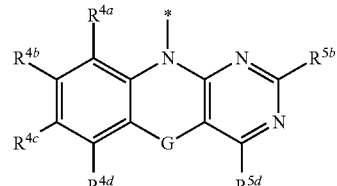

In Chemical Formula 4D, $R^{4a}$ to $R^{4d}$ and $R^{5b}$ and $R^{5d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of $R^{4a}$ to $R^{4d}$ may be linked with each other to provide a 5-membered aromatic ring or a 6-membered aromatic ring, and G may be one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond (wherein R$^d$, R$^e$, R$^f$, R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure), and n in —(CR$^d$R$^e$)$_n$— is 1 or 2).

The ring structure formed by linking at least one pair of R$^{gg}$, R$^{hh}$, R$^{ii}$, R$^{jj}$, R$^{mm}$, and R$^{nn}$ may be a spiro structure or a fused ring or for example a 5-membered or 6-membered ring structure. The ring structures may include at least one heteroatom of N, O, S, P, or Si therein.

In Chemical Formula 4D, when G is —SiR$^g$R$^h$—, —GeR$^i$R$^j$—, or —(C(R$^m$)=C(R$^n$))—, it may be represented by Chemical Formula 4D-1, Chemical Formula 4D-2, or Chemical Formula 4D-3.

[Chemical Formula 4D-1]

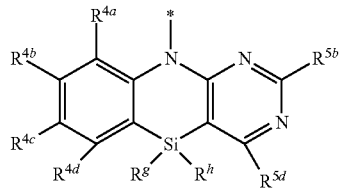

[Chemical Formula 4D-2]

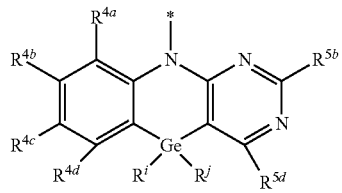

[Chemical Formula 4D-3]

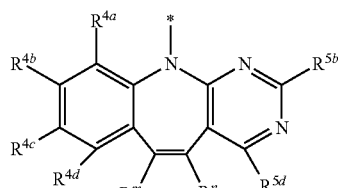

In Chemical Formula 4D-1, Chemical Formula 4D-2, or Chemical Formula 4D-3,

R$^{4a}$ to R$^{4d}$ and R$^{5b}$ and R$^{5d}$ are the same as in Chemical Formula 4D, and R$^g$, R$^h$, R$^i$, R$^j$, R$^m$, and R$^n$ may independently be one of hydrogen, a halogen, a substituted or unsubstituted C1 to C10 alkyl group, or a substituted or unsubstituted C6 to C10 aryl group.

In Chemical Formula 4D, when G is —SiR$^{gg}$R$^{hh}$—, —GeR$^{ii}$R$^{jj}$—, or —(C(R$^{mm}$)=C(R$^{nn}$))—, it may be represented by Chemical Formula 4DD-1, Chemical Formula 4DD-2, or Chemical Formula 4DD-3.

[Chemical Formula 4DD-1]

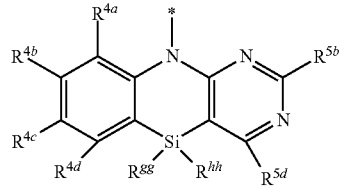

[Chemical Formula 4DD-2]

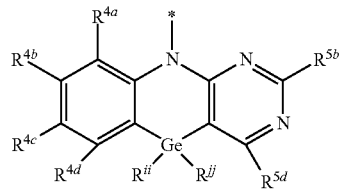

[Chemical Formula 4DD-3]

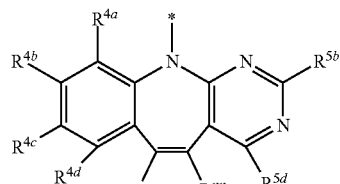

In Chemical Formula 4DD-1, Chemical Formula 4DD-2, or Chemical Formula 4DD-3,

R$^{4a}$ to R$^{4d}$ and R$^{5b}$ and R$^{5d}$ are the same as in Chemical Formula 4D, and R$^{gg}$, R$^{hh}$, R$^{ii}$, R$^{jj}$, R$^{mm}$, and R$^{nn}$ may independently be one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ may be linked with each other to provide a ring structure.

The ring structure formed by linking at least one pair of R$^{gg}$ and R$^{hh}$, R$^{ii}$ and R$^{jj}$, or R$^{mm}$ and R$^{nn}$ may be a spiro structure or a fused ring or for example a 5-membered or 6-membered ring structure. The ring structures may include at least one heteroatom of N, O, S, P, and Si therein.

The electron donor moiety of the N-containing hetero aromatic ring in Chemical Formula 1 may be represented by Chemical Formula 4E.

[Chemical Formula 4E]

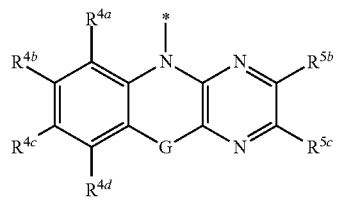

In Chemical Formula 4E,

R$^{4a}$ to R$^{4d}$ and R$^{5b}$ and R$^{5c}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, two adjacent groups of R$^{4a}$ to R$^{4d}$ may be linked with each other to provide a 5-membered aromatic ring or a 6-membered aromatic ring, or two adjacent groups of $R^{5b}$ and $R^{5c}$ may be linked with each other to provide a 5-membered aromatic ring or a 6-membered aromatic ring, and G may be one of —$(CR^dR^e)_n$—, —O—, —S—, —Se—, —N=, —$NR^f$—, —$SiR^gR^h$—, —$SiR^{gg}R^{hh}$—, —$GeR^iR^j$—, —$GeR^{ii}R^{jj}$—, —$(C(R^m)=C(R^n))$—, —$(C(R^{mm})=C(R^{nn}))$—, or a single bond (wherein $R^d$, $R^e$, $R^f$, $R^g$, $R^h$, $R^i$, $R^j$, $R^m$, and $R^n$ may independently be one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure), and n in —$(CR^dR^e)_n$— is 1 or 2).

The ring structure formed by linking at least one pair of $R^{gg}$ and $R^{hh}$, $R^{ii}$ and $R^{jj}$, or $R^{mm}$ and $R^{nn}$ may be a spiro structure or a fused ring or for example a 5-membered or 6-membered ring structure. The ring structures may include at least one heteroatom of N, O, S, P, or Si therein.

In Chemical Formula 4E, when G is —$SiR^gR^h$—, —$GeR^iR^j$—, or —$(C(R^m)=C(R^n))$—, it may be represented by Chemical Formula 4E-1, Chemical Formula 4E-2, or Chemical Formula 4E-3.

[Chemical Formula 4E-1]

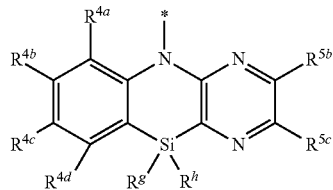

[Chemical Formula 4E-2]

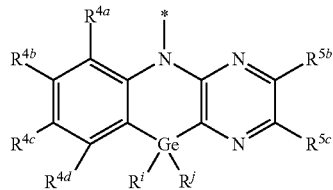

[Chemical Formula 4E-3]

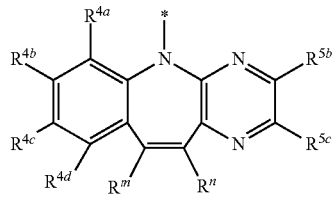

In Chemical Formula 4E-1, Chemical Formula 4E-2, or Chemical Formula 4E-3, $R^{4a}$ to $R^{4d}$ and $R^{5b}$ and $R^{5c}$ are the same as in Chemical Formula 4E, and $R^g$, $R^h$, $R^i$, $R^j$, $R^m$, and $R^n$ may independently be one of hydrogen, a halogen, a substituted or unsubstituted C1 to C10 alkyl group, or a substituted or unsubstituted C6 to C10 aryl group.

In Chemical Formula 4E, when G is —$SiR^{gg}R^{hh}$—, —$GeR^{ii}R^{jj}$—, or —$(C(R^{mm})=C(R^{nn}))$—, it may be represented by Chemical Formula 4EE-1, Chemical Formula 4EE-2, or Chemical Formula 4EE-3.

[Chemical Formula 4EE-1]

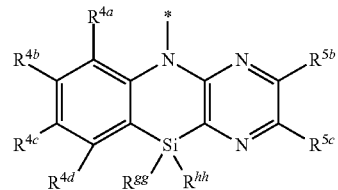

[Chemical Formula 4EE-2]

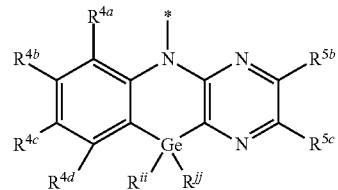

[Chemical Formula 4EE-3]

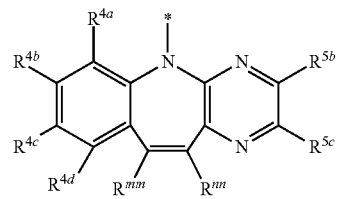

In Chemical Formula 4EE-1, Chemical Formula 4EE-2, or Chemical Formula 4EE-3, $R^{4a}$ to $R^{4d}$ and $R^{5b}$ and $R^{5c}$ are the same as in Chemical Formula 4E, and $R^{gg}$, $R^{hh}$, $R^{ii}$, $R^{jj}$, $R^{mm}$, and $R^{nn}$ may independently be one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ may be linked with each other to provide a ring structure.

The ring structure formed by linking at least one pair of $R^{gg}$ and $R^{hh}$, $R^{ii}$ and $R^{jj}$, or $R^{mm}$ and $R^{nn}$ may be a spiro structure or a fused ring or for example a 5-membered or 6-membered ring structure. The ring structures may include at least one heteroatom of N, O, S, P, or Si therein.

Specific examples of the compound represented by Chemical Formula 1 may be one of compounds of Chemical Formula 5A, Chemical Formula 5B, Chemical Formula 5C, Chemical Formula 5D, and Chemical Formula 5E, but are not limited thereto.

[Chemical Formula 5A]

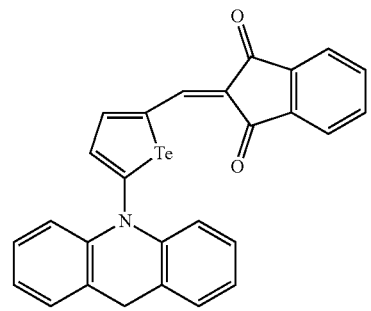

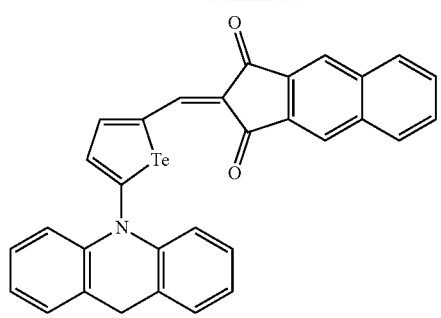
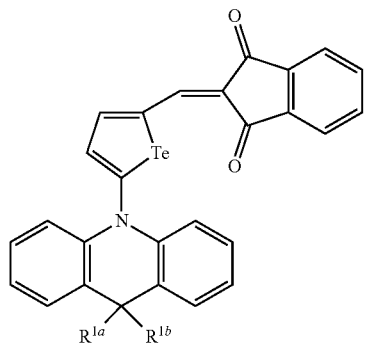
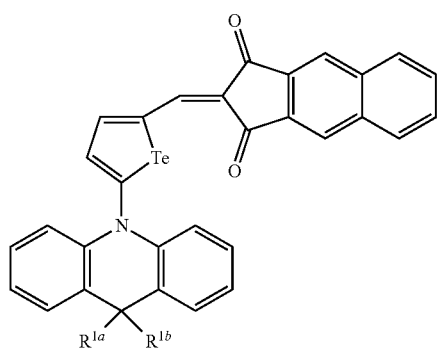
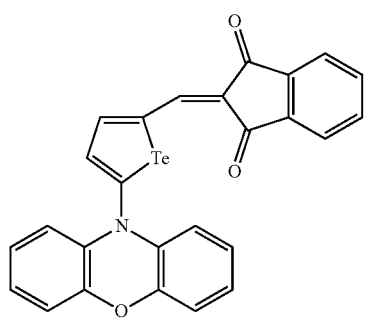
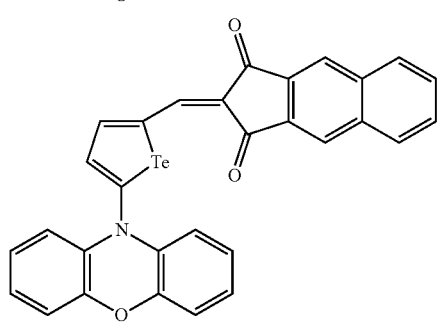
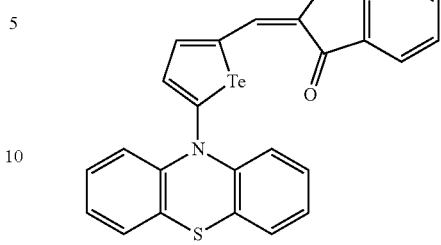
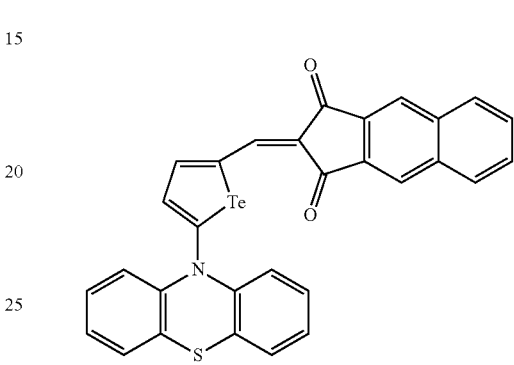
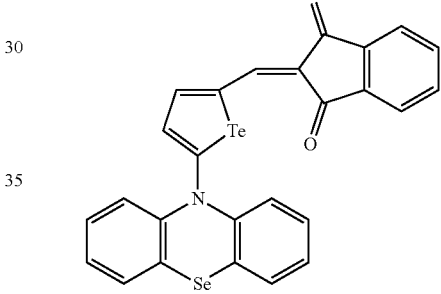
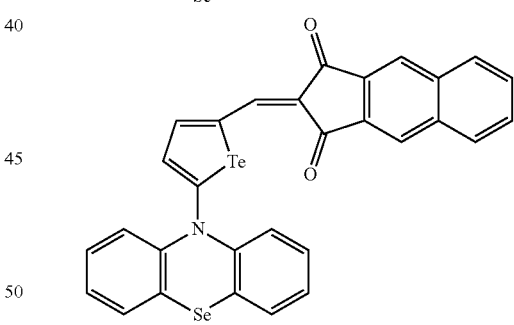
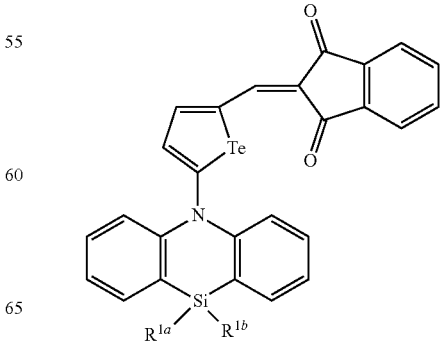

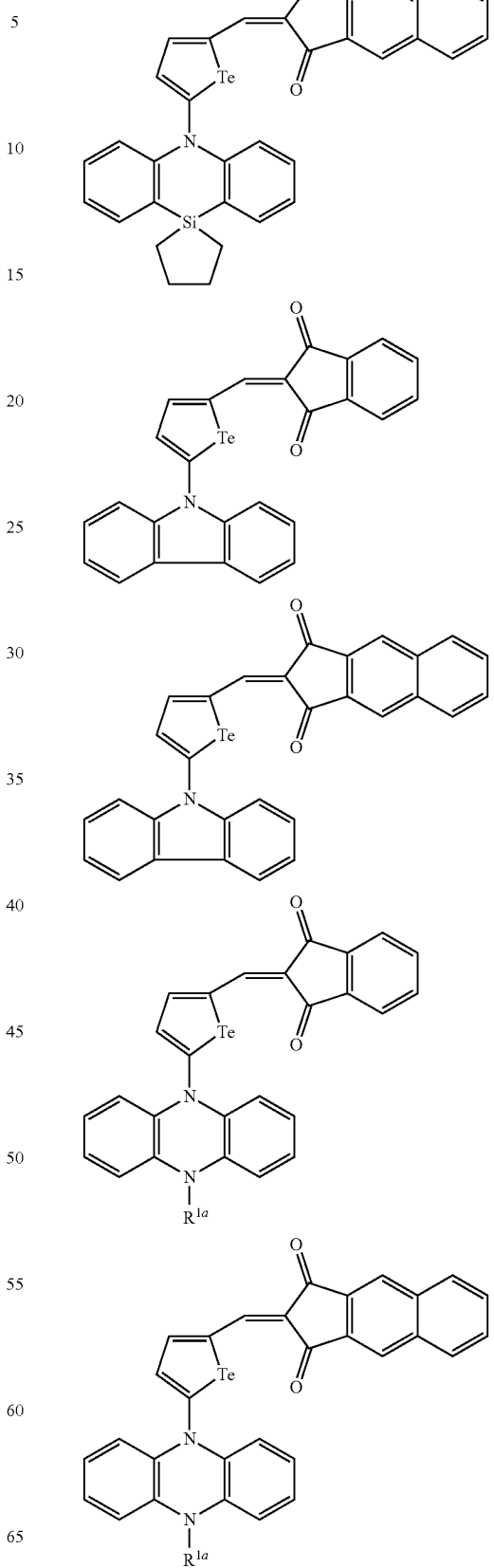

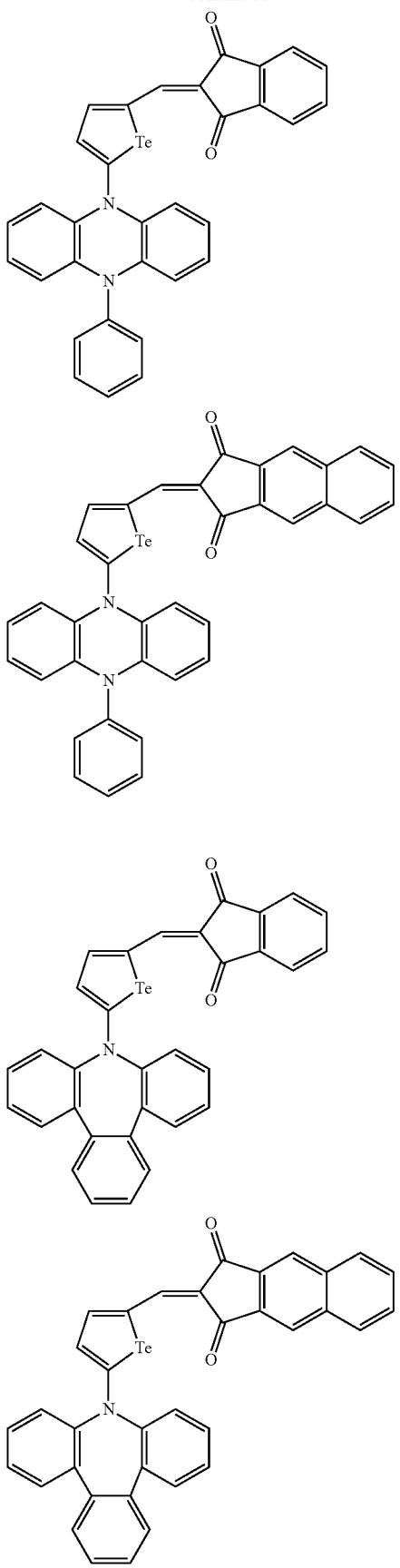
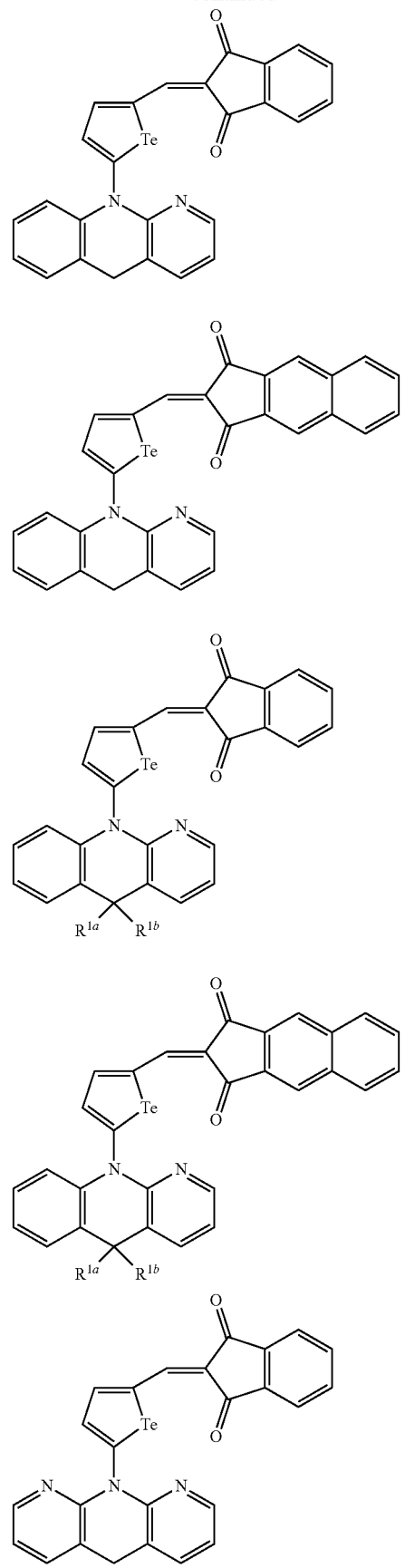

31
-continued
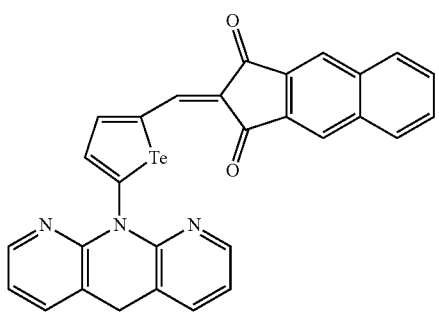
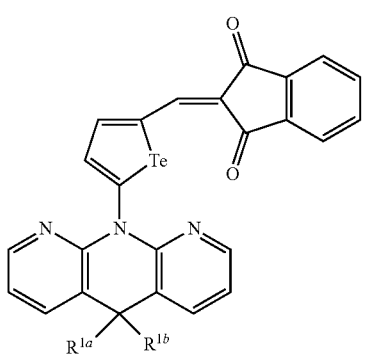
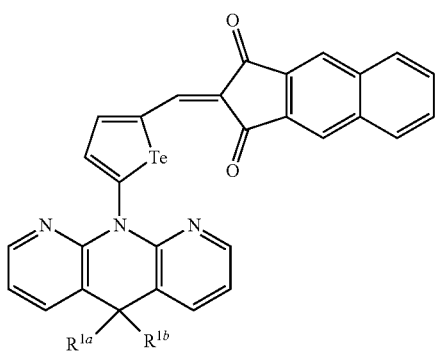
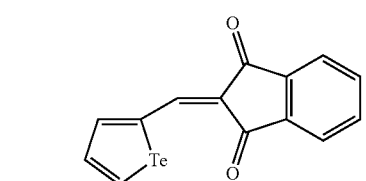
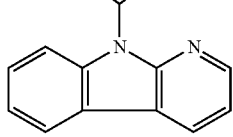
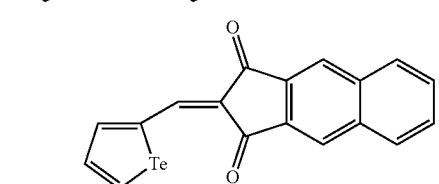
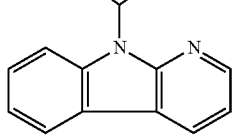
32
-continued
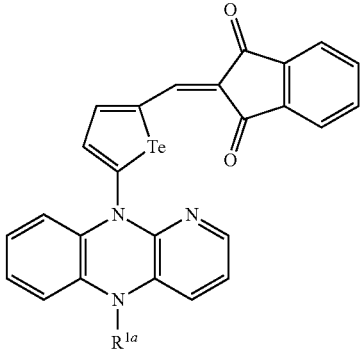
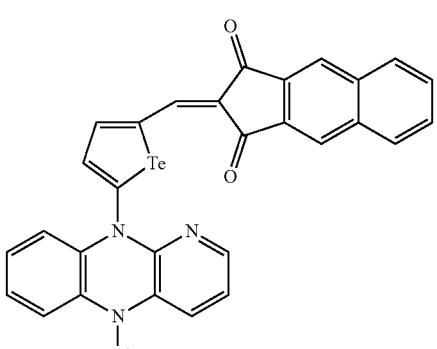
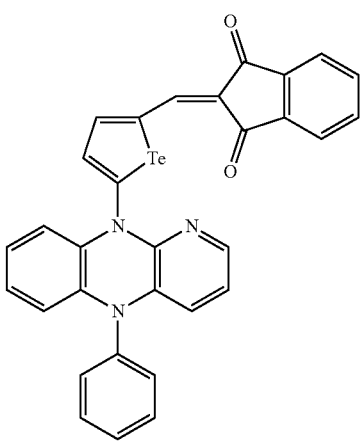
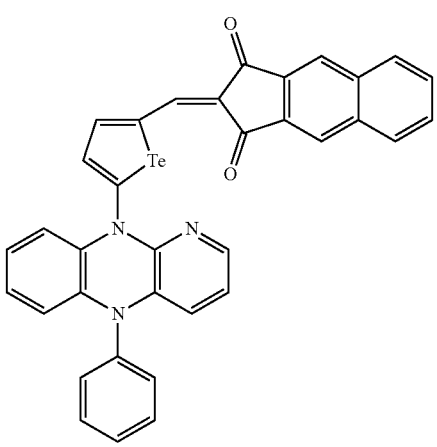

33
-continued
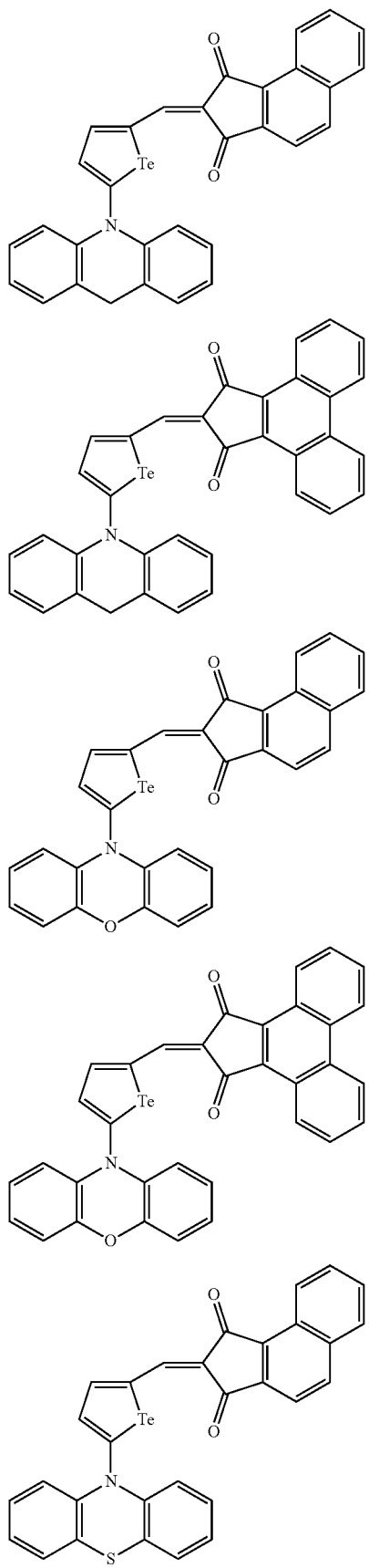
34
-continued
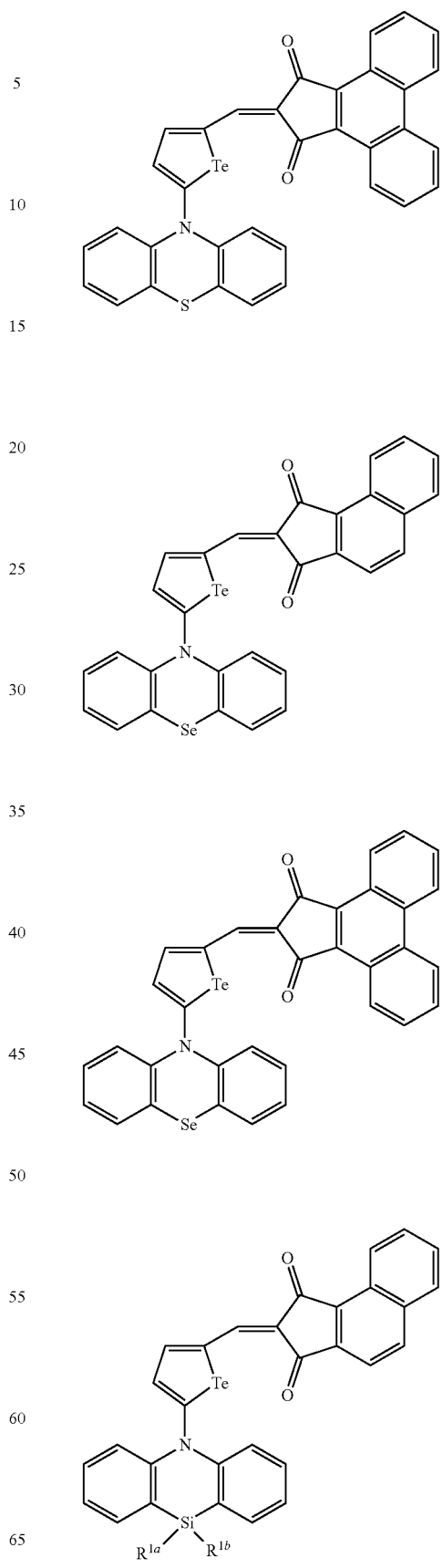

-continued

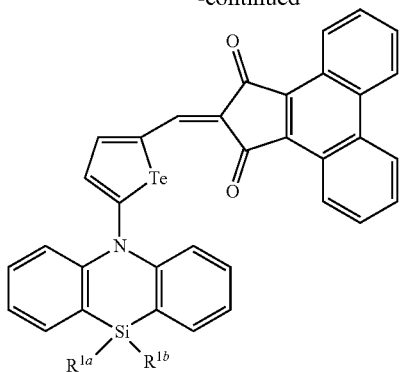

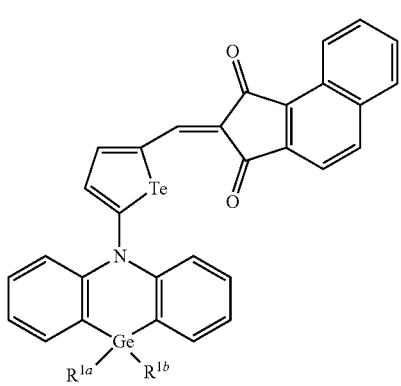

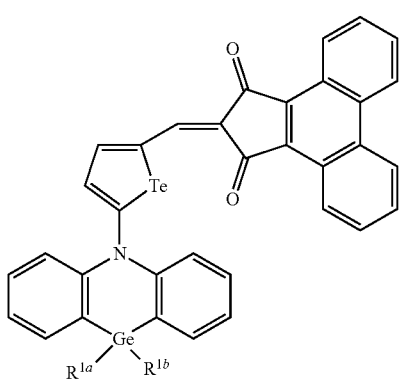

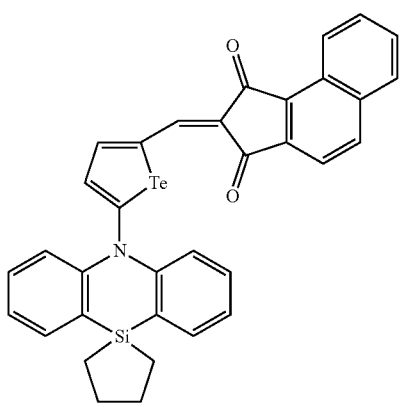

-continued

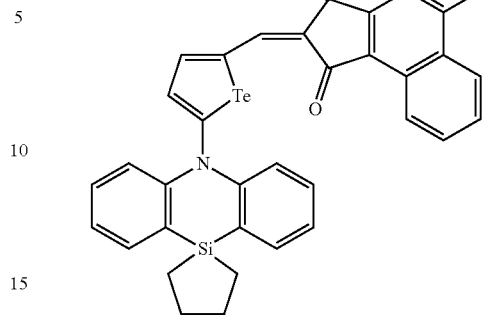

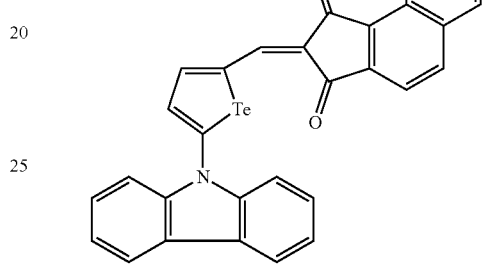

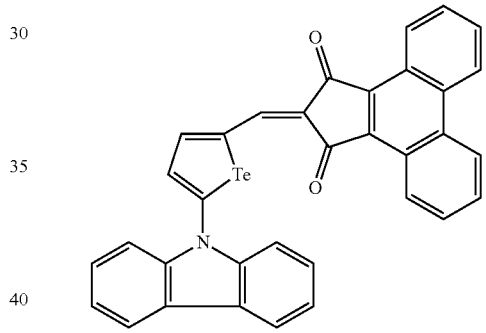

In Chemical Formula 5A,
hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and a combination thereof, and $R^{1a}$ and $R^{1b}$ may independently be a C1 to C6 alkyl group.

[Chemical Formula 5B]

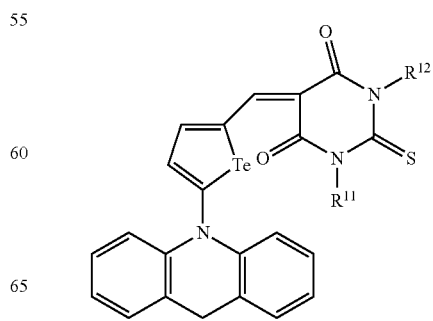

-continued
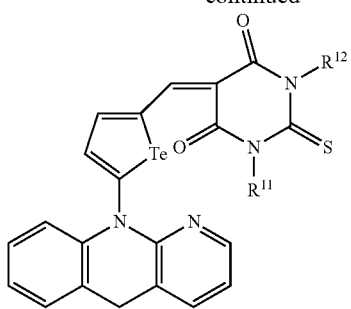
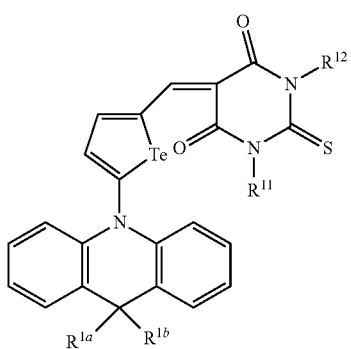
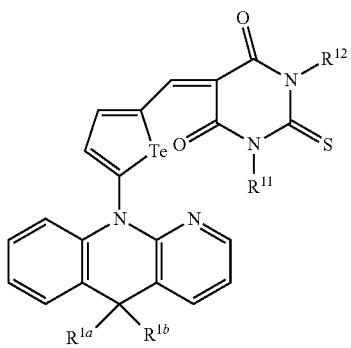
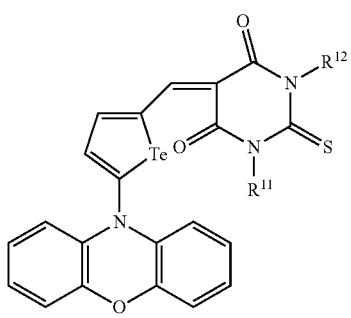
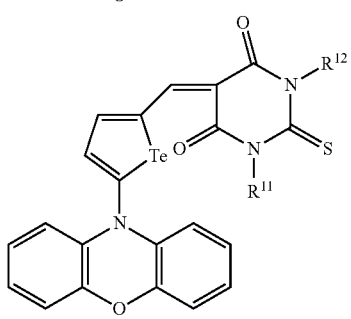
-continued
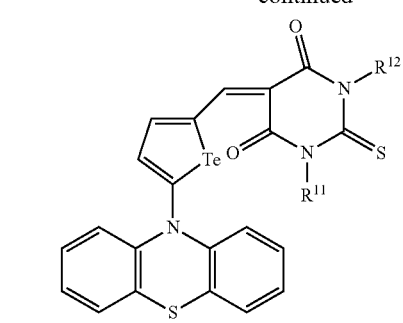
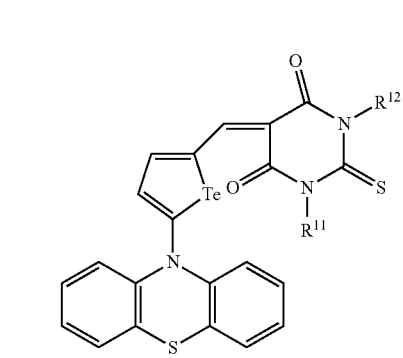
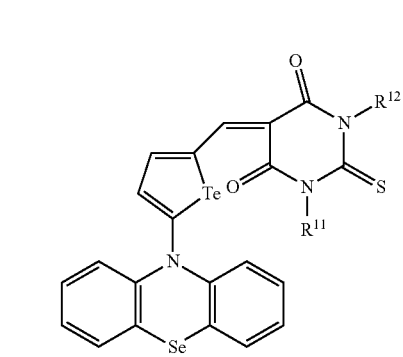
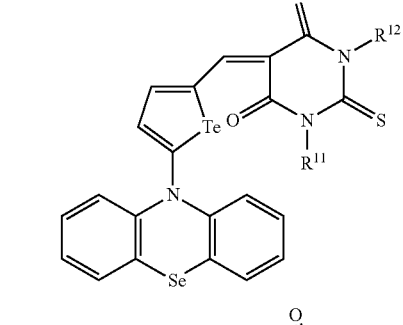
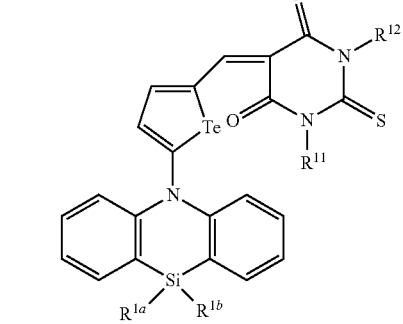

39
-continued
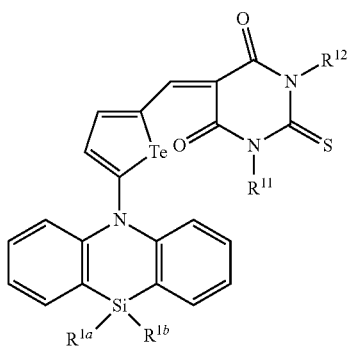
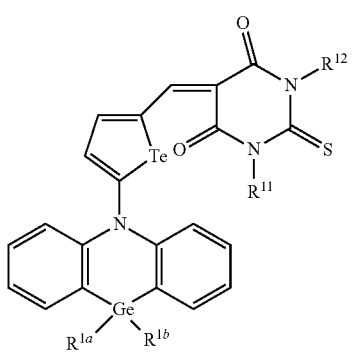
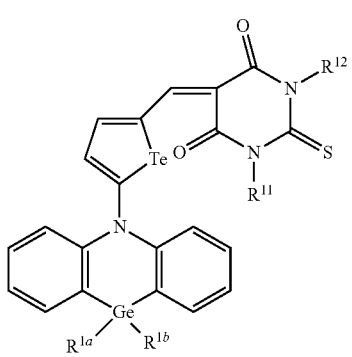
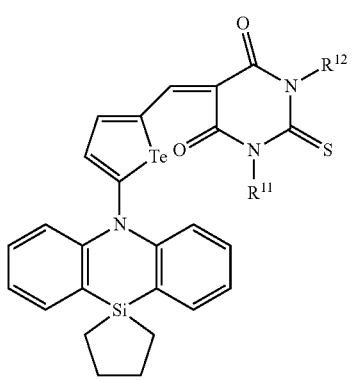
40
-continued
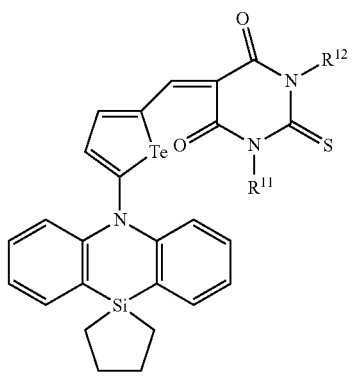
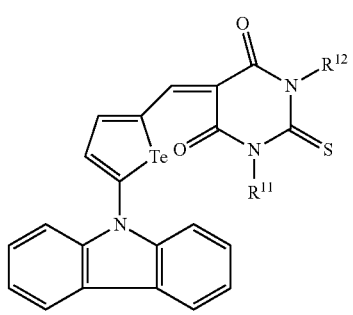
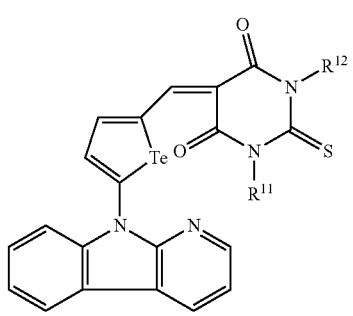
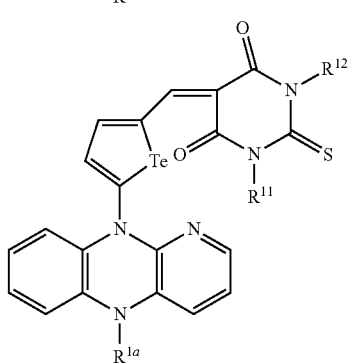

-continued

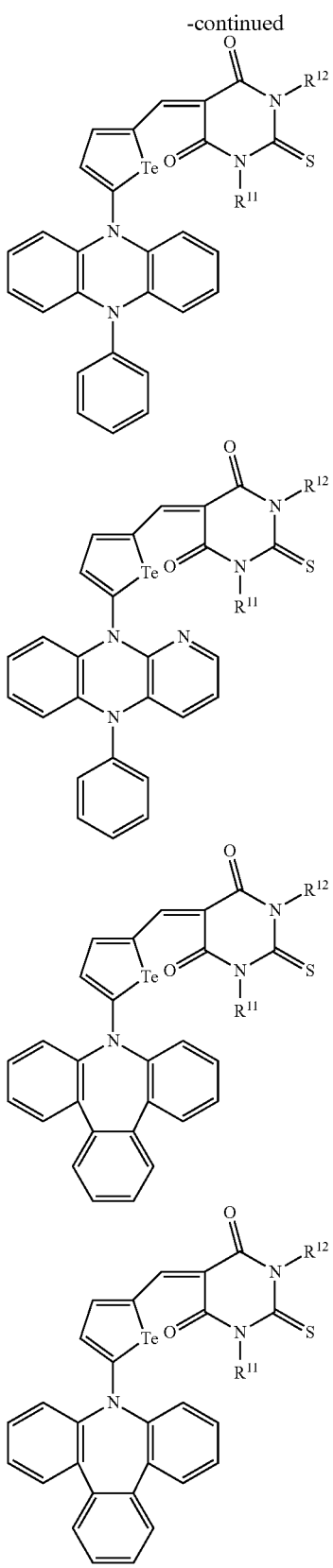

In Chemical Formula 5B,
R$^{11}$ and R$^{12}$ are the same as in Chemical Formula 2B, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and R$^{1a}$ and R$^{1b}$ may independently be a C1 to C6 alkyl group.

[Chemical Formula 5C]

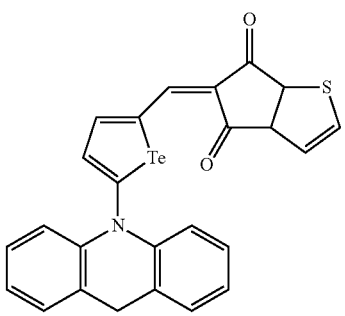

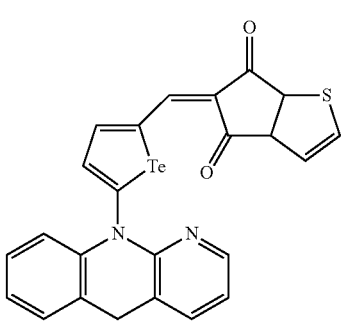

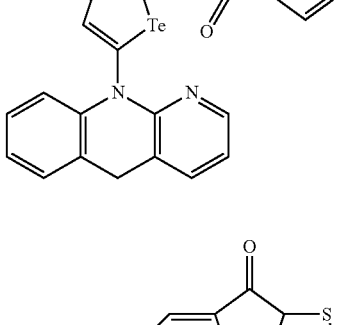

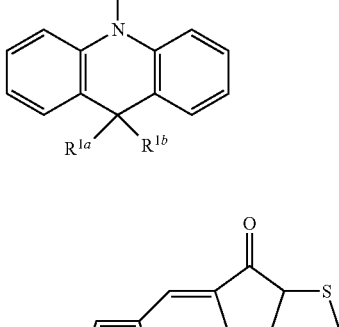

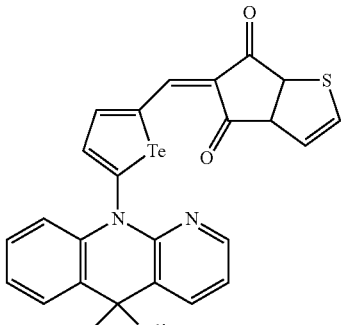

-continued
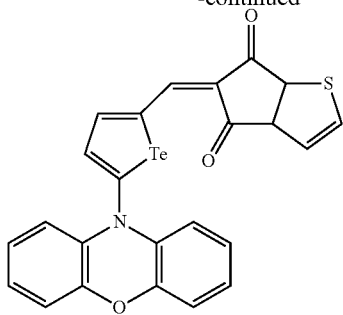
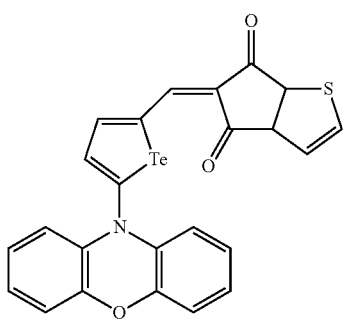
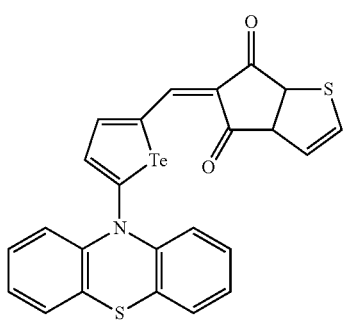
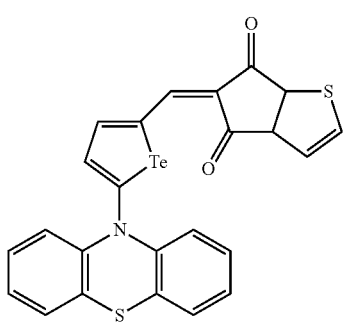
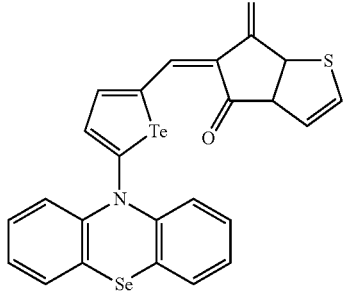
-continued
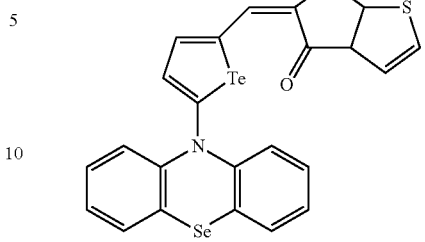
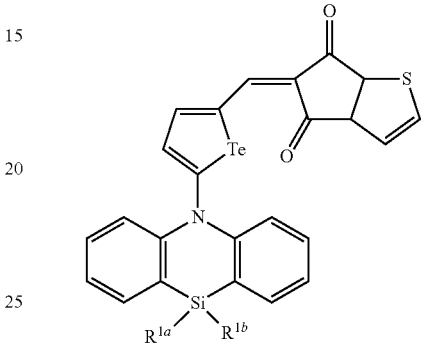
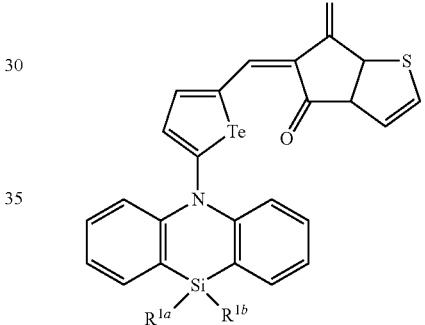
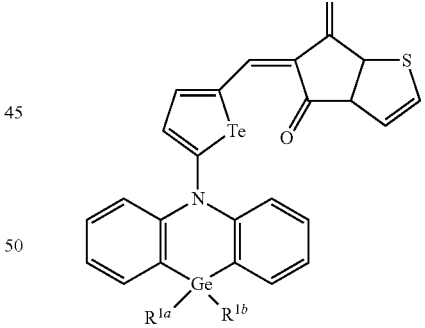
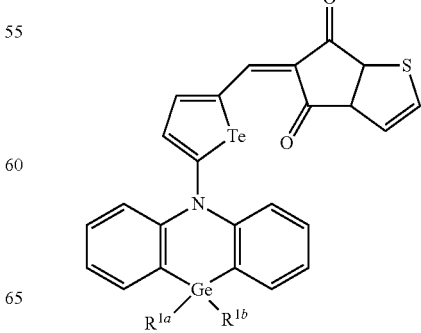

-continued
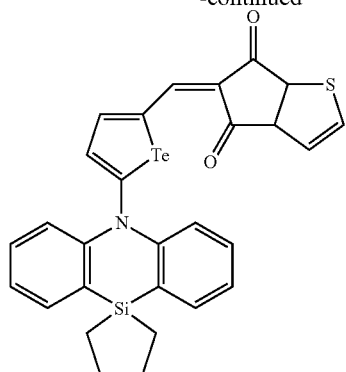
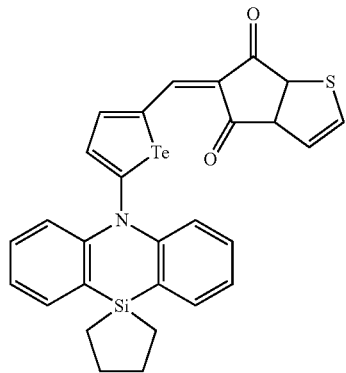
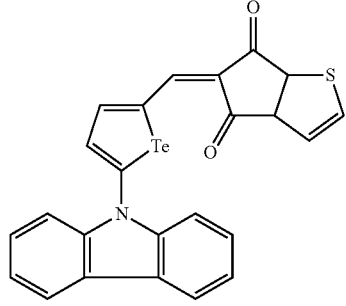
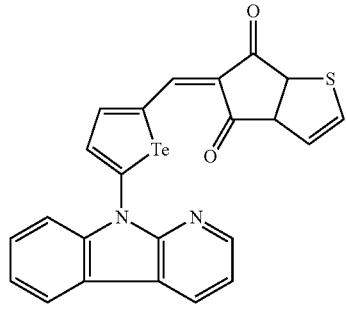
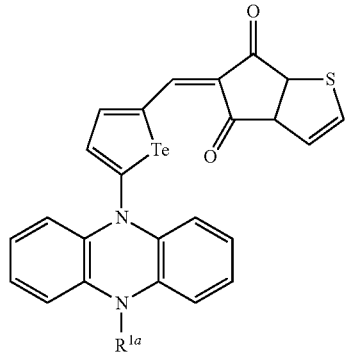
-continued
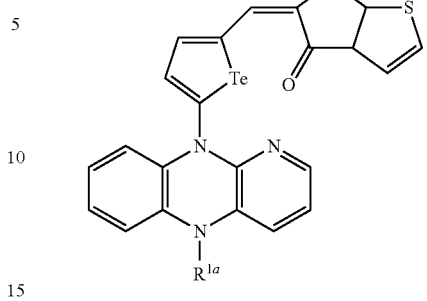
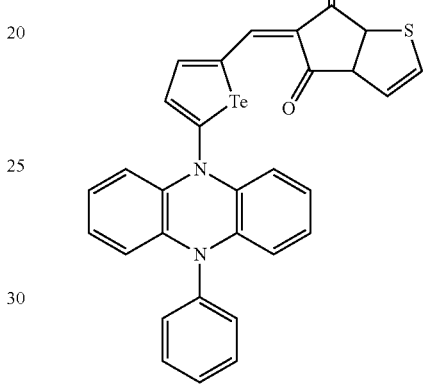
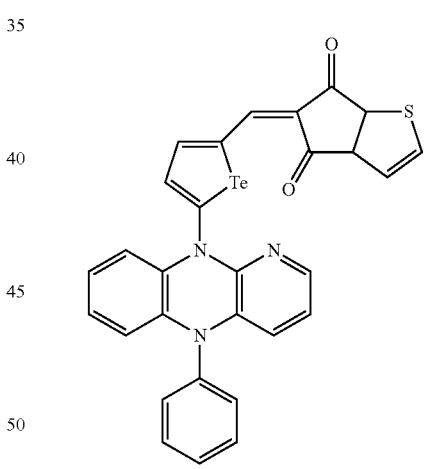
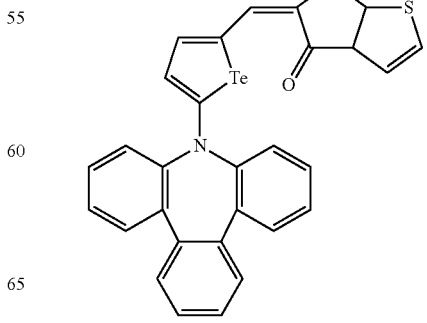

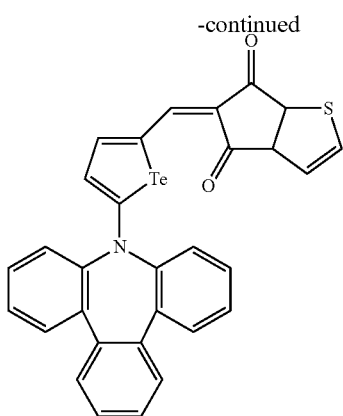

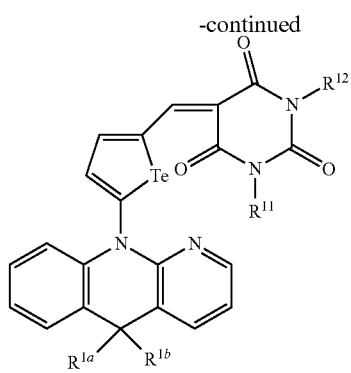

In Chemical Formula 5C, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and $R^{1a}$ and $R^{1b}$ may independently be a C1 to C6 alkyl group.

[Chemical Formula 5D]

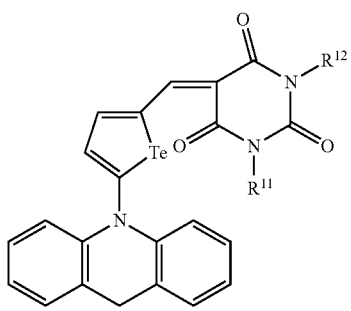

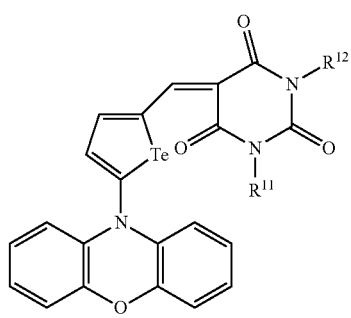

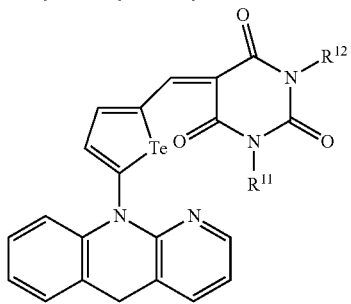

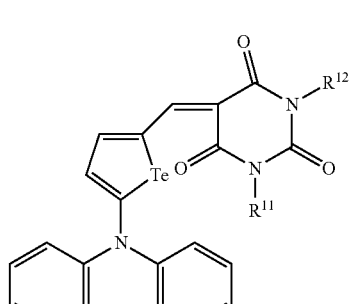

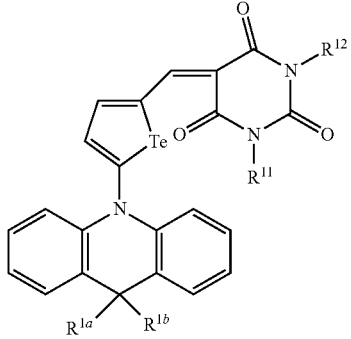

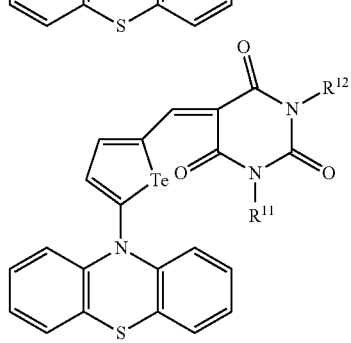

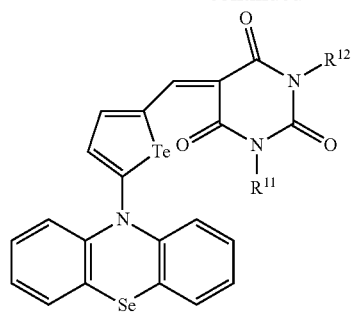
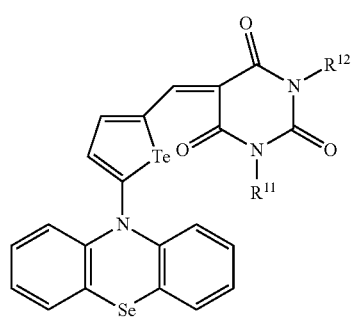
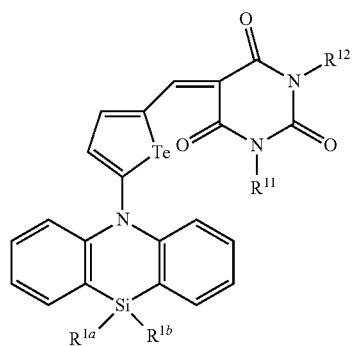
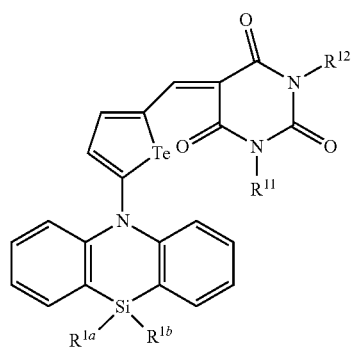
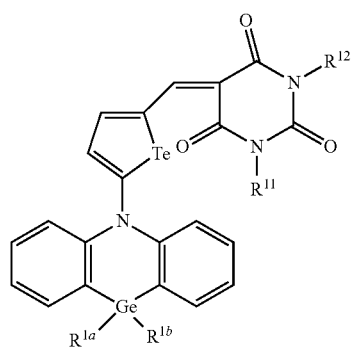
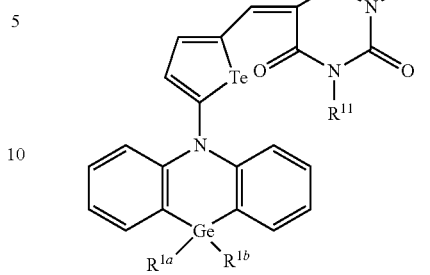
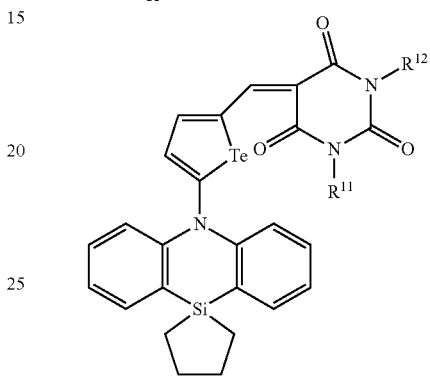
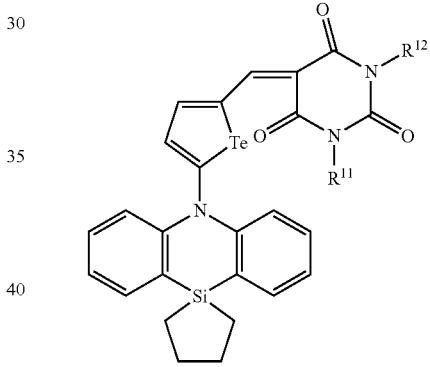
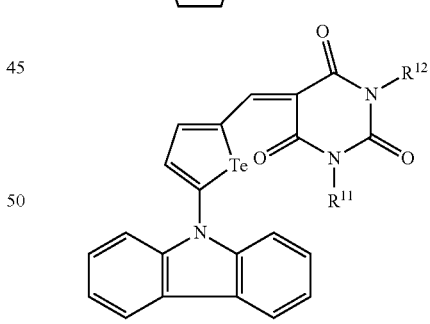
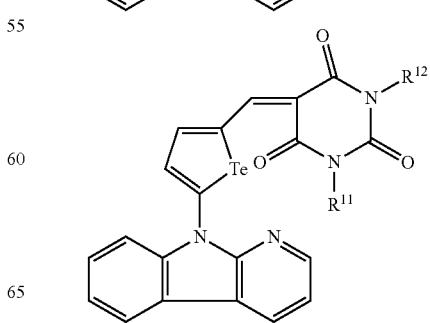

-continued

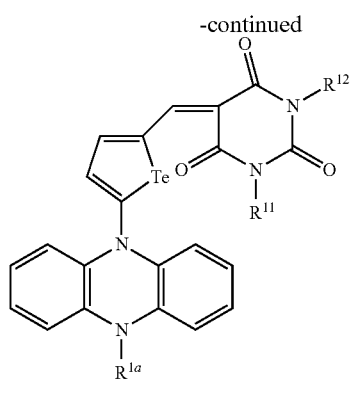

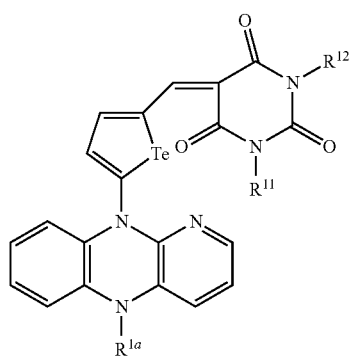

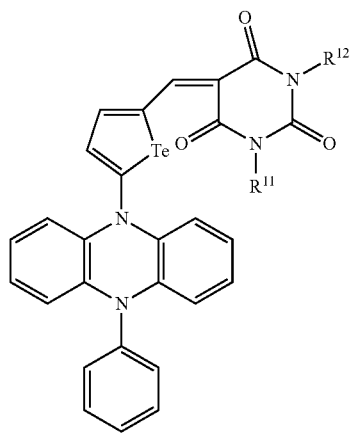

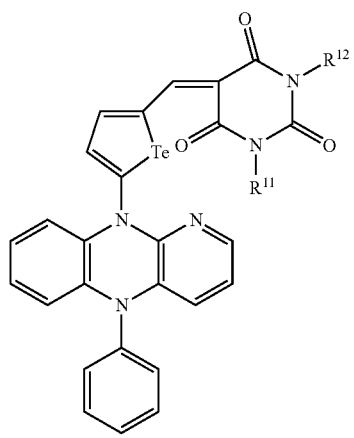

-continued

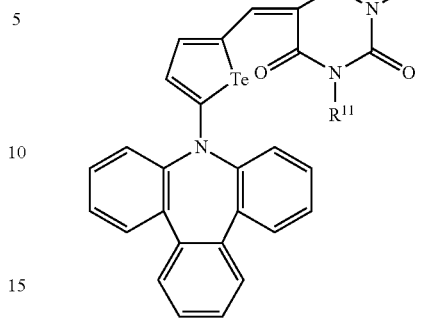

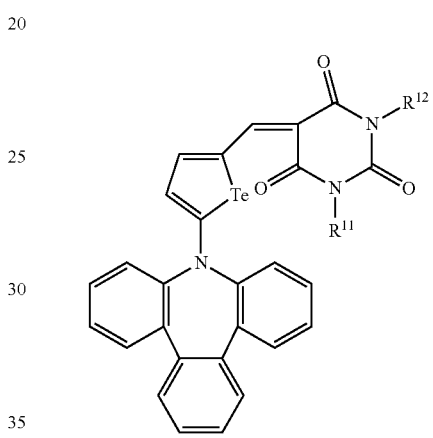

In Chemical Formula 5D, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and $R^{1a}$ and $R^{1b}$ may independently be a C1 to C6 alkyl group.

[Chemical Formula 5E]

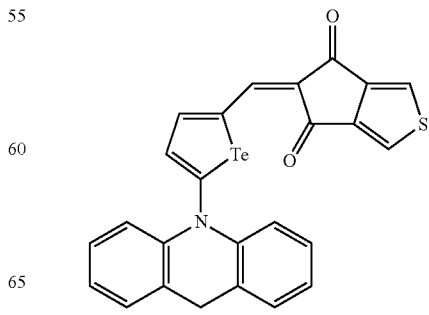

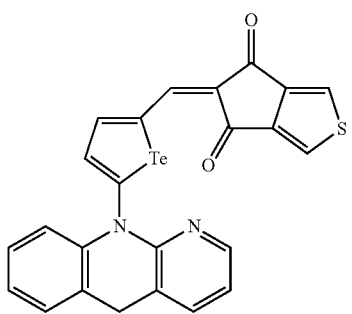
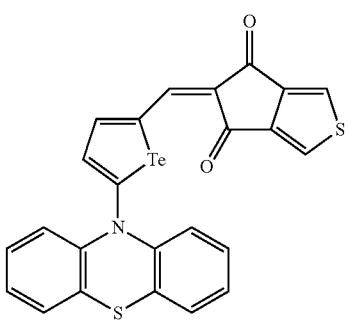
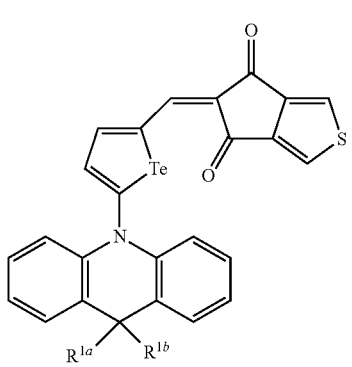
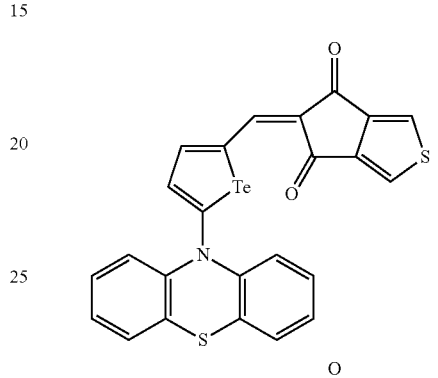
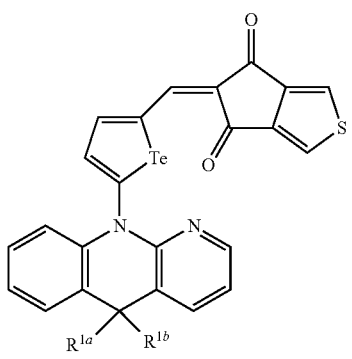
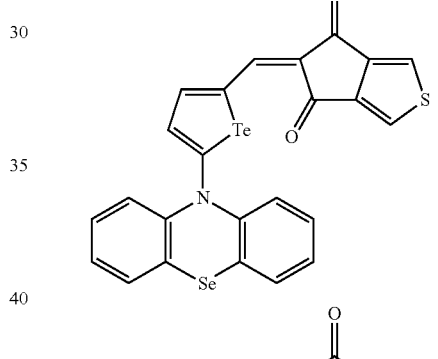
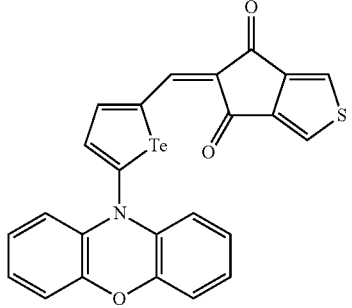
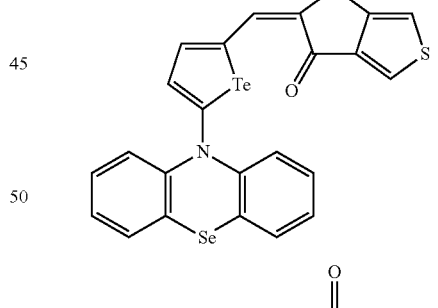
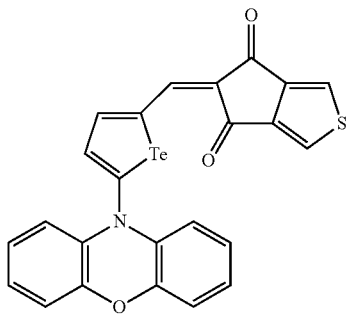
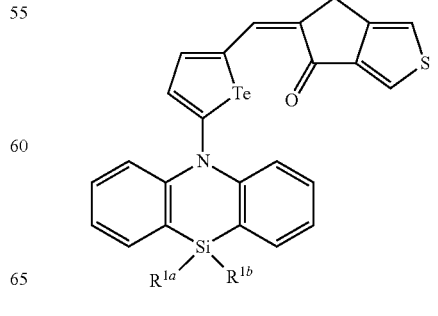

55
-continued
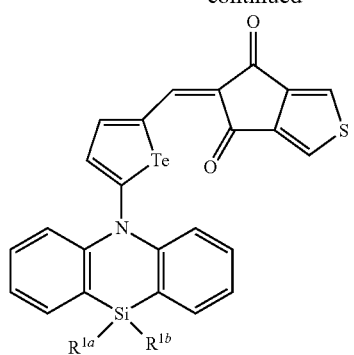
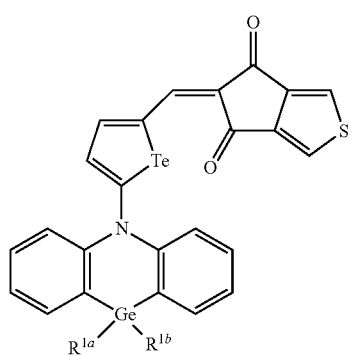
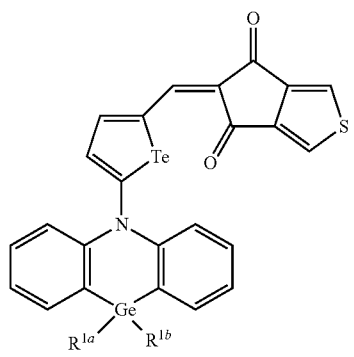
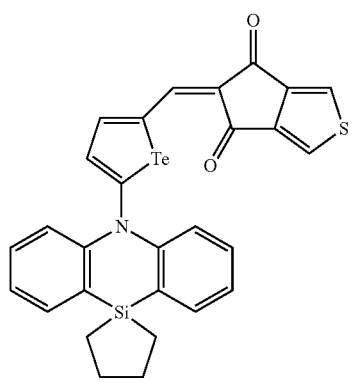
56
-continued
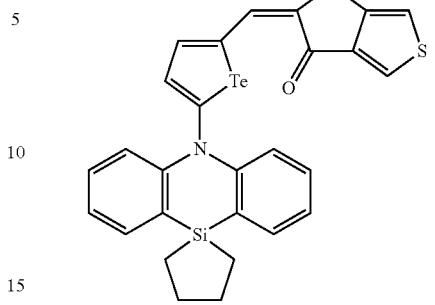
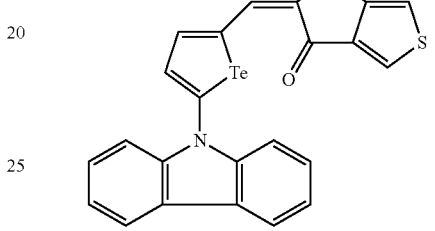
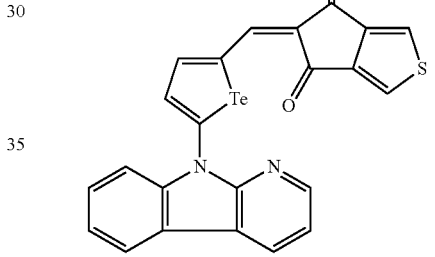
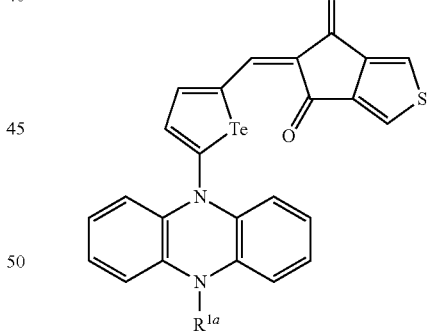
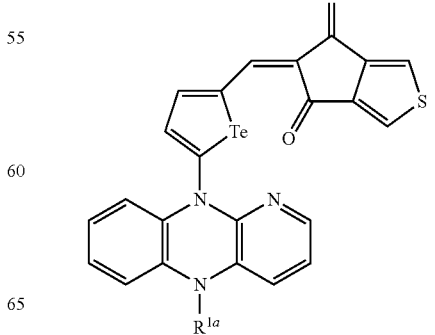

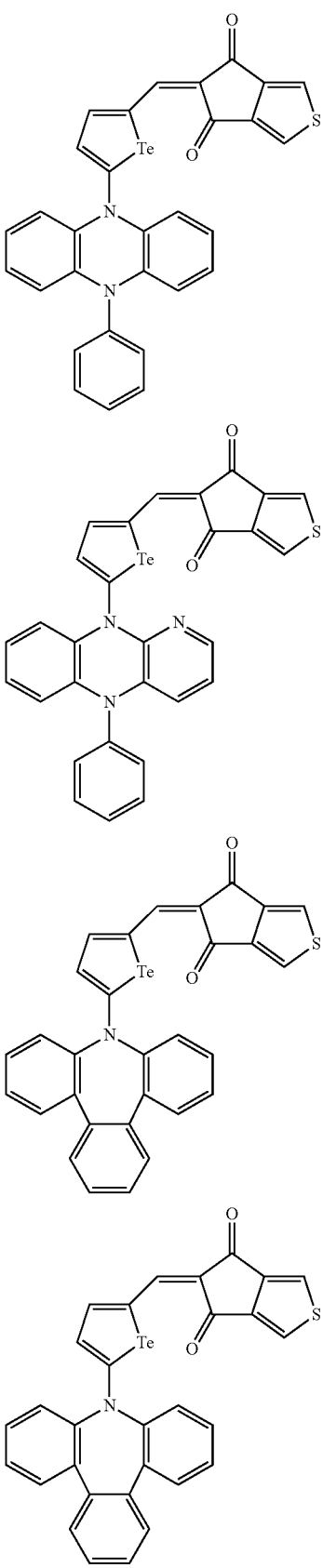

In Chemical Formula 5E, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof, and $R^{1a}$ and $R^{1b}$ may independently be a C1 to C6 alkyl group.

The compound is a compound selectively absorbing light in a green wavelength region, and may have a maximum absorption wavelength ($\lambda_{max}$) in a wavelength region of greater than or equal to about 500 nm to about 600 nm, for example greater than or equal to about 530 nm, greater than or equal to about 535 nm, or greater than or equal to about 540 nm and less than or equal to about 590 nm, or less than or equal to about 580 nm.

The compound may exhibit a light absorption curve having a full width at half maximum (FWHM) of about 50 nm to about 130 nm, for example about 50 nm to about 120 nm in a thin film state. Herein, the FWHM is a width of a wavelength corresponding to half of a height of a maximum absorption point. When the full width at half maximum (FWHM) is small, wavelength selectivity is increased by selectively absorbing light in a narrow wavelength region. When the full width at half maximum (FWHM) is within the range, selectivity in a green wavelength region may be increased. The thin film may be a thin film deposited under a vacuum condition.

The compound may be formed into a thin film by using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound has, for example, at least about 3° C., for example at least about 10° C. higher melting point than the deposition temperature and thus may be desirably used for the deposition.

Specifically, a donor/acceptor-type material represented by Chemical Formula 1 may be thermally decomposed at its melting point (Tm) because the melting point (Tm) of the material is similar to a decomposition temperature (Td). Accordingly, when the material has a lower Tm than a sublimation temperature (deposition temperature, Ts) at which the material is vacuum-deposited to form a film, the material may be decomposed before sublimated (deposited) and not be used to manufacture a device. Since as for this material, Tm is higher than Ts, and desirably, Tm−Ts≥3° C., for example Tm−Ts≥10° C., this material is appropriate for manufacturing a stable image sensor.

In addition, a micro lens array (MLA) needs to be formed to concentrate light after manufacturing a photoelectric device (organic photoelectric device) during manufacture of an image sensor. This micro lens array requires a relatively high temperature (about 160° C. or greater, 170° C. or greater, 180° C. or greater, or 190° C. or greater), and this annealing process may deteriorate performance of the photoelectric device. The performance deterioration of the photoelectric device during the annealing process of MLA may be caused not by chemical decomposition of an organic material but its morphology change. The morphology change is in general caused, when a material starts a thermal vibration due to the annealing process, but a material having a firm molecular structure may not have the thermal vibration and be prevented from the deterioration by the annealing process. The compound may be suppressed from the thermal vibration of molecules due to a conjugation structure (G-containing linking structure in Chemical Formula 1) in a donor region and stably maintained during the MLA annealing process and thus secure process stability.

The compound may be a p-type semiconductor compound.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the desirable HOMO-LUMO level of the compound, when the compound has a HOMO level ranging from about 5.2 eV to about 5.8 eV and an energy bandgap ranging from about 1.4 eV to about 2.6 eV, the LUMO level of the compound is in a range of about 3.8 eV to about 3.2 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In some example embodiments, in view of a thin film formation, a stably depositable compound is desirable and thus the compound has a molecular weight of about 300 g/mol to about 1500 g/mol. However, even though the compound has a molecular weight out of the range, any sublimable (depositable) compound may be used without limitation. In addition, when the compound is formed to form a thin film using a coating process, any compound that is dissolved in a solvent and coated may be used without limitation.

Hereinafter, a photoelectric device including the compound according to an example embodiment is described with reference to drawings.

FIG. 1 is a cross-sectional view showing a photoelectric device according to an example embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor. The opaque conductor may be a metal such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 500 nm and less than or equal to about 600 nm, for example greater than or equal to about 530 nm, greater than or equal to about 535 nm, or greater than or equal to about 540 nm and less than or equal to about 590 nm, or less than or equal to about 580 nm.

The active layer 30 may exhibit a light absorption curve having a relatively narrow full width at half maximum (FWHM) of about 50 nm to about 130 nm, for example about 50 nm to about 120 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include one of C60, C70, C76, C78, C80, C82, C84, C90, C96, C240, C540, or a mixture thereof, or a fullerene nanotube, or the like. The fullerene derivative may refer to compounds of these fullerenes having a substituent attached thereto. The fullerene derivative may include a substituent such as an alkyl group (e.g., C1 to C30 alkyl group), an aryl group (e.g., C6 to C30 aryl group), or a heterocyclic group (e.g., C3 to C30 cycloalkyl group). Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathiin ring, a phenothiazine ring, or a phenazine ring.

The sub-phthalocyanine or the sub-phthalocyanine derivative may be represented by Chemical Formula 6.

[Chemical Formula 6]

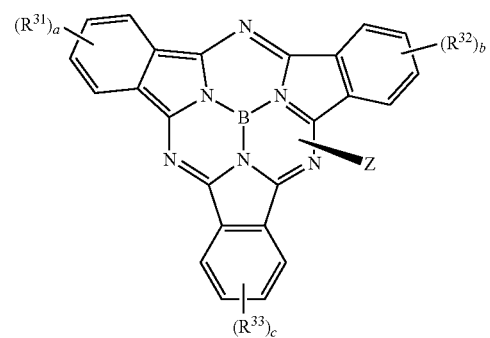

In Chemical Formula 6, $R^{31}$ to $R^{33}$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c may be integers ranging from 1 to 3, and Z may be a monovalent substituent.

For example, Z may be a halogen or a halogen-containing group, for example F, Cl, an F-containing group, or a Cl-containing group.

The halogen may refer to F, Cl, Br, or I and the halogen-containing group refers to an alkyl group (e.g., C1 to C30 alkyl group) where at least one of hydrogen is replaced by F, Cl, Br, or I.

The thiophene derivative may be for example represented by Chemical Formula 7 or Chemical Formula 8, but is not limited thereto.

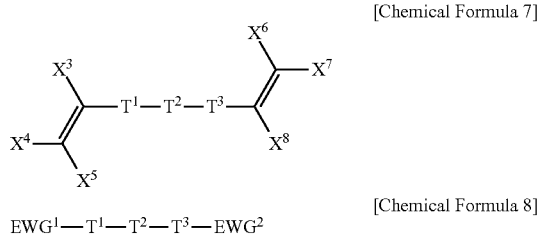

[Chemical Formula 7]

[Chemical Formula 8]

EWG$^1$—T$^1$—T$^2$—T$^3$—EWG$^2$

In Chemical Formulae 7 and 8,

T$^1$, T$^2$, and T$^3$ may be aromatic rings including substituted or unsubstituted thiophene moieties, T$^1$, T$^2$, and T$^3$ may independently be present or are fused to each other, X$^3$ to X$^8$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and EWG$^1$ and EWG$^2$ may independently be electron withdrawing groups.

For example, in Chemical Formula 8, at least one of X$^3$ to X$^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

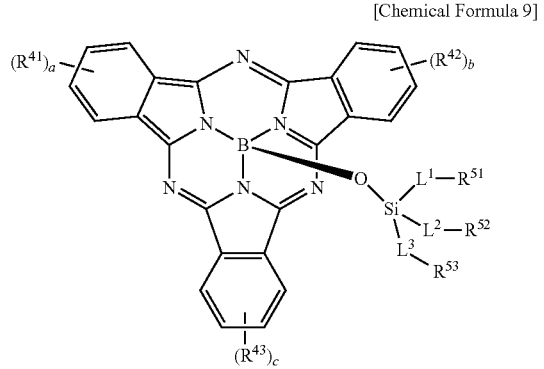

[Chemical Formula 9]

In Chemical Formula 9,

R$^{41}$ to R$^{43}$ may independently be one of hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of R$^{41}$ to R$^{43}$ are linked with each other to provide a fused ring, L$^1$ to L$^3$ may independently be one of a single bond, a substituted or unsubstituted C1 to C30 alkylene group, a substituted or unsubstituted C6 to C30 arylene group, divalent substituted or unsubstituted C3 to C30 heterocyclic group, or a combination thereof, R$^{51}$ to R$^{53}$ may independently be one of a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, a to c may independently be an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, or a p-type layer/n-type layer, or the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the ranges, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of the active layer 30 may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a desired (and/or alternatively predetermined) wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another example embodiment is described with reference to FIG. 2.

Figure 2:
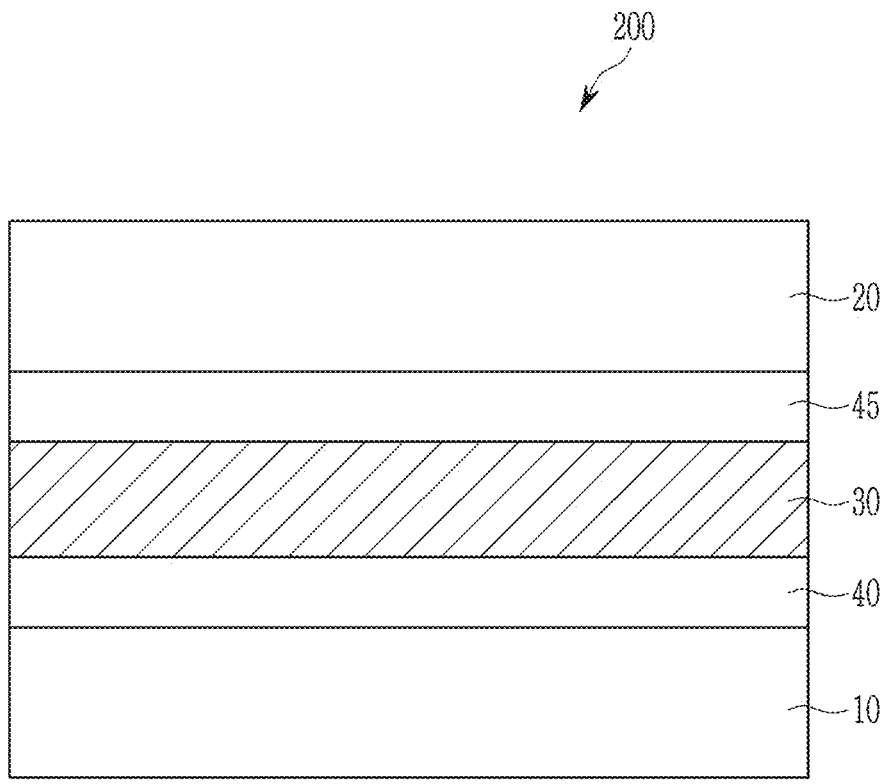
FIG. 2 is a cross-sectional view of a photoelectric device according to another example embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]-benzidine (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and a light emitting device, but is not limited thereto.

Hereinafter, an example of an image sensor including the photoelectric device is described referring to drawings. As an example of an image sensor, an organic CMOS image sensor is described.

Figure 3:
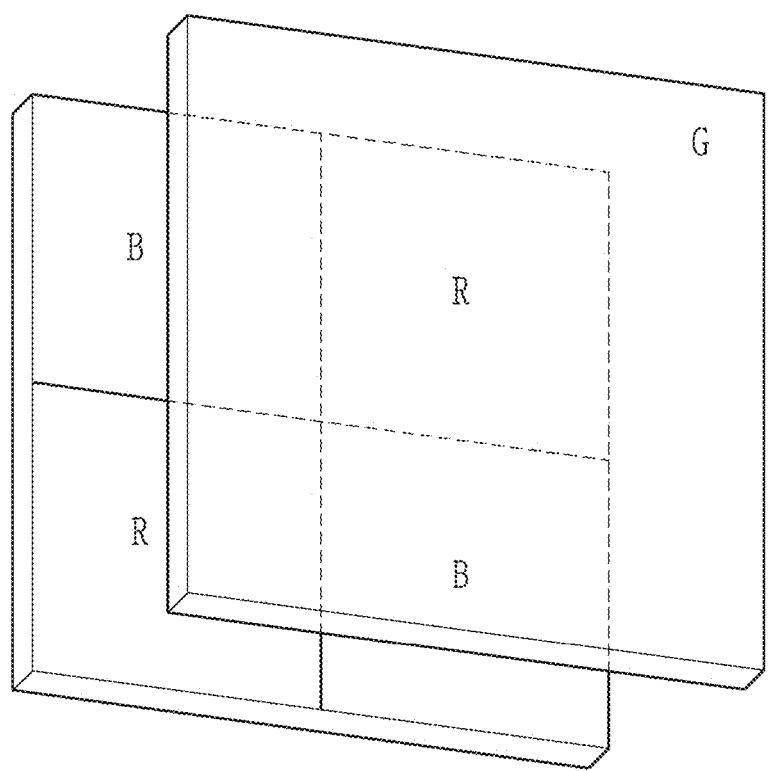
FIG. 3 is schematic top plan view showing an organic CMOS image sensor according to an example embodiment.
Figure 4:
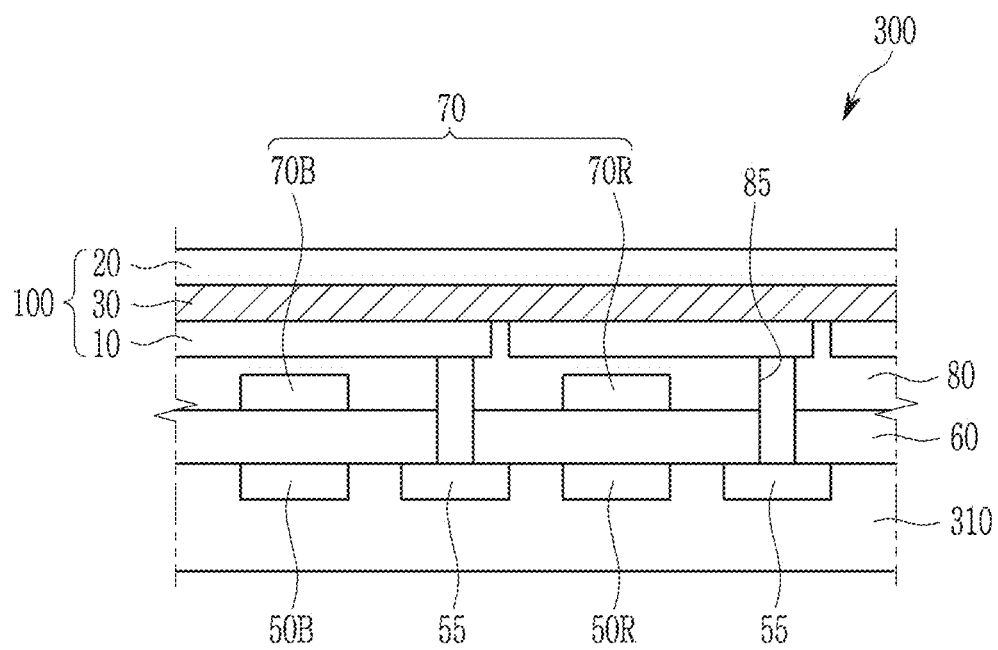
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing devices 50B and 50R, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel, but do not limited thereto, for example, the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an example embodiment, a cyan filter 70C and a yellow filter 70Y may be disposed instead of the blue filter 70B and the red filter 70R, respectively. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

Another color filter layer may be further disposed on the photoelectric device 100. The color filter layer may include a blue filter 70B and a red filter 70R or a cyan filter 70C and a yellow filter.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, another color filter layer may be further disposed on the photoelectric device 100. The color filter layer may include a blue filter 70B and a red filter 70R or a cyan filter 70C and a yellow filter.

Figure 5:
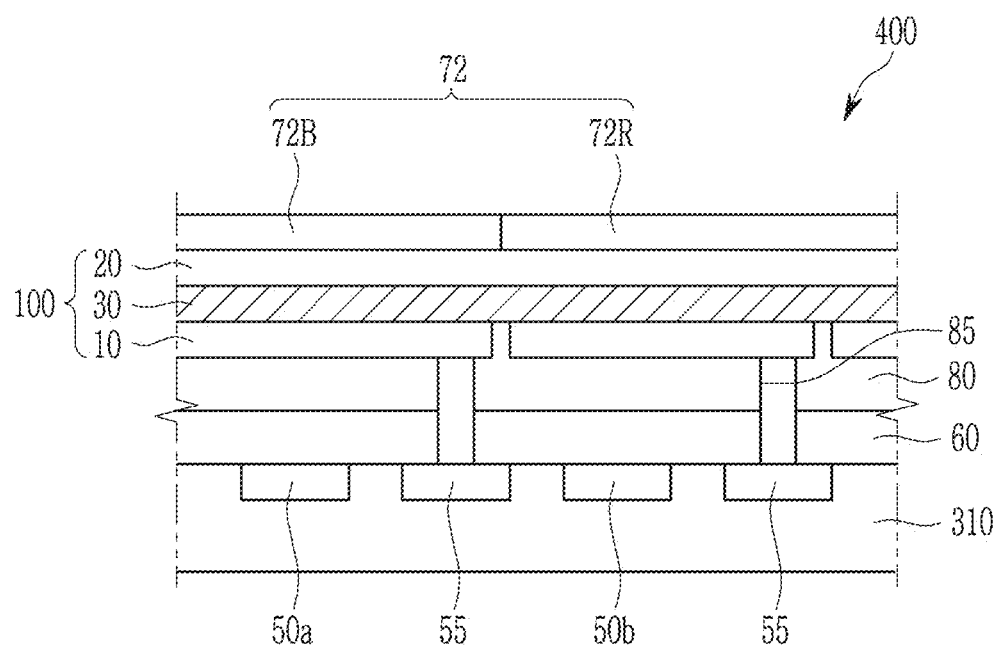
FIG. 5 is a cross-sectional view showing an organic CMOS image sensor according to an example embodiment.

The color filter layer may be disposed on the photoelectric device 100. An organic CMOS image sensor having such a structure is shown in FIG. 5. FIG. 5 is a cross-sectional view showing an organic CMOS image sensor 400 according to an example embodiment. Referring to FIG. 5, the organic CMOS image sensor 400 has the same structure as the organic CMOS image sensor 300 shown in FIG. 4, except that a color filter layer 72 including a blue filter 72B and a red filter 72R is disposed on the photoelectric device 100. In addition, a cyan filter 70C and a yellow filter 72Y may be disposed instead of the blue filter 72B and the red filter 72R, respectively.

Figure 6:
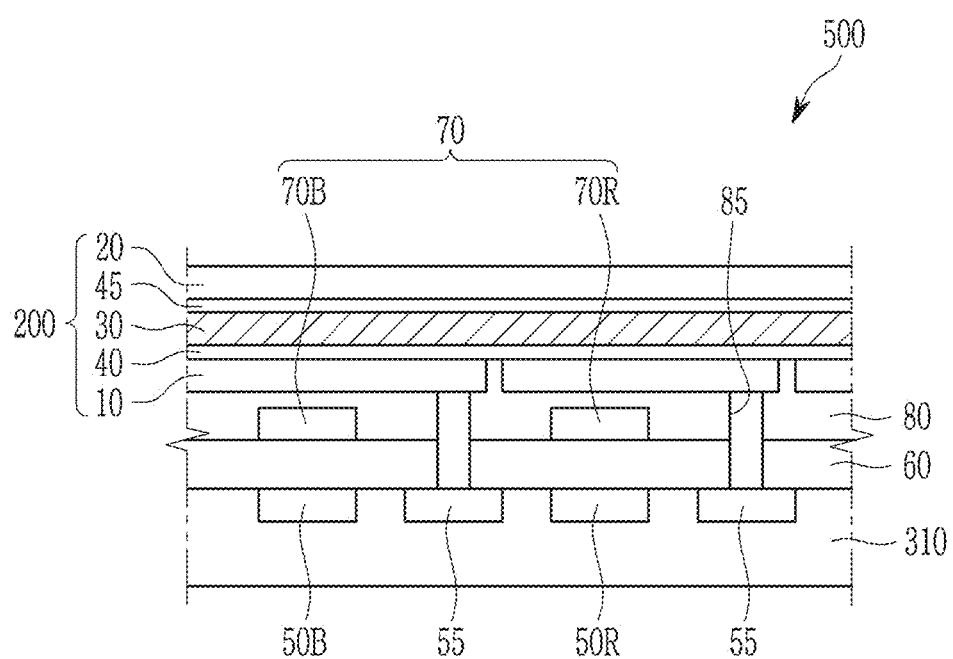
FIG. 6 is a schematic cross-sectional view showing an organic CMOS image sensor according to another example embodiment.

In FIGS. 4 and 5, the photoelectric device 100 of FIG. 1 is included, but it is not limited thereto, and thus the photoelectric device 200 of FIG. 2 may be applied in the same manner. FIG. 6 shows a structure of an image sensor having such a structure, and is a cross-sectional view of an organic CMOS image sensor 500 including the photoelectric device 200 in FIG. 2.

Figure 7:
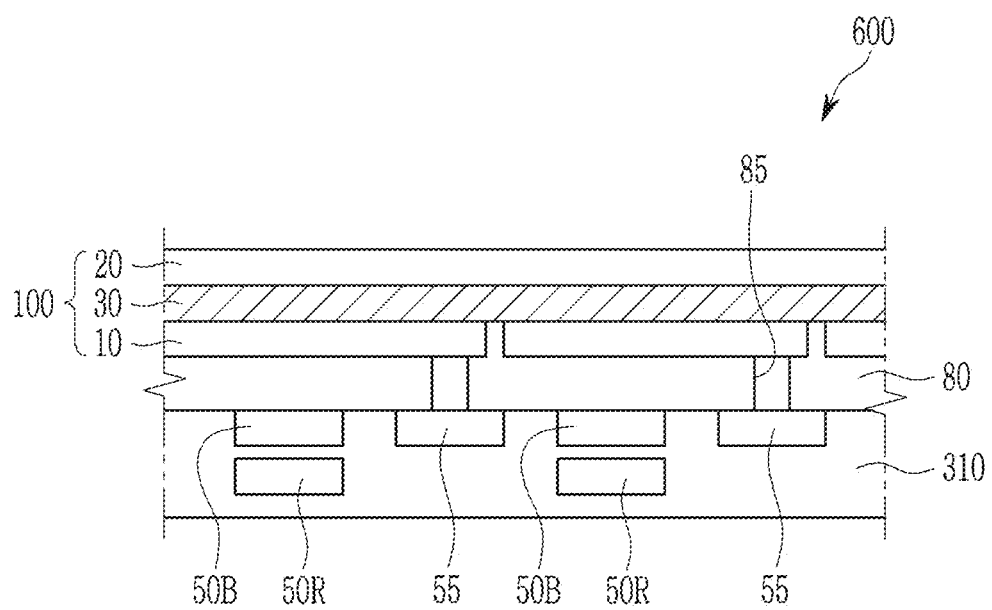
FIG. 7 is a schematic cross-sectional view showing an organic CMOS image sensor according to another example embodiment.

FIG. 7 is a cross-sectional view showing the organic CMOS image sensor according to another example embodiment.

Referring to FIG. 7, the organic CMOS image sensor 600 includes a semiconductor substrate 310 integrated with photo-sensing devices 50B and 50R, a transmission transistor (not shown), and a charge storage 55, an insulation layer 80, and an photoelectric device 100, like the example embodiment illustrated in FIG. 6.

However, the organic CMOS image sensor 600 according to the example embodiment illustrated in FIG. 7 includes the blue photo-sensing device 50B and the red photo-sensing device 50R that are stacked and does not include a color filter layer 70, unlike the example embodiment illustrated in FIG. 6. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption of other light except a green wavelength region may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
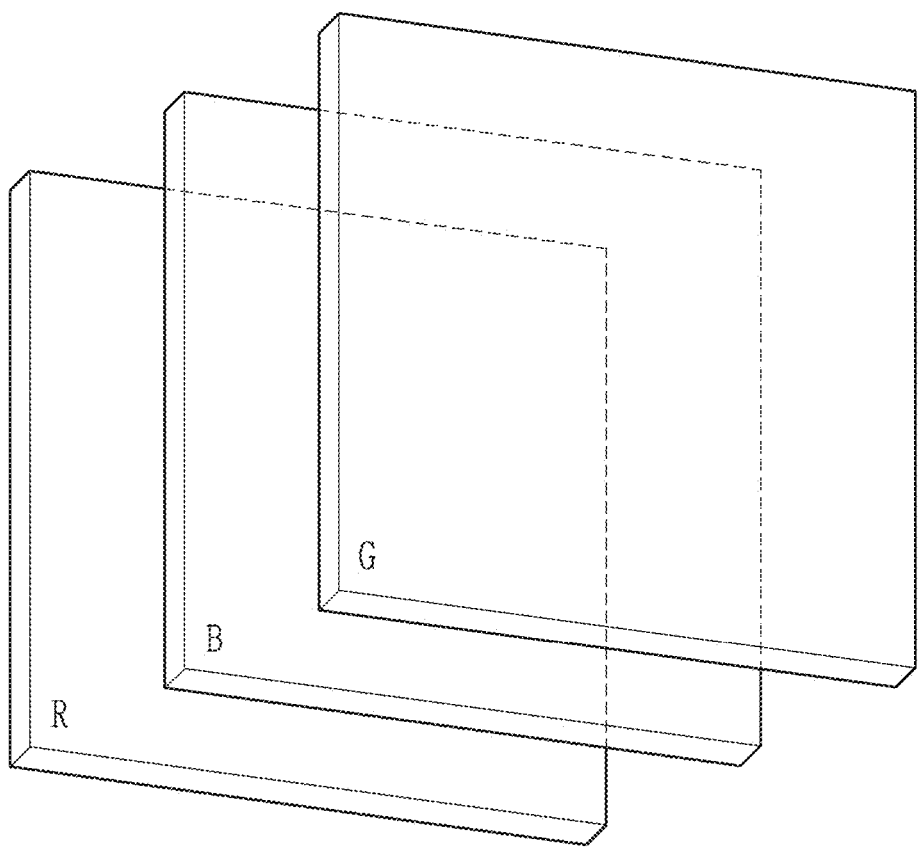
FIG. 8 is a schematic view showing an organic CMOS image sensor according to another example embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the above photoelectric device 100 or photoelectric device 200, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the green photoelectric device selectively absorbing light in a green wavelength region, the red photoelectric device selectively absorbing light in a red wavelength region, and the blue photoelectric device selectively absorbing light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility ($\Delta E^*ab$) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Me., USA), and is represented by minimum illuminance expressed by lux at a ratio of 10 between signal and noise. Accordingly, the smaller the YSNR10 is, the higher sensitivity is.

On the other hand, the color reproducibility ($\Delta E^*ab$) shows a difference from standard colors in an X-Rite chart, and the $\Delta E^*ab$ is defined as a distance between two points on a $L^*a^*b^*$ color space by CIE (Commission International de L' Eclairage) in 1976. For example, the color difference may be calculated according to Equation 1.

$$\Delta E = \sqrt{(\Delta L^*)^2 + (\Delta a^*)^2 + (\Delta b^*)^2} \qquad \text{[Equation 1]}$$

In Equation 1, $\Delta L^*$ denotes a change of a color coordinate $L^*$ compared with the color coordinate $L^*$ at room temperature (about 20° C. to about 25° C.), $\Delta a^*$ denotes a change of a color coordinate $a^*$ compared with the color coordinate $a^*$ at room temperature, and $\Delta b^*$ denotes a change of a color coordinate $b^*$ compared with the color coordinate $b^*$ at room temperature.

In order to manufacture an image sensor having high sensitivity at high color reproducibility, YSNR10≤100 lux at $\Delta E^*ab \leq 3$, and herein, the compound may realize sensitivity of YSNR10≤100 lux at $\Delta E^*ab \leq 3$.

The image sensor may be applied to various electronic devices, for example, a mobile phone, a digital camera, and the like but is not limited thereto.

Hereinafter, the embodiments are illustrated in more detail with reference to examples. However, these examples are non-limiting, and inventive concepts are not limited thereto.

Synthesis Example 1: Synthesis of Compound Represented by Chemical Formula 1-1 (2-((5-(10H-phenoselenazin-10-yl)tellurophen-2-yl)methylene)-1H-indene-1,3(2H)-dione)

[Chemical Formula 1-1]

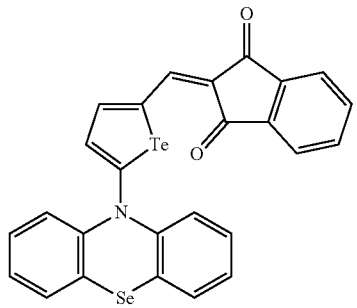

[Reaction Scheme 1-1]

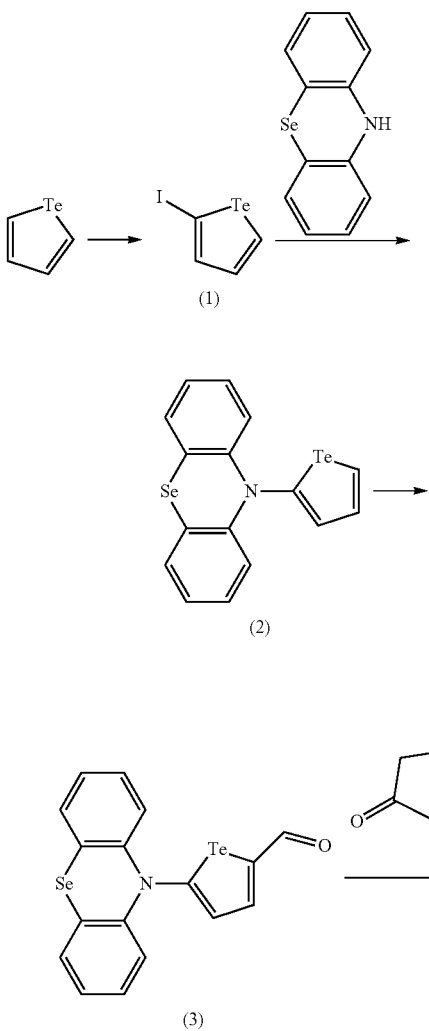

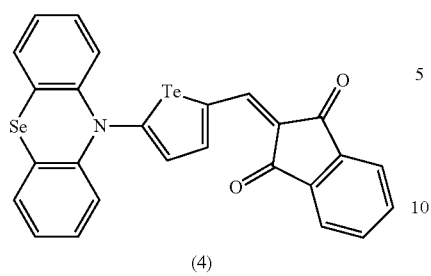

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 6.17 g (25.2 mmol) of 10H-phenoselenazine are heated and refluxed in 100 ml of anhydrous toluene in the presence of 5 mol % of Pd(dba)$_2$, 5 mol % of P(tBu)$_3$, and 2.66 g (27.7 mmol) of NaOtBu for 2 hours. A product therefrom is separated and purified through silica gel column chromatography (toluene: hexane in a volume ratio of 1:4) to obtain 4.25 g of 10-(tellurophen-2-yl)-10H-phenoselenazine (yield: 39.8%).

(iii) Synthesis of Compound (3)

1.84 ml of phosphoryl chloride is added in a dropwise fashion to 6.0 ml of N,N-dimethylformamide at −15° C., and the mixture is stirred at room temperature (24° C.) for 2 hours. A resultant therefrom is slowly added in a dropwise fashion to a mixture of 200 ml of dichloromethane and 4.25 g of Compound (2) at −15° C., and the obtained mixture is stirred at room temperature for 30 minutes and concentrated under a reduced pressure. Subsequently, 100 ml of water is added thereto, an aqueous sodium hydroxide solution is added thereto until pH becomes 14, and the obtained mixture is stirred at room temperature (24° C.) for 2 hours. An organic layer is extracted therefrom by using dichloromethane and washed with an aqueous sodium chloride solution and then, dried by adding anhydrous magnesium sulfate thereto. A product therefrom is separated and purified through silica gel column chromatography (hexane: ethylacetate in a volume ratio of 4:1) to obtain 2.50 g of 5-(10H-phenoselenazin-10-yl)tellurophene-2-carbaldehyde (yield: 55.2%).

(iv) Synthesis of Compound (4) Represented by Chemical Formula 1-1

2.50 g (4.21 mmol) of Compound (3) is suspended in ethanol, 0.74 g (5.05 mmol) of 1H-Indene-1,3(2H)-dione is added thereto, and the mixture is reacted at 50° C. for 2 hours to obtain 2.02 g of a final compound represented by Chemical Formula 1-1 (yield: 82.8%). The compound is sublimed and purified up to purity of 99.9%.

$^1$H-NMR (500 MHz, Methylene Chloride-d$_2$): δ 7.87 (s, 1H), 7.72 (m, 6H), 7.49 (m, 4H), 7.34 (m, 3H), 6.82 (d, 1H).

Synthesis Example 2: Synthesis of Compound Represented by Chemical Formula 1-2 (2-((5-(10,10-dimethyldibenzo[b,e][1,4]azasilin-5(10H)-yl)tellurophen-2-yl)methylene)-1H-indene-1,3(2H)-dione)

[Chemical Formula 1-2]

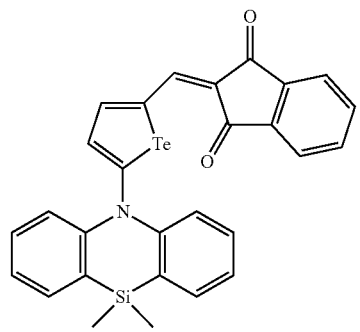

[Reaction Scheme 1-2]

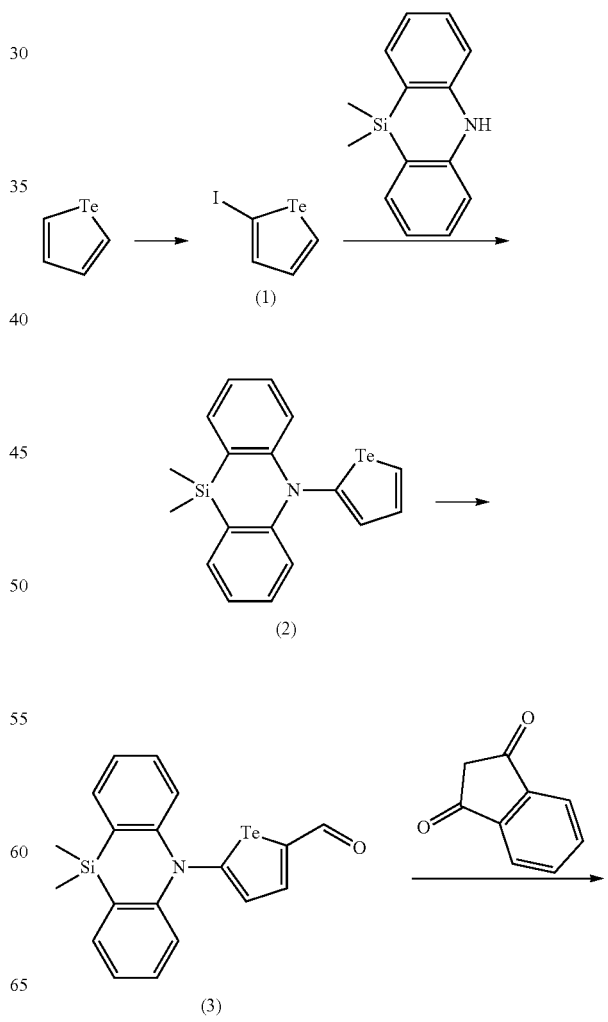

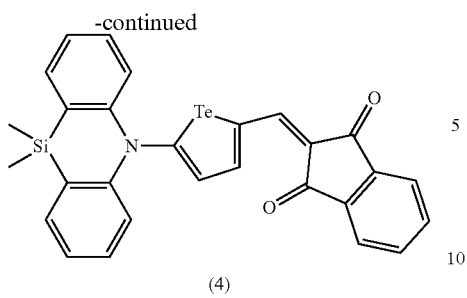

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 10.0 g (44.6 mmol) of 10,10-dimethyl-5,10-dihydrodibenzo[b,e][1,4]azasiline are heated and refluxed in 200 ml of anhydrous toluene in the presence of 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=1:4 (volume ratio)) to obtain 6.8 g of 10,10-dimethyl-5-(tellurophen-2-yl)-5,10-dihydrodibenzo[b,e][1,4]azasiline (yield: 37.8%).

(iii) Synthesis of Compound (3)

6.2 ml of phosphoryl chloride is added in a dropwise fashion to 30.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding anhydrous magnesium sulfate thereto. A product obtained therefrom is separated and purified through silica gel column chromatography (hexane:ethylacetate=4:1 (volume ratio)) to obtain 2.82 g of 5-(10,10-dimethyldibenzo[b,e][1,4]azasilin-5(10H)-yl)tellurophene-2-carbaldehyde (yield: 38.8%).

(iv) Synthesis of Compound (4) Represented by Chemical Formula 1-2

2.82 g (6.54 mmol) of Compound (3) is suspended in ethanol, 1.15 g (7.85 mmol) of 1H-Indene-1,3(2H)-dione is added thereto and then, reacted therewith at 50° C. for 2 hours to obtain 2.20 g of a final compound represented by Chemical Formula 1-2 (yield: 60.1%). The compound is sublimed and purified up to purity of 99.9%.

$^1$H-NMR (500 MHz, Methylene Chloride-d$_2$): δ 7.98 (s, 1H), 8.12 (m, 6H), 7.52 (m, 4H), 7.54 (m, 3H), 6.98 (d, 1H). 0.47 (s, 6H).

Synthesis Example 3: Synthesis of Compound Represented by Chemical Formula 1-3 (5-((5-(10H-phenoselenazin-10-yl)tellurophen-2-yl)methylene)-1,3-dimethyl-2-thioxodihydropyrimidine-4,6(1H,5H)-dione)

[Chemical Formula 1-3]

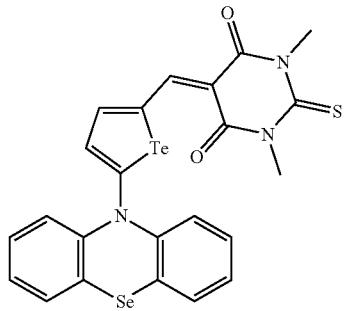

[Reaction Scheme 1-3]

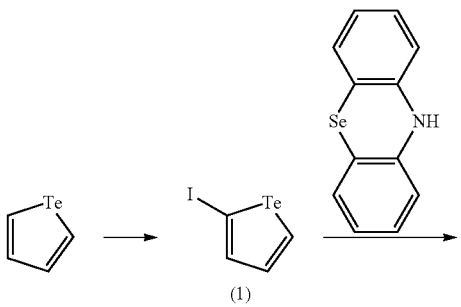

(1)

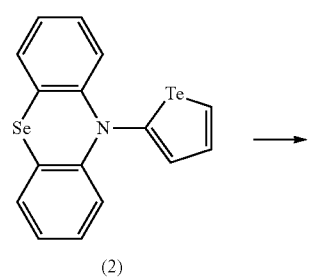

(2)

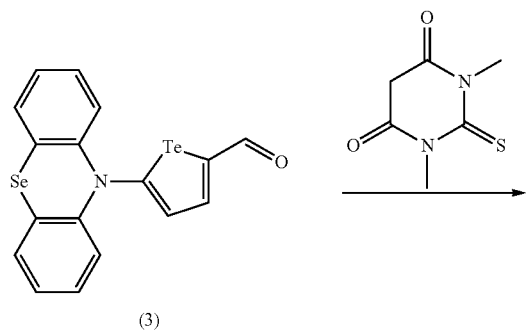

(3)

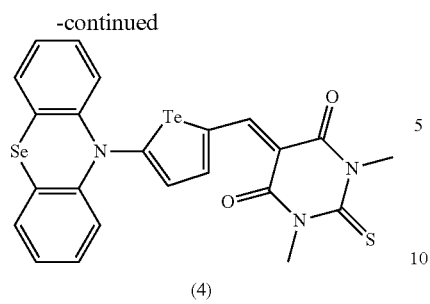

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 6.17 g (25.2 mmol) of 10H-phenoselenazine are heated and refluxed in 100 ml of an anhydrous toluene in the presence of 5 mol % of Pd(dba)$_2$, 5 mol % of P(tBu)$_3$, and 2.66 g (27.7 mmol) of NaOtBu for 2 hours. A product obtained therefrom is separated and purified through silica gel column chromatography (toluene:hexane=1:4 (volume ratio)) to obtain 4.25 g of 10-(tellurophen-2-yl)-10H-phenoselenazine (yield: 19.6%).

(iii) Synthesis of Compound (3)

1.84 ml of phosphoryl chloride is added in a dropwise fashion to 6.0 ml of N,N-dimethylformamide at −15° C., and the mixture is stirred at room temperature (24° C.) for 2 hours. A resultant therefrom is slowly added in a dropwise fashion to a mixture of 180 ml of dichloromethane and 2.10 g of Compound (2) at −15° C., and the obtained mixture is stirred at room temperature for 30 minutes and concentrated under a reduced pressure. Subsequently, 100 ml of water is added thereto, an aqueous sodium hydroxide solution is added thereto until pH becomes 14, and then, the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product obtained therefrom is separated and purified through silica gel column chromatography (hexane:ethyl acetate=4:1 (volume ratio)) to obtain 2.50 g of 5-(10H-phenoselenazin-10-yl)tellurophene-2-carbaldehyde (yield: 53.6%).

(iv) Synthesis of Compound (4) Represented by Chemical Formula 1-3

2.50 g (4.21 mmol) of Compound (3) is suspended in ethanol, and 0.87 g (5.05 mmol) of 1,3-dimethyl-2-thiobarbituric acid synthesized in a method described in J. Pharmacol., 1944, 82, 292, p. 4417 is added thereto and mixed therewith at 50° C. for 2 hours to obtain 1.76 g of a final compound represented by Chemical Formula 1-3 (yield: 69.1%). The compound is sublimed and purified up to purity of 99.9%.

$^1$H-NMR (500 MHz, Methylene Chloride-d$_2$): δ 8.29 (s, 1H), 7.83 (d, 1H), 7.73 (d, 2H), 7.51 (d, 2H), 7.37 (t, 2H), 6.99 (t, 2H), 5.32 (d, 1H), 3.67 (d, 6H).

Synthesis Example 4: Synthesis of Compound Represented by Chemical Formula 1-4 (5-((5-(10,10-dimethyldibenzo[b,e][1,4]azasilin-5(10H)-yl)tellurophen-2-yl)methylene)-1,3-dimethyl-2-thioxodihydropyrimidine-4,6(1H,5H)-dione)

[Chemical Formula 1-4]

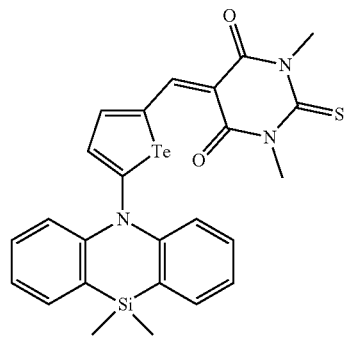

[Reaction Scheme 1-4]

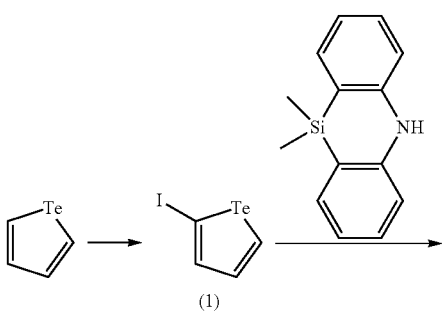
(1)

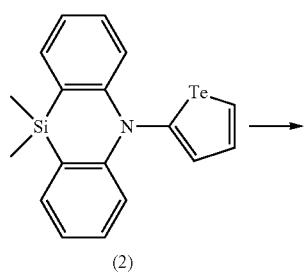
(2)

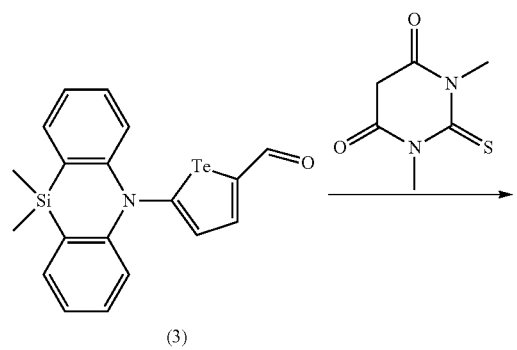
(3)

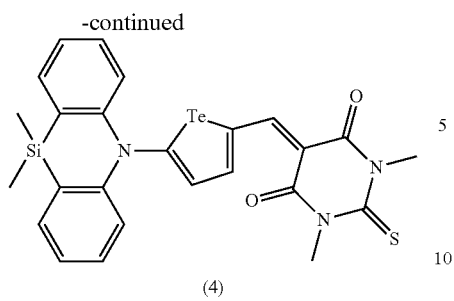

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 10.0 g (44.6 mmol) of 10,10-dimethyl-5,10-dihydrodibenzo[b,e][1,4]azasiline are heated and refluxed in 200 ml of anhydrous toluene in the presence of 5 mol % of Pd(dba)$_2$, 5 mol % of P(tBu)$_3$, and 12.9 g (133.9 mmol) of NaOtBu for 2 hours. A product obtained therefrom is separated and purified through silica gel column chromatography (toluene:hexane=1:4 (volume ratio)) to obtain 6.8 g of 10,10-dimethyl-5-(tellurophen-2-yl)-5,10-dihydrodibenzo[b,e][1,4]azasiline (yield: 37.8%).

(iii) Synthesis of Compound (3)

6.2 ml of phosphoryl chloride is added in a dropwise fashion to 30.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and then, dried by adding anhydrous magnesium sulfate thereto. A product obtained therefrom is separated and purified through silica gel column chromatography (hexane:ethylacetate=4:1 (volume ratio)) to obtain 2.82 g of 5-(10,10-dimethyldibenzo[b,e][1,4]azasilin-5(10H)-yl)tellurophene-2-carbaldehyde (yield: 38.8%).

(iv) Synthesis of Compound (4) Represented by Chemical Formula 1-4

2.82 g (6.54 mmol) of Compound (3) is suspended in ethanol, and 1.35 g (7.85 mmol) of 1,3-dimethyl-2-thiobarbituric acid is added thereto and reacted therewith at 50° C. for 2 hours to obtain 2.98 g of a final compound represented by Chemical Formula 1-4 (yield: 77.8%). The compound is sublimed and purified up to purity of 99.9%.

$^1$H-NMR (500 MHz, Methylene Chloride-d$_2$): δ 8.46 (s, 1H), 8.26 (d, 1H), 7.80 (d, 2H), 7.71 (d, 2H), 7.54 (t, 2H), 7.42 (t, 2H), 6.93 (d, 1H), 3.68 (d, 6H), 0.45 (s, 6H).

Synthesis Example 5: Synthesis of Compound Represented by Chemical Formula 1-5

[Chemical Formula 1-5]

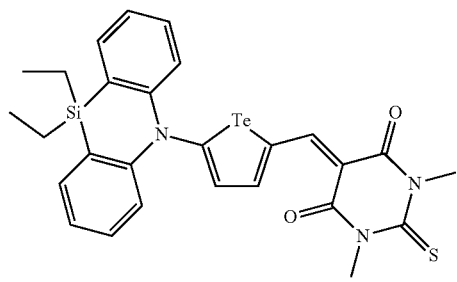

[Reaction Scheme 1-5]

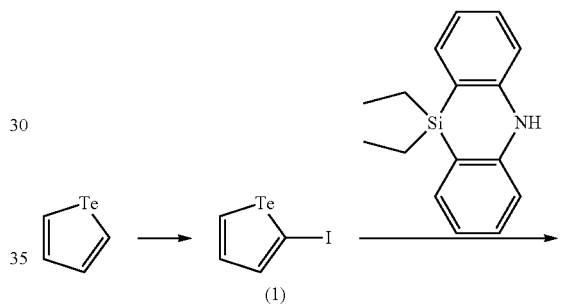

(1)

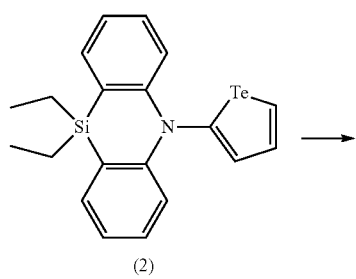

(2)

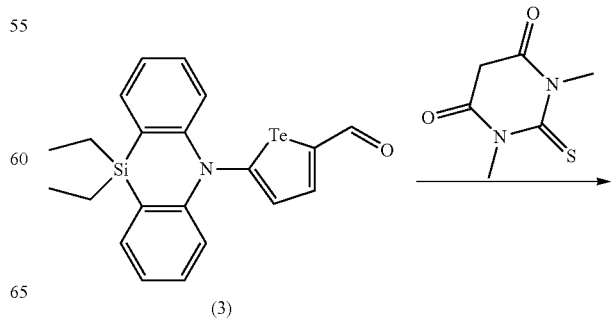

(3)

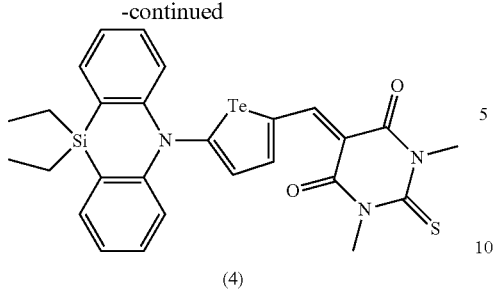

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 11.3 g (44.6 mmol) of 10,10-diethyl-5,10-dihydrodibenzo[b,e][1,4]azasiline are heated and refluxed in 200 ml of anhydrous toluene in the presence of 5 mol % of Pd(dba)$_2$, 5 mol % of P(tBu)$_3$ and 12.9 g (133.9 mmol) of NaOtBu for 2 hours. A product obtained therefrom is separated and purified through silica gel column chromatography (toluene:hexane=1:4 (volume ratio)) to obtain 7.2 g of 10,10-diethyl-5-(tellurophen-2-yl)-5,10-dihydrodibenzo[b,e][1,4]azasiline (yield: 37.4%).

(iii) Synthesis of Compound (3)

13.5 ml of phosphoryl chloride is added in a dropwise fashion to 34.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 7.2 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product obtained therefrom is separated and purified through silica gel column chromatography (hexane:ethyl acetate=4:1 (volume ratio)) to obtain 2.00 g of 5-(10,10-diethyldibenzo[b,e][1,4]azasilin-5(10H)-yl)tellurophene-2-carbaldehyde (yield: 26.1%).

(iv) Synthesis of Compound (4) Represented by Chemical Formula 1-5

2.00 g (4.36 mmol) of Compound (3) is suspended in ethanol, 0.90 g (5.23 mmol) of 1,3-dimethyl-2-thiobarbituric acid is added thereto, and then reacted at 50° C. for 2 hours to obtain 2.04 g of a final compound represented by Chemical Formula 1-5 (yield: 76.4%). The compound is sublimed and purified up to purity of 99.9%.

$^1$H-NMR (500 MHz, Methylene Chloride-d$_2$): δ 8.46 (s, 1H), 8.26 (d, 1H), 7.82 (d, 2H), 7.72 (d, 2H), 7.56 (t, 2H), 7.46 (t, 2H), 6.93 (d, 1H), 3.70 (d, 6H), 1.50 (t, 4H), 0.90 (s, 6H).

Synthesis Example 6: Synthesis of Compound Represented by Chemical Formula 1-6

[Chemical Formula 1-6]

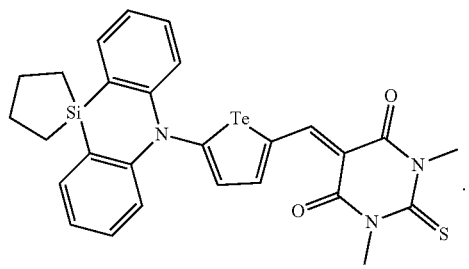

[Reaction Scheme 1-6]

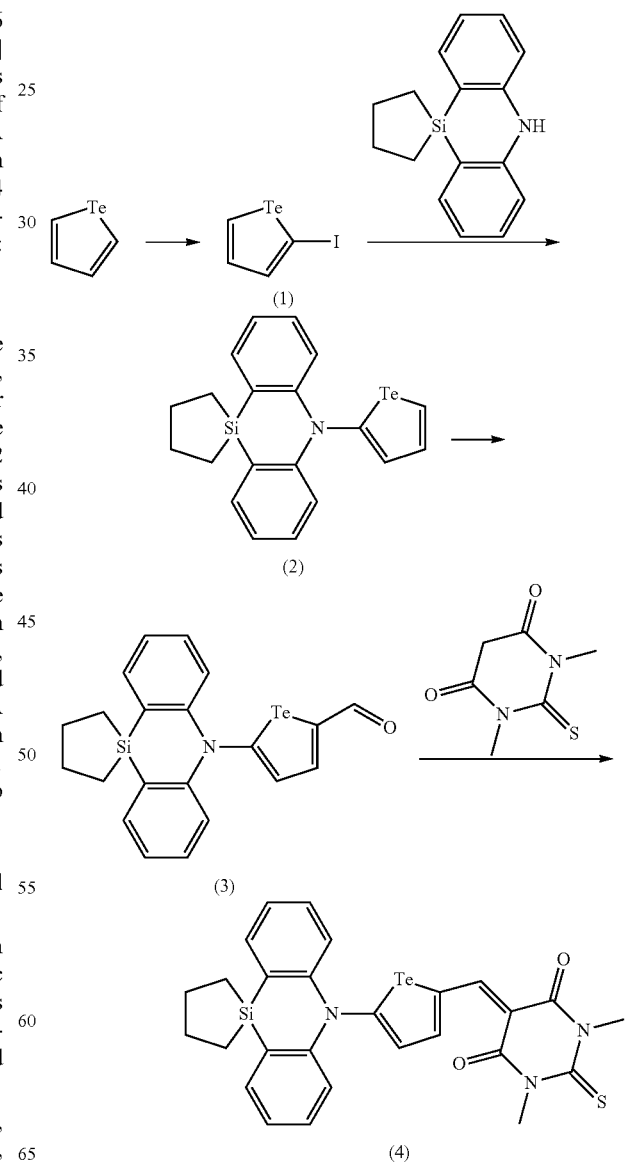

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 11.2 g (44.6 mmol) of 5H-spiro[dibenzo[b,e][1,4]azasiline-10,1'-silolane are heated and refluxed in 200 ml of anhydrous toluene in the presence of 5 mol % of Pd(dba)$_2$, 5 mol % of P(tBu)$_3$ and 12.9 g (133.9 mmol) of NaOtBu for 2 hours. A product therefrom is separated and purified through silica gel column chromatography (toluene: hexane in a volume ratio of 1:4) to obtain 6.8 g of 5-(tellurophen-2-yl)-5H-spiro[dibenzo[b,e][1,4]azasiline-10,1'-silolane (yield: 35.5%).

(iii) Synthesis of Compound (3)

12.4 ml of phosphoryl chloride is added in a dropwise fashion to 38.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 2.00 g of 5-(5H-spiro[dibenzo[b,e][1,4]azasiline-10,1'-silolan]-5-yl)tellurophene-2-carbaldehyde (yield: 27.6%).

(iv) Synthesis of Compound (4) Represented by Chemical Formula 1-6

2.00 g (4.38 mmol) of Compound (3) is suspended in ethanol, 0.90 g (5.25 mmol) of 1,3-dimethyl-2-thiobarbituric acid is added thereto, and the mixture is reacted at 50° C. for 2 hours to obtain 2.1 g of a final compound represented by Chemical Formula 1-6 (yield: 78.5%). The compound is sublimed and purified up to purity of 99.9%.

$^1$H-NMR (500 MHz, Methylene Chloride-d$_2$): δ 8.48 (s, 1H), 8.28 (d, 1H), 7.82 (d, 2H), 7.74 (d, 2H), 7.58 (t, 2H), 7.46 (t, 2H), 6.92 (d, 1H), 3.72 (d, 6H), 1.88 (t, 8H)

Synthesis Example 7: Synthesis of Compound Represented by Chemical Formula 1-7

[Chemical Formula 1-7]

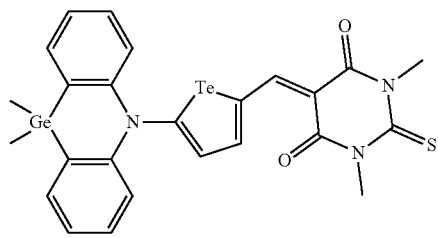

[Reaction Scheme 1-7]

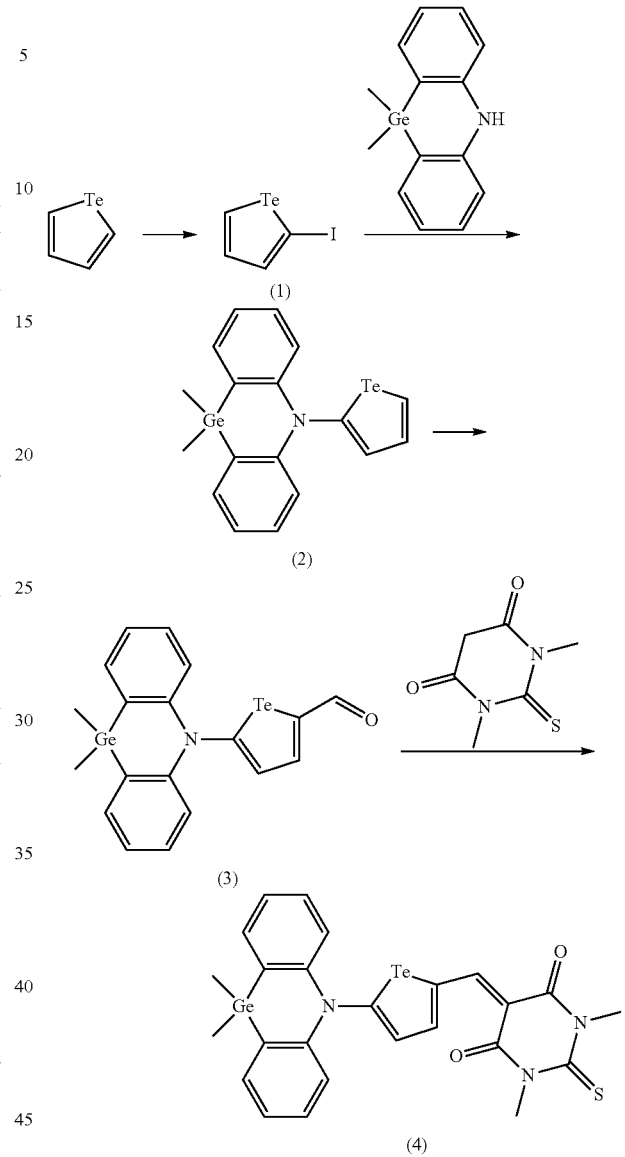

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 12.0 g (44.6 mmol) of 10,10-dimethyl-5,10-dihydrodibenzo[b,e][1,4]azagermine are heated and refluxed for 2 hours in 200 ml of anhydrous toluene in the presence of 4.5 mol % of Pd(dba)$_2$, 5 mol % of P(tBu)$_3$, and 12.9 g (133.9 mmol) of NaOtBu. A product obtained therefrom is separated and purified through silica gel column chromatography (toluene: hexane=1:4 (volume ratio)) to obtain 6.2 g of 10,10-dimethyl-5-(tellurophen-2-yl)-5,10-dihydrodibenzo[b,e][1,4]azagermin (yield: 31.0%).

(iii) Synthesis of Compound (3)

5.0 ml of phosphoryl chloride is added in a dropwise fashion to 16.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 6.2 g of Compound (2) at −15° C., and the obtained mixture is stirred at room temperature for 30 minutes and concentrated under a reduced pressure. Subsequently, 200 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 2.2 g of 5-(10,10-dimethyl-dibenzo[b,e][1,4]azagermin-5(10H)-yl)tellurophene-2-carbaldehyde (yield: 32.0%).

(iv) Synthesis of Compound (4) Represented by Chemical Formula 1-7

2.2 g (4.63 mmol) of Compound (3) is suspended in ethanol, and 0.96 g (5.55 mmol) of 1,3-dimethyl-2-thiobarbituric acid is added thereto, and then reacted at 50° C. for 2 hours to obtain 2.1 g of a final compound represented by Chemical Formula 1-7 (yield: 72.1%). The compound is sublimed and purified up to purity of 99.9%.

$^1$H-NMR (500 MHz, Methylene Chloride-$d_2$): δ 8.36 (s, 1H), 8.16 (d, 1H), 7.76 (d, 2H), 7.62 (d, 2H), 7.44 (t, 2H), 7.42 (t, 2H), 6.93 (d, 1H), 3.68 (d, 6H), 0.65 (s, 6H).

Reference Synthesis Example 1: Synthesis of Compound Represented by Chemical Formula 2-1

[Chemical Formula 2-1]

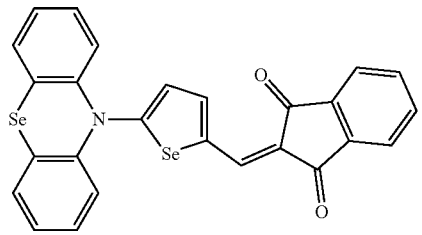

[Reaction Scheme 2-1]

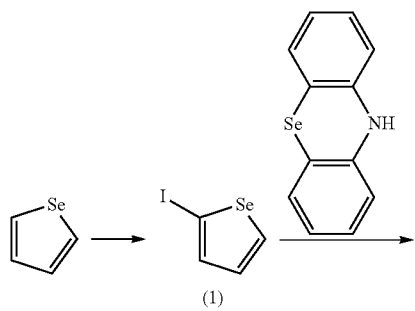

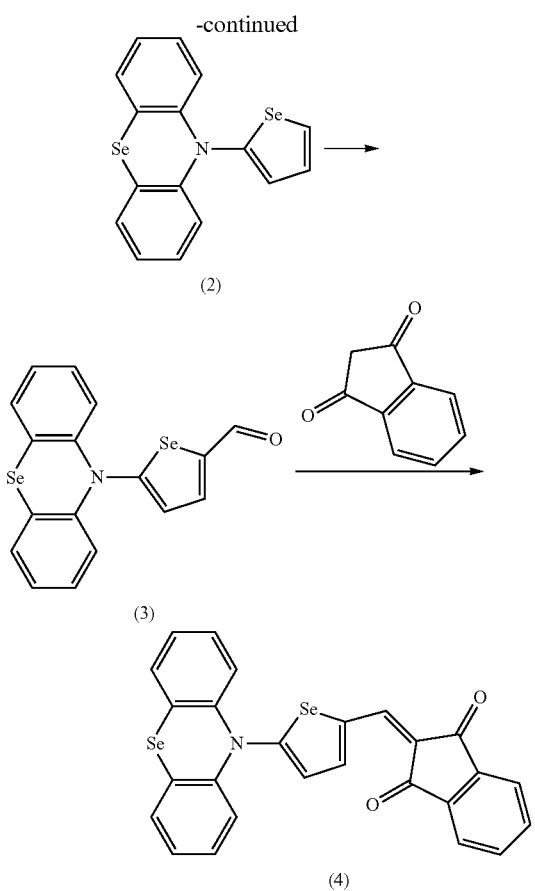

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 8.71 g (35.4 mmol) of 10H-phenoselenazine are heated and refluxed in 100 ml of anhydrous toluene in the presence of 5 mol % of Pd(dba)$_2$, 5 mol % of P(tBu)$_3$, and 10.2 g (106.15 mmol) of NaOtBu for 2 hours. A product therefrom is separated and purified through silica gel column chromatography (toluene:hexane in a volume ratio of 1:4) to obtain 8.2 g of 10-(selenophen-2-yl)-10H-phenoselenazine (yield: 54.7%).

(iii) Synthesis of Compound (3)

8.0 ml of phosphoryl chloride is added in a dropwise fashion to 30.0 ml of N,N-dimethylformamide at −15° C., and the mixture is stirred at room temperature (24° C.) for 2 hours. A resultant therefrom is slowly added in a dropwise fashion to a mixture of 180 ml of dichloromethane and 8.2 g of Compound (2) at −15° C., and the obtained mixture is stirred at room temperature for 30 minutes and concentrated under a reduced pressure. Subsequently, 200 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 4.5 g of 5-(10H-phenoselenazin-10-yl)selenophene-2-carbaldehyde (yield: 51.1%).

(iv) Synthesis of Compound (4) Represented by Chemical Formula 2-1

2.00 g (4.96 mmol) of Compound (3) is suspended in ethanol, 0.87 g (5.95 mmol) of 1H-indene-1,3(2H)-dione is added thereto, and then reacted at 50° C. for 2 hours to obtain 2.0 g of a final compound represented by Chemical Formula 2-1 (yield: 75.9%). The compound is sublimed and purified up to purity of 99.9%.

$^1$H-NMR (500 MHz, Methylene Chloride-d$_2$): δ 7.87 (s, 1H), 7.72 (m, 6H), 7.49 (m, 4H), 7.42 (m, 3H), 6.82 (d, 1H).

Reference Synthesis Example 2: Synthesis of Compound Represented by Chemical Formula 2-2

[Chemical Formula 2-2]

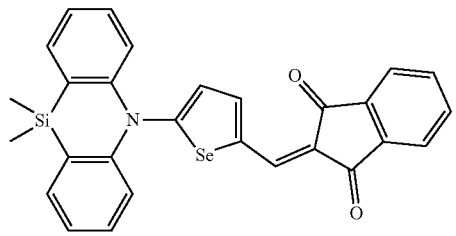

[Reaction Scheme 2-2]

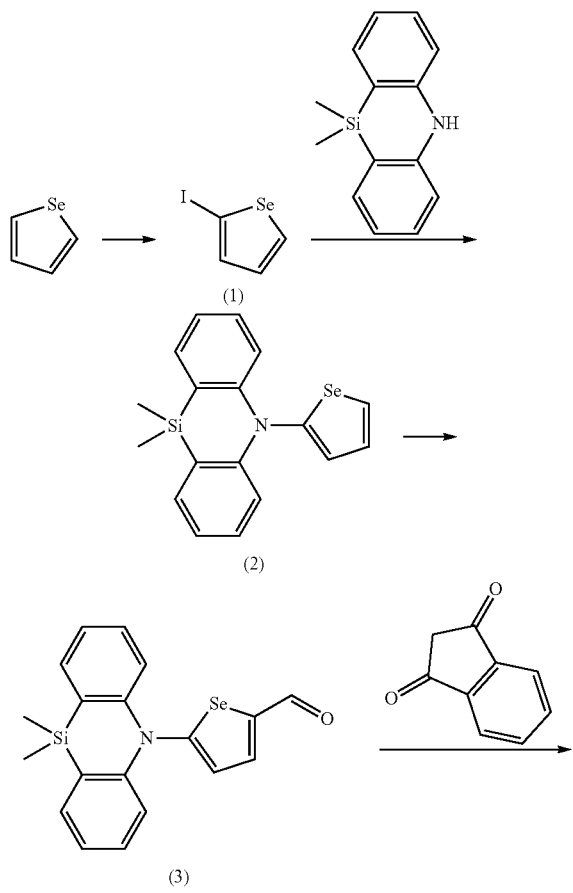

-continued

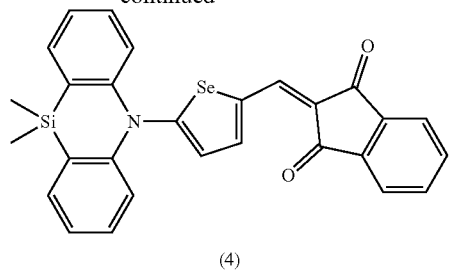

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (58.4 mmol) of 2-iodoselenophene and 11.9 g (58.4 mmol) of 10,10-dimethyl-5,10-dihydrodibenzo[b,e][1,4]azasiline are heated and refluxed in 200 ml of anhydrous toluene in the presence of 5 mol % of Pd(dba)$_2$, 5 mol % of P(tBu)$_3$, and 15.3 g (159.22 mmol) of NaOtBu for 2 hours. A product therefrom is separated and purified through silica gel column chromatography (toluene: hexane in a volume ratio of 1:4) to obtain 11.2 g of 10,10-dimethyl-5-(selenophen-2-yl)-5,10-dihydrodibenzo[b,e][1,4]azasiline (yield: 59.5%).

(iii) Synthesis of Compound (3)

8.2 ml of phosphoryl chloride is added in a dropwise fashion to 38.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 11.2 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 6.82 g of 5-(10,10-dimethyldibenzo[b,e][1,4]azasilin-5(10H)-yl)selenophene-2-carbaldehyde (yield: 56.4%).

(iv) Synthesis of Compound (4) Represented by Chemical Formula 2-2

3.00 g (7.85 mmol) of Compound (3) is suspended in ethanol, 1.38 g (9.41 mmol) of 1H-indene-1,3(2H)-dione is added thereto, and then reacted at 50° C. for 2 hours to obtain 3.40 g of a final compound represented by Chemical Formula 2-2 (yield: 84.9%). The compound is sublimed and purified up to purity of 99.9%.

$^1$H-NMR (500 MHz, Methylene Chloride-d$_2$): δ 7.98 (s, 1H), 8.12 (m, 6H), 7.60 (m, 3H), 7.52 (m, 4H), 6.98 (d, 1H). 0.47 (s, 6H).

Reference Synthesis Example 3: Synthesis of Compound Represented by Chemical Formula 2-3

[Chemical Formula 2-3]

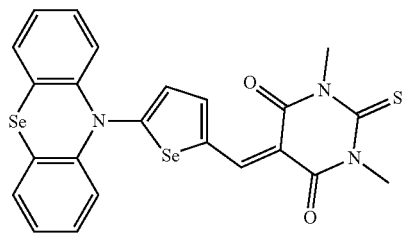

[Reaction Scheme 2-3]

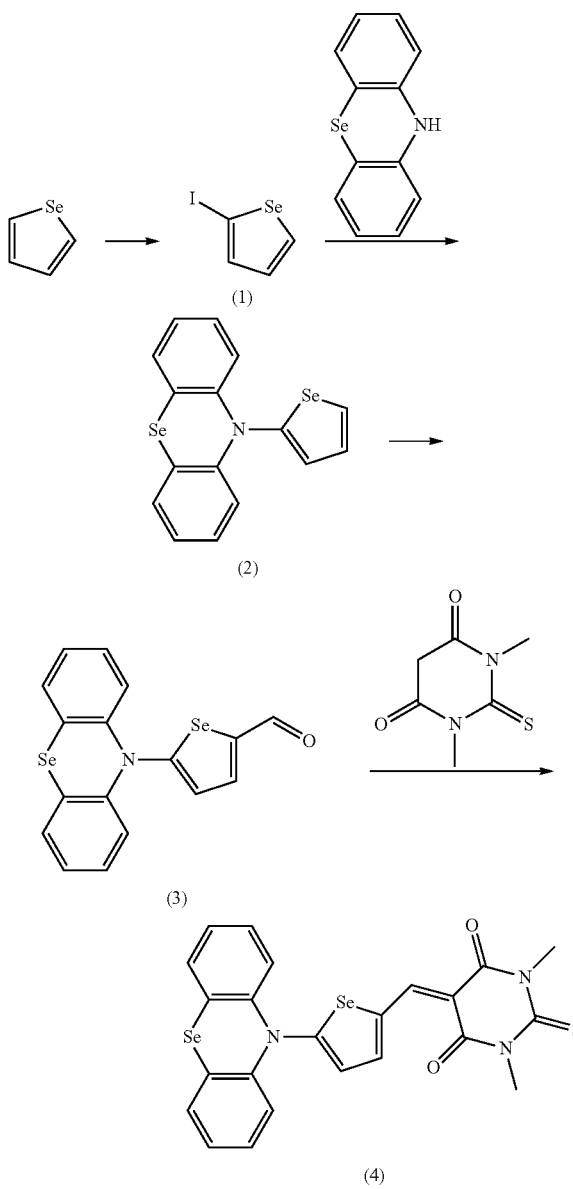

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 8.71 g (35.4 mmol) of 10H-phenoselenazine are heated and refluxed in 100 ml of anhydrous toluene in the presence of 5 mol % of Pd(dba)$_2$, 5 mol % of P(tBu)$_3$, and 10.2 g (106.15 mmol) of NaOtBu for 2 hours. A product obtained therefrom is separated and purified through silica gel column chromatography (toluene:hexane=1:4 (volume ratio)) to obtain 8.2 g of 10-(selenophen-2-yl)-10H-phenoselenazine (yield: 54.7%).

(iii) Synthesis of Compound (3)

8.0 ml of phosphoryl chloride is added in a dropwise fashion to 30.0 ml of N,N-dimethylformamide at −15° C., and the mixture is stirred at room temperature (24° C.) for 2 hours. A resultant therefrom is slowly added in a dropwise fashion to a mixture of 180 ml of dichloromethane and 8.2 g of Compound (2) at −15° C., and the obtained mixture is stirred at room temperature for 30 minutes and concentrated under a reduced pressure. Subsequently, 200 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 4.5 g of 5-(10H-phenoselenazin-10-yl)selenophene-2-carbaldehyde (yield: 51.1%).

(iv) Synthesis of Compound (4) Represented by Chemical Formula 2-3

2.00 g (4.96 mmol) of Compound (3) is suspended in ethanol, 1.03 g (5.95 mmol) of 1,3-dimethyl-2-thiobarbituric acid is added thereto, and the mixture is reacted at 50° C. for 2 hours to obtain 2.15 g of a final compound represented by Chemical Formula 2-3 (yield: 77.8%). The compound is sublimed and purified up to purity of 99.9%.

$^1$H-NMR (500 MHz, Methylene Chloride-d$_2$): δ 8.29 (s, 1H), 7.83 (d, 1H), 7.73 (d, 2H), 7.51 (d, 2H), 7.37 (t, 2H), 7.16 (t, 2H), 5.32 (d, 1H), 3.67 (d, 6H).

Reference Synthesis Example 4: Synthesis of Compound Represented by Chemical Formula 2-4

[Chemical Formula 2-4]

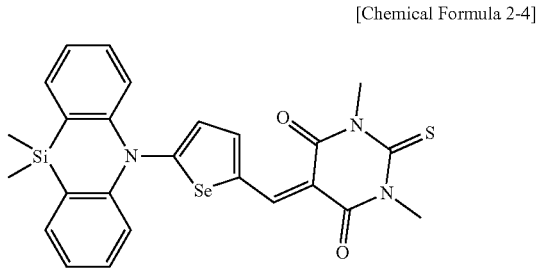 [SMILES: CN1C(=O)C(=Cc2ccc(N3c4ccccc4[Si](C)(C)c4ccccc43)[se]2)C(=O)N(C)C1=S]

[Reaction Scheme 2-4]

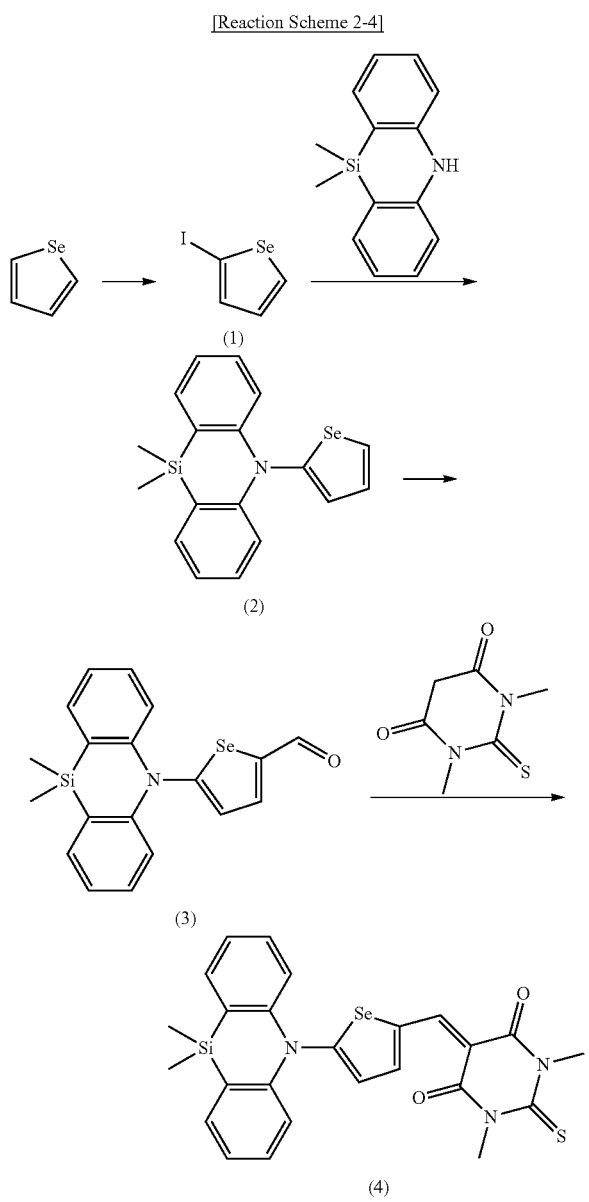

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (58.4 mmol) of 2-iodoselenophene and 11.9 g (58.4 mmol) of 10,10-dimethyl-5,10-dihydrodibenzo[b,e][1,4]azasiline are heated and refluxed in 200 ml of anhydrous toluene in the presence of 5 mol % of Pd(dba)$_2$, 5 mol % of P(tBu)$_3$, and 15.3 g (159.22 mmol) of NaOtBu for 2 hours. A product therefrom is separated and purified through silica gel column chromatography (toluene: hexane in a volume ratio of 1:4) to obtain 11.2 g of 10,10-dimethyl-5-(selenophen-2-yl)-5,10-dihydrodibenzo[b,e][1,4]azasiline (yield: 49.0%).

(iii) Synthesis of Compound (3)

8.2 ml of phosphoryl chloride is added in a dropwise fashion to 38.0 ml of N,N-dimethylformamide at −15° C., and the mixture is stirred at room temperature (24° C.) for 2 hours. A resultant therefrom is slowly added in a dropwise fashion to a mixture of 300 ml of dichloromethane and 11.2 g of Compound (2) at −15° C., and the obtained mixture is stirred at room temperature for 30 minutes and concentrated under a reduced pressure. Subsequently, 300 ml of water is added thereto, an aqueous sodium hydroxide solution is added thereto until pH becomes 14, and the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product therefrom is separated and purified through silica gel column chromatography (hexane:ethyl acetate in a volume ratio of 4:1) to obtain 6.82 g of 5-(10,10-dimethyldibenzo[b,e][1,4]azasilin-5(10H)-yl)selenophene-2-carbaldehyde (yield: 54.0%).

(iv) Synthesis of Compound (4) Represented by Chemical Formula 2-4

3.00 g (7.85 mmol) of Compound (3) is suspended in ethanol, 1.62 g (9.41 mmol) of 1,3-dimethyl-2-thiobarbituric acid is added thereto, and then reacted at 50° C. for 2 hours to obtain 3.15 g of a final compound represented by Chemical Formula 2-4 (yield: 74.8%). The compound is sublimed and purified up to purity of 99.9%.

$^1$H-NMR (500 MHz, Methylene Chloride-d$_2$): δ 8.46 (s, 1H), 8.26 (d, 1H), 7.80 (d, 2H), 7.71 (d, 2H), 7.56 (t, 2H), 7.50 (t, 2H), 6.93 (d, 1H), 3.68 (d, 6H), 0.45 (s, 6H).

Reference Synthesis Example 5: Synthesis of Compound Represented by Chemical Formula 2-5

[Chemical Formula 2-5]

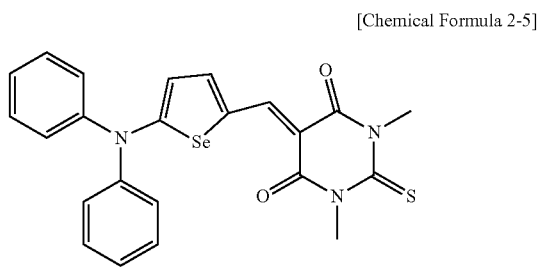 [SMILES: CN1C(=O)C(=Cc2ccc(N(c3ccccc3)c3ccccc3)s2)C(=O)N(C)C1=S]

[Reaction Scheme 2-5]

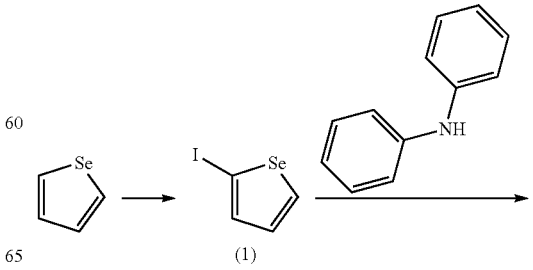

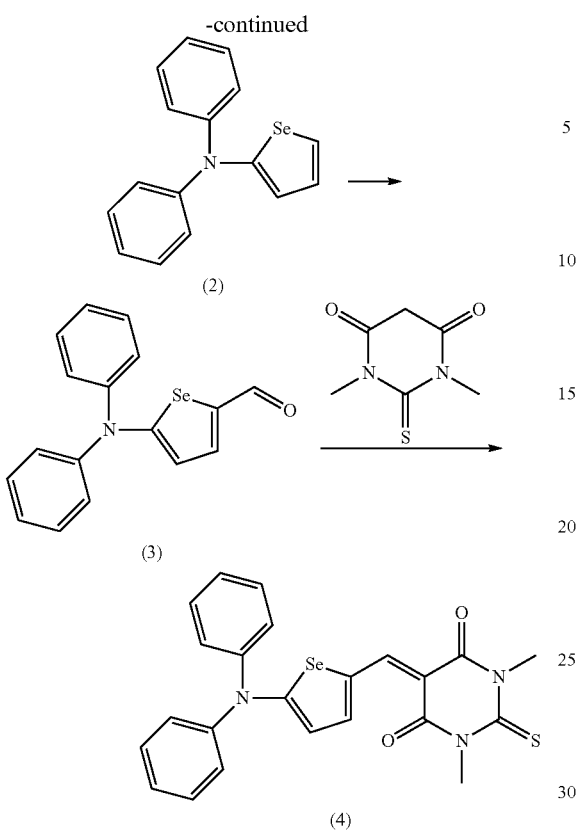

(2)

(3)

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

2.0 g (7.80 mmol) of 2-iodoselenophene (Compound (1)) and 1.2 g (7.09 mmol) of diphenylamine are heated and refluxed in 30 ml of anhydrous toluene in the presence of 5 mol % of Pd(dba)$_2$, 5 mol % of P(tBu)$_3$, and 0.75 g (7.80 mmol) of NaOtBu for 2 hours. A product obtained therefrom is separated and purified through silica gel column chromatography (toluene: hexane=volume ratio of 1:4) to obtain 1.40 g of Compound (2) (yield: 66.2%).

(iii) Synthesis of Compound (3)

1.75 ml of phosphoryl chloride is added in a dropwise fashion to 6.0 ml of N,N-dimethylform amide at −15° C., and the mixture is stirred at room temperature (24° C.) for 2 hours. A resultant therefrom is slowly added in a dropwise fashion to a mixture of 60 ml of dichloromethane and 1.4 g of Compound (2) at −15° C., and the obtained mixture is stirred at room temperature for 30 minutes and concentrated under a reduced pressure. Subsequently, 100 ml of water is added thereto, an aqueous sodium hydroxide solution is added thereto until pH becomes 14, and then, the obtained mixture is stirred at room temperature (24° C.) for 2 hours. An organic layer is extracted therefrom with dichloromethane, washed by using an aqueous sodium chloride solution, and dried by adding anhydrous magnesium sulfate thereto. A product obtained therefrom is separated and purified through silica gel column chromatography (hexane:ethyl acetate=4:1 (volume ratio)) to obtain 1.0 g of Compound (3) (yield: 65.3%).

(iv) Synthesis of Compound (4) Represented by Chemical Formula 2-5

0.33 g (1.09 mmol) of Compound (3) is suspended in ethanol, 0.23 g (1.3 mmol) of 1,3-dimethyl-2-thiobarbituric acid is added thereto, and the mixture is reacted at 50° C. for 2 hours to obtain 0.47 g of a compound represented by Chemical Formula 2-5 (yield: 90%).

$^1$H NMR ppm (CDCl3) 8.5 (s)-1H, 7.9 (d)-1H, 7.5-7.3 (m)-10H, 6.6 (d)-1H, 3.8 (d)-6H Comparative Synthesis Example 1: Synthesis of Compound Represented by Chemical Formula 3-1

[Chemical Formula 3-1]

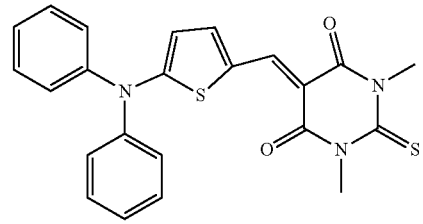

[Reaction Scheme 3-1]

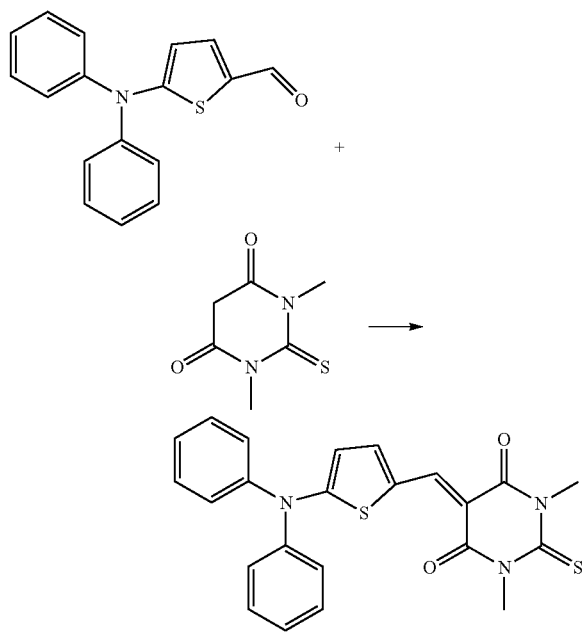

5-(diphenylamino)thiophene-2-carbaldehyde is synthesized in a method described in Dalton Transactions, 44 3, 1473-1482; 2015 and then, condensation-reacted with 1,3-dimethyl-2-thiobarbituric acid to obtain a compound according to Comparative Synthesis Example 1.

$^1$H NMR ppm (CDCl3) 8.4 (s)-1H, 7.8 (d)-1H, 7.5-7.3 (m)-10H, 6.5 (d)-1H, 3.7 (d)-6H Evaluation 1: Light Absorption Characteristics of Compounds of Synthesis Examples 1 to 7

Light absorption characteristics (maximum absorption wavelength ($\lambda_{max}$), full width at half maximum (FWHM), and absorption coefficient) of the compounds according to Synthesis Examples 1 to 7 depending on a wavelength are evaluated. Each compound according to Synthesis Examples 1 to 7 is deposited to manufacture thin films and light absorption characteristics in an ultraviolet-visible (UV-Vis) region of each film are evaluated using Cary 5000 UV Spectroscopy (Varian Inc.). HOMO energy levels are measured using an AC-3 photoelectron spectrophotometer (RIKEN KEIKI) and LUMO energy levels are calculated using energy bandgaps measured by Cary 5000 UV spectroscopy (Varian Inc.). Of them, the results of Synthesis Example 1, Synthesis Example 3, and Synthesis Example 4 are shown in Table 1.

TABLE 1

| Compounds | $\lambda_{max}$ (nm) | FWHM (nm) | Abs. coeff. ($10^5$ cm$^{-1}$) | HOMO (eV) | LUMO (eV) |
| --- | --- | --- | --- | --- | --- |
| Synthesis Example 1 | 559 | 86 | 1.27 | −5.44 | −3.42 |
| Synthesis Example 3 | 549 | 79 | 1.25 | −5.75 | −3.70 |
| Synthesis Example 4 | 554 | 74 | 1.42 | −5.55 | −3.48 |

Referring to Table 1, the compounds of Synthesis Example 1, Synthesis Example 3, and Synthesis Example 4 show maximum absorption wavelengths in a green wavelength region, narrow full widths at half maximum (FWHM), and high absorption coefficient (indicating high absorption intensities). From the results, the compounds of Synthesis Example 1, Synthesis Example 3, and Synthesis Example 4 have improved absorption selectivity in a green wavelength region. From the energy levels, the compounds of Synthesis Example 1, Synthesis Example 3, and Synthesis Example 4 are desirable for a p-type semiconductor.

In addition, each compound of Synthesis Examples 1 to 7 and C60 (n-type semiconductor) are codeposited in a volume ratio of 1:1 to manufacture thin films. Light absorption characteristics in an ultraviolet-visible (UV-Vis) region of each film are evaluated using Cary 5000 UV Spectroscopy (Varian Inc.). Of them, the results of Synthesis Examples 1 to 4 are shown in Table 2.

TABLE 2

| Compounds | $\lambda_{max}$ (nm) | FWHM (nm) | Abs. coeff. ($10^4$ cm$^{-1}$) |
| --- | --- | --- | --- |
| Synthesis Example 1 | 545 | 86 | 6.71 |
| Synthesis Example 2 | 549 | 77 | 7.60 |
| Synthesis Example 3 | 537 | 81 | 7.27 |
| Synthesis Example 4 | 540 | 74 | 8.07 |

Referring to Table 2, the compounds of Synthesis Examples 1 to 4 also show maximum absorption wavelengths in a green wavelength region, narrow full widths at half maximum (FWHM), and high absorption coefficient when they are used with the n-type semiconductor. From the results, the compounds of Synthesis Examples 1 to 4 have improved absorption selectivity in a green wavelength region.

Evaluation 2: Thermal Stability of Compounds of Synthesis Examples 1 to 7 and Reference Synthesis Examples 1 to 5

Thermal stability of the compounds according to Synthesis Examples 1 to 7 and Reference Synthesis Examples 1 to 5 is evaluated by measuring a 10 wt % loss temperature ($Ts_{10}$, a deposition temperature) at 10 Pa and a 50 wt % loss temperature ($Ts_{50}$, a deposition temperature) at 10 Pa. The deposition temperatures are measured in a thermal gravimetric analysis (TGA) method. Of them, the results of Synthesis Examples 1 to 4, 6, and 7 are shown in Table 3.

TABLE 3

| | Chemical Formulae | Tm (° C.) | $Ts_{10}$ (10 wt %, 10 Pa) (° C.) | $Ts_{50}$ (50 wt %, 10 Pa) (° C.) | ΔT (Tm-$Ts_{10}$) (° C.) |
| --- | --- | --- | --- | --- | --- |
| Synthesis Example 1 | Chemical Formula 1-1 | 356 | 262 | 289 | 94 |
| Synthesis Example 2 | Chemical Formula 1-2 | 306 | 230 | 256 | 76 |

TABLE 3-continued

| | Chemical Formulae | Tm (° C.) | $Ts_{10}$ (10 wt %, 10 Pa) (° C.) | $Ts_{50}$ (50 wt %, 10 Pa) (° C.) | ΔT (Tm-$Ts_{10}$) (° C.) |
| --- | --- | --- | --- | --- | --- |
| Synthesis Example 3 | Chemical Formula 1-3 | 281 | 248 | 280 | 33 |
| Synthesis Example 4 | Chemical Formula 1-4 | 331 | 243 | 271 | 88 |
| Synthesis Example 6 | Chemical Formula 1-6 | 320 | 247 | 272 | 73 |
| Synthesis Example 7 | Chemical Formula 1-7 | 322 | 238 | 268 | 84 |

When a compound has a lower melting point than a deposition temperature during the vacuum deposition, the compound may be decomposed and simultaneously gasified and thus fails to be formed into a film. Accordingly, the melting point of a compound may desirably be higher than the deposition temperature. Referring to Table 3, the compounds according to Synthesis Synthesis Examples 1 to 4, 6, and 7 may have greater than or equal to 33° C. higher melting point than the deposition temperature. Therefore, the compounds according to Synthesis Examples 1 to 4, 6, and 7 have a high difference between melting point and deposition temperature and thus may secure process stability.

Example 1: Manufacture of Photoelectric Device

An about 150 nm-thick anode is formed by sputtering ITO on a glass substrate, and a 100 nm-thick active layer is formed thereon by codepositing a compound represented by Chemical Formula 1-1 according to Synthesis Example 1 (a p-type semiconductor compound) and C60 (an n-type semiconductor compound) in a volume ratio of 1:1. Subsequently, a 10 nm-thick molybdenum oxide ($MoO_x$, 0<x≤3) thin film is formed thereon as a charge auxiliary layer. On the molybdenum oxide thin film, a 7 nm-thick cathode is formed by sputtering ITO, manufacturing an photoelectric device.

Examples 2 to 7: Manufacture of Photoelectric Device

Photoelectric devices according to Examples 2 to 7 are manufactured according to the same method as Example 1 except for respectively using the compounds according to Synthesis Examples 2 to 7 instead of the compound according to Synthesis Example 1.

Reference Examples 1 to 5: Manufacture of Photoelectric Device

Photoelectric devices according to Reference Examples 1 to 5 are manufactured according to the same method as Example 1 except for respectively using the compounds according to Reference Synthesis Example 1 to 5 instead of the compound according to Synthesis Example 1.

Evaluation 3: Light Absorption Characteristics of Photoelectric Device

Light absorption characteristics of photoelectric devices according to Examples 1 to 7 and Reference Examples 1 to 5 in an ultraviolet-visible (UV-Vis) region are evaluated using Cary 5000 UV Spectroscopy (Varian Inc.). Of them, the results of Examples 1 to 6 and Reference Examples 1 and 3 are shown in Table 4.

TABLE 4

|  | $\lambda_{max}$ (nm) | FWHM (nm) |
|---|---|---|
| Example 1 | 550 | 120 |
| Example 2 | 550 | 100 |
| Example 3 | 540 | 109 |
| Example 4 | 540 | 96 |
| Example 5 | 545 | 90 |
| Example 6 | 545 | 90 |
| Reference Example 1 | 520 | 105 |
| Reference Example 3 | 515 | 107 |

Referring to Table 4, the photoelectric devices according to Examples 1 to 6 including the compounds according to Synthesis Examples 1 to 6 show maximum absorption wavelengths in a green wavelength region of greater than or equal to 540 nm and narrow FWHMs, which show improved wavelength selectivity in a green wavelength region.

Evaluation 4: External Quantum Efficiency (EQE) of Photoelectric Device

External quantum efficiency (EQE) of the photoelectric devices according to Examples 1 to 7 and Reference Examples 1 to 5 is evaluated. The external quantum efficiency (EQE) is measured by using an IPCE measurement system (McScience Inc., Korea). The EQE is measured at a wavelength ranging from about 350 to about 750 nm by calibrating IPCE measurement system with the Si photodiode (Hamamatsu Photonics K. K., Japan) and respectively mounting the photoelectric devices according to Examples 1 to 7 and Reference Examples 1 to 5.

In addition, after the photoelectric devices according to Examples 1 to 7 and Reference Examples 1 to 5 are annealed at 160° C. for 3 hours, at 170° C. for 3 hours, and at 180° C. for 3 hours, EQE is measured at a wavelength ranging from about 350 nm to about 750 nm using the measurement system.

Of them, the results of Examples 1 to 7 are shown in Table 5. In Table 5, the external quantum efficiency is measured at a maximum light absorption wavelength when a –3V voltage is applied thereto.

TABLE 5

| | EQE (%) at −3 V | | | |
|---|---|---|---|---|
| Examples | Not annealed | 160° C. (3 h) | 170° C. (3 h) | 180° C. (3 h) |
| Example 1 | 51 | 53 | 54 | 56 |
| Example 2 | 59 | 59 | 58 | 58 |
| Example 3 | 53 | 56 | 47 | 49 |
| Example 4 | 66 | 66 | 67 | 65 |
| Example 5 | 59 | 59 | 56 | 42 |
| Example 6 | 53 | 54 | 52 | 53 |
| Example 7 | 62 | 64 | 62 | 62 |

Referring to Table 5, the photoelectric devices according to Examples 1 to 7 show excellent external quantum efficiency after being annealed at high temperature as well as at room temperature (Not annealed).

In addition, after the photoelectric devices according to Examples 3, 4 and 7 and Reference Example 4 are annealed at 190° C. for 3 hours, EQE is measured at a wavelength ranging from about 350 nm to about 750 nm using the measurement system. The results are shown in Table 6.

TABLE 6

| Examples | EQE (%) at −3 V |
|---|---|
| Example 3 | 44 |
| Example 4 | 64 |
| Example 7 | 62 |
| Reference Example 4 | — |

In Table 6, the thin film of the photoelectric device according to Reference Example 4 is damage and thus EQE may not be measured. On the contrary, the photoelectric devices according to Examples 3, 4 and 7 show good external quantum efficiency after being annealed at a high temperature of 190° C.

Evaluation 5: Dark Current of Photoelectric Device

Dark current (DC) of the photoelectric device according to Examples 1 to 7 and Reference Examples 1 to 5 is evaluated. The dark current is measured by using an IPCE measurement system (McScience Inc., Korea). The dark current is measured at a wavelength ranging from about 350 to about 750 nm by calibrating IPCE measurement system with the Si photodiode (Hamamatsu Photonics K. K., Japan) and respectively mounting the photoelectric devices according to Examples 1 to 7 and Reference Examples 1 to 5.

In addition, after the photoelectric devices according to Examples 1 to 7 and Reference Examples 1 to 5 are annealed at 160° C. for 3 hours, at 170° C. for 3 hours, and at 180° C. for 3 hours, dark currents are measured at a wavelength ranging from about 350 to about 750 nm using the measurement system.

Of them, the results of Example 1 to 4 are shown in Table 7. In Table 7, the dark current is measured at a maximum light absorption wavelength when a –3V voltage is applied thereto.

TABLE 7

| | DC(h/s/$\mu$m$^2$) | | |
|---|---|---|---|
| Examples | 160° C. (3 h) | 170° C. (3 h) | 180° C. (3 h) |
| Example 1 | 47 | 220 | 3700 |
| Example 2 | 19 | 414 | 600 |

TABLE 7-continued

| | DC(h/s/μm²) | | |
|---|---|---|---|
| Examples | 160° C. (3 h) | 170° C. (3 h) | 180° C. (3 h) |
| Example 3 | 44 | 21 | 49 |
| Example 4 | 4 | 4 | 4 |

Referring to Table 7, the photoelectric devices according to Examples 1 to 4 show low dark currents after being annealed at high temperature.

Response Time of Photoelectric Device

The response time (lag time) of the photoelectric devices according to Examples 1 to 7 and Reference Examples 1 to 5 is evaluated. The response time is measured by using incident LED light having a middle wavelength of 530 nm from an upper electrode (a cathode), applying it with electric intensity of 3 V/100 nm to the photoelectric devices according to Examples 1 to 7 and Reference Examples 1 to 5, and measuring an after-image current 0.1 second later after turning off the LED light. In addition, in order to evaluate thermal stability of the photoelectric devices according to Examples 1 to 7 and Reference Examples 1 to 5, after the photoelectric devices according to Examples 1 to 7 and Reference Examples 1 to 5 are annealed at 160° C. for 3 hours, at 170° C. for 3 hours, and at 180° C. for 3 hours, response times after being allowed at a high temperature are measured according to the same method as described above.

Of them, the results of Example 1 to 4 are shown in Table 8.

TABLE 8

| | Lag time @10 μW/cm² (ms) | | |
|---|---|---|---|
| | 160° C. (3 h) | 170° C. (3 h) | 180° C. (3 h) |
| Example 1 | 166 | 188 | 270 |
| Example 2 | 460 | 498 | 88 |
| Example 3 | 439 | 406 | 415 |
| Example 4 | 127 | 58 | 51 |

Referring to Table 8, the photoelectric devices according to Examples 1 to 4 show fast response times after being annealed at high temperature.

Sensitivity (YSNR10) of Image Sensor

The photoelectric devices according to Examples 1 to 4 and Reference Example 4 are respectively disposed to manufacture image sensors to have the structure of a photoelectric device 100 of an image sensor 300 as shown in FIG. 4.

YSNR10 and a color difference ΔE*ab from 24 colors of a Macbeth chart are measured by taking a photo of an 18% gray patch of the Macbeth chart under a light source of D-65.

Herein, lens has an F value of 2.8 and transmittance of 80%, and interference-type lens are used for an infrared ray cut filter. A pixel size of the image sensors is 1.4 μm, and a frame rate of the image sensors is 15 fps.

The YSNR10 is obtained in a method described in Juha Alakarhu's "Image Sensors and Image Quality in Mobile Phones" printed in the outline of 2007 International Image Sensor Workshop (Ogunquit Me., USA). The YSNR10 (luminance) is obtained at ΔE*ab=3 by compensating a color with CCM (Color Correction Matrix). After allowing the image sensors to stand at 160° C. for 3 hours, YSNR10 at ΔE*ab=3 is measured. Of them, the results of Example 4 and Reference Example 4 are shown in Table 9.

TABLE 9

| | YSNR10 (lux) | YSNR10 (160° C., 3 h) (lux) |
|---|---|---|
| Example 4 | 94 | 94 |
| Reference Example 4 | 105 | 106 |

Referring to Table 9, the image sensor including the photoelectric device according to Example 4 have low YSNR10 of less than or equal to 94 at ΔE*ab=3 color-compensated with CCM (Color Correction Matrix) and thus may accomplish high sensitivity at high image quality pixels of 1.4 μm. In addition, the image sensor including the photoelectric device according to Example 4 shows unchanged YSNR10 after being annealed at high temperature.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound represented by Chemical Formula 1:

[Chemical Formula 1]

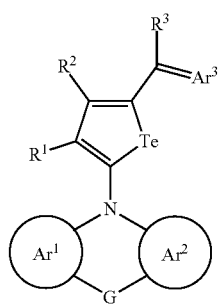

wherein, in Chemical Formula 1, $R^1$ to $R^3$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, $R^1$ and $R^2$ independently are present or linked with each other to provide a ring, $Ar^1$ and $Ar^2$ are independently one of a substituted or unsubstituted C6 to C30 arene group, a substituted or unsubstituted C3 to C30 heteroarene group, or a combination thereof in a condensed ring, G is one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond, wherein R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{jj}$, R$^{mm}$, and R$^{nn}$ are independently one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ are linked with each other to provide a ring structure, and n in —(CR$^d$R$^e$)$_n$— is 1 or 2, and Ar$^3$ is a cyclic group represented by Chemical Formula 2B,

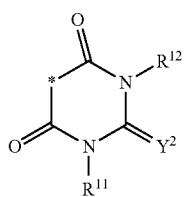

[Chemical Formula 2B]

wherein, in Chemical Formula 2B,

Y$^2$ is one of O, S, Se, Te, or C(R$^a$)(CN), wherein R$^a$ is one of hydrogen, a cyano group (—CN), or a C1 to C10 alkyl group), R$^{11}$ and R$^{12}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

2. The compound of claim 1, wherein in Chemical Formula 1, at least one of Ar$^1$ and Ar$^2$ includes a heteroatom at No. 1 position, and the heteroatom is one of nitrogen (N), sulfur (S), or selenium (Se).

3. The compound of claim 1, wherein an electron donor moiety of the N-containing hetero aromatic ring in Chemical Formula 1 is represented by Chemical Formula 4A:

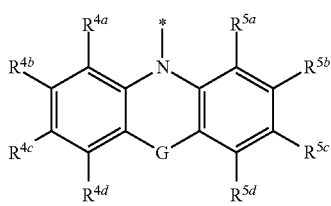

[Chemical Formula 4A]

wherein, in Chemical Formula 4A,

G is one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond, wherein R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{jj}$, R$^{mm}$, and R$^{nn}$ are independently one of a substituted or unsubstituted C1 to C10 alkyl group, or a substituted or unsubstituted C6 to C10 aryl group, and at least one pair of R$^{gg}$ and R$^{hh}$, R$^{jj}$ and R$^{ii}$, or R$^{mm}$ and R$^{nn}$ are linked with each other to provide a ring structure, and n in —(CR$^d$R$^e$)$_n$— is 1 or 2, and R$^{4a}$ to R$^{4d}$ and R$^{5a}$ to R$^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of R$^{4a}$ to R$^{4d}$ are linked with each other to provide a 5-membered aromatic ring or a 6-membered aromatic ring, or two adjacent groups of R$^{5a}$ to R$^{5d}$ are linked with each other to provide a 5-membered aromatic ring or a 6-membered aromatic ring.

4. The compound of claim 1, wherein an electron donor moiety of the N-containing hetero aromatic ring in Chemical Formula 1 is represented by Chemical Formula 4B:

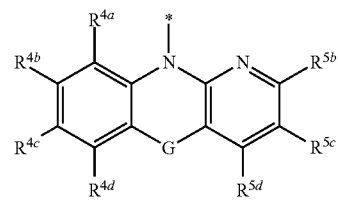

[Chemical Formula 4B]

wherein, in Chemical Formula 4B,

G is one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond wherein R$^d$, R$^e$, R$^f$, R$^g$, R$^h$, R$^i$, R$^j$, R$^m$, and R$^n$ are independently one of hydrogen, a halogen, a substituted or unsubstituted C1 to C10 alkyl group, or a substituted or unsubstituted C6 to C10 aryl group, wherein R$^{gg}$, R$^{hh}$, R$^{ii}$, R$^{mm}$, and R$^{nn}$ are independently one of a substituted or unsubstituted C1 to C10 alkyl group, or a substituted or unsubstituted C6 to C10 aryl group, and at least one pair of R$^{gg}$ and R$^{hh}$, R$^{ii}$ and R$^{jj}$, or R$^{mm}$ and R$^{nn}$ are linked with each other to provide a ring structure, and n in —(CR$^d$R$^e$)$_n$— is 1 or 2), and R$^{4a}$ to R$^{4d}$ and R$^{5b}$ to R$^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of R$^{4a}$ to R$^{4d}$ are linked with each other to provide a 5-membered aromatic ring or a 6-membered aromatic ring, or two adjacent groups of R$^{5b}$ to R$^{5d}$ are linked with each other to provide a 5-membered aromatic ring or a 6-membered aromatic ring.

5. The compound of claim 1, wherein an electron donor moiety of the N-containing hetero aromatic ring in Chemical Formula 1 is represented by Chemical Formula 4C:

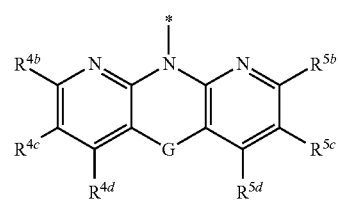

[Chemical Formula 4C]

wherein, in Chemical Formula 4C,

G is one of —(CR$^d$R$^e$)$_n$—, —O—, —S—, —Se—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond wherein R$^d$, $R^e$, $R^f$, $R^g$, $R^h$, $R^i$, $R^j$, $R^m$, and $R^n$ are independently one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ are independently one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ are linked with each other to provide a ring structure, and n in —$(CR^dR^e)_n$— is 1 or 2), and $R^{4b}$ to $R^{4d}$ and $R^{5b}$ to $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4b}$ to $R^{4d}$ are linked with each other to provide a 5-membered aromatic ring or a 6-membered aromatic ring, or two adjacent groups of $R^{5b}$ to $R^{5d}$ are linked with each other to provide a 5-membered aromatic ring or a 6-membered aromatic ring.

6. The compound of claim 1, wherein an electron donor moiety of the N-containing hetero aromatic ring in Chemical Formula 1 is represented by Chemical Formula 4D:

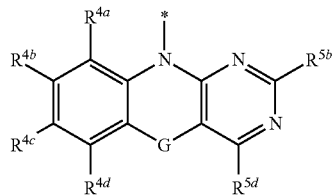

[Chemical Formula 4D]

wherein, in Chemical Formula 4D,

G is one of —$(CR^dR^e)_n$—, —O—, —S—, —Se—, —N═, —$NR^f$—, —$SiR^gR^h$—, —$SiR^{gg}R^{hh}$—, —$GeR^iR^j$—, —$GeR^{ii}R^{jj}$—, —$(C(R^m)═C(R^n))$—, —$(C(R^{mm})═C(R^{nn}))$—, or a single bond wherein $R^d$, $R^e$, $R^f$, $R^g$, $R^h$, $R^i$, $R^j$, $R^m$, and $R^n$ are independently one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{mm}$, and $R^{nn}$ are independently one of a substituted or unsubstituted C1 to C10 alkyl group, or a substituted or unsubstituted C6 to C10 aryl group, and at least one pair of $R^{gg}$ and $R^{hh}$, $R^{ii}$ and $R^{jj}$, or $R^{mm}$ and $R^{nn}$ are linked with each other to provide a ring structure, and n in —$(CR^dR^e)_n$— is 1 or 2), and $R^{4a}$ to $R^{4d}$ and $R^{5b}$ and $R^{5d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4a}$ to $R^{4d}$ are linked with each other to provide a 5-membered aromatic ring or a 6-membered aromatic ring.

7. The compound of claim 1, wherein an electron donor moiety of the N-containing hetero aromatic ring in Chemical Formula 1 is represented by Chemical Formula 4E:

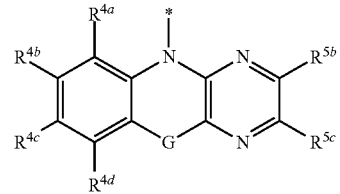

[Chemical Formula 4E]

wherein, in Chemical Formula 4E,

G is one of —$(CR^dR^e)_n$—, —O—, —S—, —Se—, —N═, —$NR^f$—, —$SiR^gR^h$—, —$SiR^{gg}R^{hh}$—, —$GeR^iR^j$—, —$GeR^{ii}R^{jj}$—, —$(C(R^m)═C(R^n))$—, —$(C(R^{mm})═C(R^{nn}))$—, or a single bond wherein $R^d$, $R^e$, $R^f$, $R^g$, $R^h$, $R^i$, $R^j$, $R^m$, and $R^n$ are independently one of hydrogen, a halogen, a substituted or unsubstituted C1 to C10 alkyl group, or a substituted or unsubstituted C6 to C10 aryl group, wherein $R^{gg}$, $R^{hh}$, $R^{ii}$, $R^{jj}$, $R^{mm}$, and $R^{nn}$ are independently one of a substituted or unsubstituted C1 to C10 alkyl group, or a substituted or unsubstituted C6 to C10 aryl group, and at least one of pair $R^{gg}$ and $R^{hh}$, $R^{ii}$ and $R^{jj}$, or $R^{mm}$ and $R^{nn}$ are linked with each other to provide a ring structure, and n in —$(CR^dR^e)_n$— is 1 or 2), and $R^{4a}$ to $R^{4d}$ and $R^{5b}$ and $R^{5e}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof, or two adjacent groups of $R^{4a}$ to $R^{4d}$ are linked with each other to provide a 5-membered aromatic ring or a 6-membered aromatic ring, or two adjacent groups of $R^{5b}$ and $R^{5e}$ are linked with each other to provide a 5-membered aromatic ring or a 6-membered aromatic ring.

8. The compound of claim 1, wherein the compound has a maximum absorption wavelength ($\lambda_{max}$) in a wavelength region of greater than or equal to about 5000 nm and less than or equal to about 600 nm.

9. The compound of claim 1, wherein the compound exhibits a light absorption curve having a full width at half maximum (FWHM) of about 50 nm to about 120 nm, in a thin film state.

10. The compound of claim 1, wherein a difference between a melting point of the compound and a deposition temperature at which 10 wt % of an initial weight of the compound is lost is greater than or equal to about 3° C.

11. A photoelectric device, comprising
a first electrode and a second electrode facing each other, and
an active layer between the first electrode and the second electrode, wherein
the active layer includes the compound of claim 1.

12. An image sensor comprising:
the photoelectric device of claim 11.

13. The image sensor of claim 12, wherein
the image sensor includes a semiconductor substrate and a photoelectric device on the semiconductor substrate,
the semiconductor substrate is integrated with a plurality of first photo-sensing devices configured to sense light in a blue wavelength region and a plurality of second photo-sensing devices configured to sense light in a red wavelength region, and the photoelectric device is configured to selectively sense light in a green wavelength region, and the photoelectric device is the photoelectric device of claim 11.

14. The image sensor of claim 13, further comprising:

a color filter layer on the semiconductor substrate, wherein the color filter layer includes a blue filter and a red filter, the blue filter is configured to selectively transmit light in a blue wavelength region, and the red filter is configured to selectively transmit light in a red wavelength region.

15. The image sensor of claim 13, wherein the first photo-sensing devices and the second photo-sensing devices are stacked in a vertical direction in the semiconductor substrate.

16. The image sensor of claim 12, wherein the photoelectric device is a green photoelectric device, the image sensor includes a blue photoelectric device configured to selectively absorb light in a blue wavelength region, the image sensor includes a red photoelectric device configured to selectively absorb light in a red wavelength region, and the green photoelectric device, the blue photoelectric device, and the red photoelectric device are stacked.

17. An electronic device comprising:

the image sensor of claim 12.

* * * * *